(12) United States Patent
Van Eijk et al.

(10) Patent No.: US 7,498,131 B2
(45) Date of Patent: Mar. 3, 2009

(54) ANALYSIS AND DETECTION OF MULTIPLE TARGET SEQUENCES USING CIRCULAR PROBES

(75) Inventors: Michael Josephus Theresia Van Eijk, Herpen (NL); Réne Cornelis Josephus Hogers, Ede (NL)

(73) Assignee: Keygene, NV, AE Wageningen (NL)

( * ) Notice: Subject to any disclaimer, the term of this patent is extended or adjusted under 35 U.S.C. 154(b) by 224 days.

(21) Appl. No.: 10/498,524

(22) PCT Filed: Dec. 16, 2002

(86) PCT No.: PCT/NL02/00834

§ 371 (c)(1),
(2), (4) Date: Sep. 13, 2005

(87) PCT Pub. No.: WO03/052142

PCT Pub. Date: Jun. 26, 2003

(65) Prior Publication Data

US 2006/0121458 A1    Jun. 8, 2006

(30) Foreign Application Priority Data

Dec. 14, 2001 (EP) .................................. 01204912

(51) Int. Cl.
*C12Q 1/68* (2006.01)
(52) U.S. Cl. ........................................................ 435/6
(58) Field of Classification Search .................. None
See application file for complete search history.

(56) References Cited

U.S. PATENT DOCUMENTS 6,156,178 A    12/2000    Peponnet et al. ............ 204/457

6,221,603 B1    4/2001    Mahtani ......................... 435/6

FOREIGN PATENT DOCUMENTS

| WO | WO 95 22623 | 8/1995 |
|---|---|---|
| WO | WO 96 15271 | 5/1996 |
| WO | WO 01 06012 | 1/2001 |

OTHER PUBLICATIONS

Baner, J. et al., More Keys to Padlock Probes: Mechanisms for High-Throughput Nucleic Acid Analysis, Current Opinion in Biotechnology. 2001, 12:11-15.
Grossman, P. et al., High-Density Multiplex Detection of Nucleic Acid Sequences: Oligonucleotide Ligation Assay and Sequence-Coded Separation, Nucleic Acids Research. 1994, vol. 22, No. 21, 4527-4534.
Landegren, U. et al., A Ligase-Mediated Gene Detection Technique, Science. 1988, 1077-1080.
Shi, M., Enabling Large-Scale Pharmacogenetic Studies by High-Throughput Mutation Detection and Genotyping Technologies, Clinical Chemistry. 47:2, 2001, 164-172.
Thomas, D. et al., Amplification of Padlock Probes for DNA Diagnostics by Cascade Rolling Circle Amplification or the Polymerase Chain Reaction, Arch Path Lab Med. vol. 123, Dec. 1999, 1170-1176.

*Primary Examiner*—James Martinell
(74) *Attorney, Agent, or Firm*—Browdy and Neimark, P.L.L.C.

(57) ABSTRACT

Method for the high throughput separation and detection of a multiplicity of target sequences in a multiplicity of samples comprising subjecting each sample to a ligation-dependent amplification assay followed by a multiple injection step comprising the consecutive and/or simultaneous injection of a multiplicity of samples, for instance in a multichannel electrophoretic device.

20 Claims, 16 Drawing Sheets

L, L1, L2, L3 = label

Fig 4
Locus 1
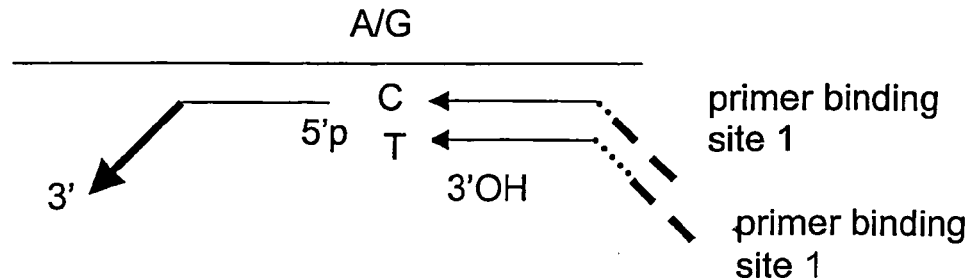
Locus 2
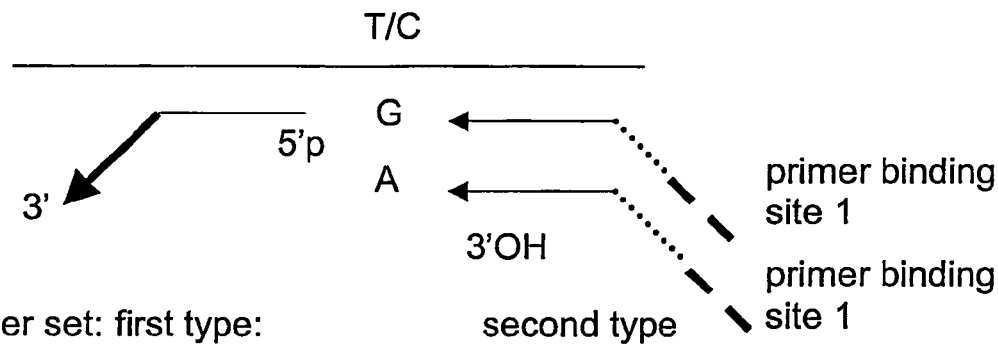
Primer set: first type:    second type
Connected probes with annealed primers:
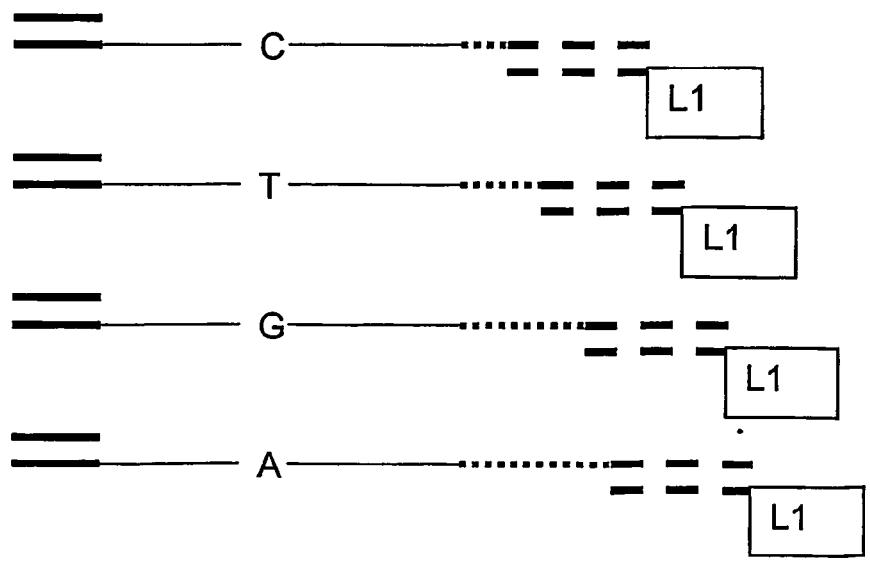

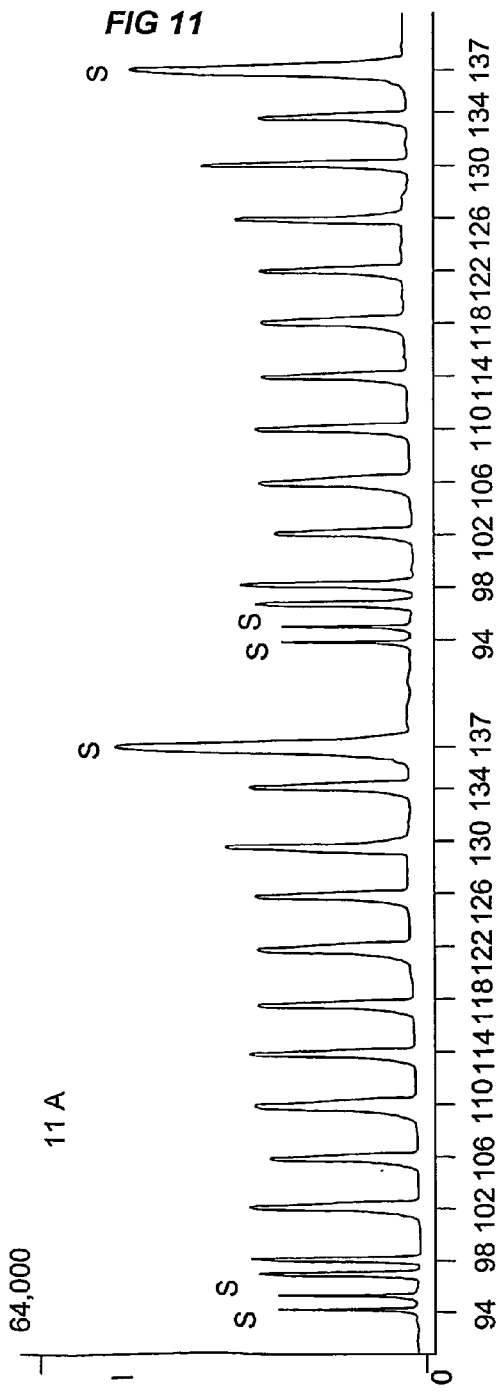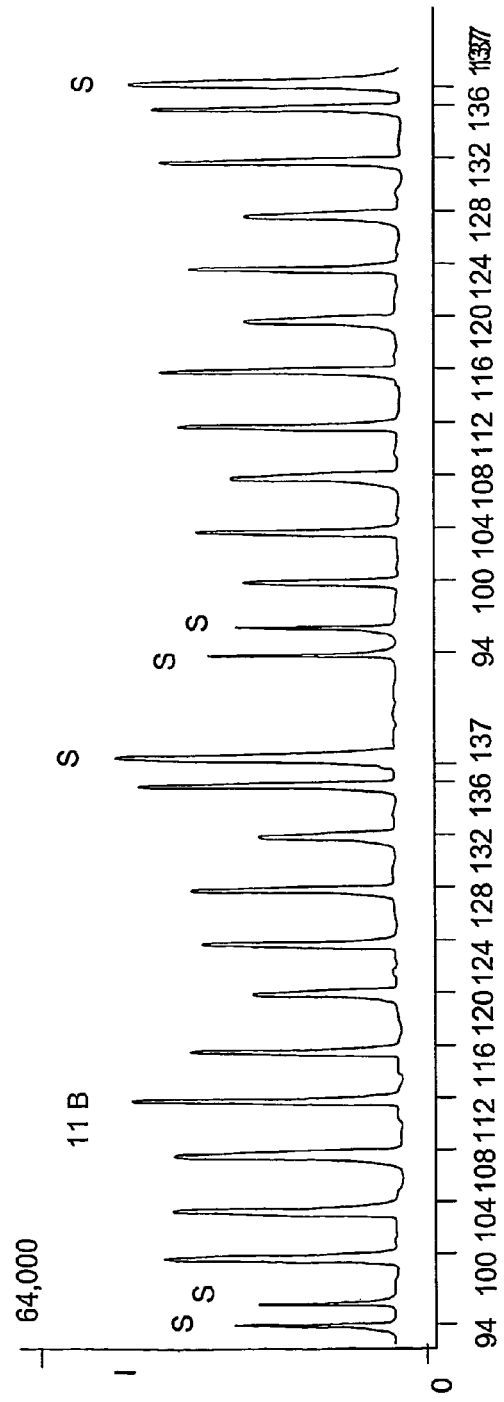
FIG 11

| bp | Observed data | | Scored data | | Expected data | |
|---|---|---|---|---|---|---|
| | 120 | 124 | 120 | 124 | 120 | 124 |
| ET-ROX | + | - | + | - | + | - |
| FAM | + | - | ⊖ | - | - | - |
| JOE | - | + | - | ⊖ | - | - |
| NED | - | + | - | + | - | + |

B

| bp | Observed data | | | Scored data | | | Expected data | | |
|---|---|---|---|---|---|---|---|---|---|
| | 120 | 121 | 124 | 125 | 120 | 121 | 124 | 125 | 120 | 121 | 124 | 125 |
| ET-ROX | + | - | - | - | + | ▓ | - | ▓ | + | ▓ | - | ▓ |
| FAM | + | - | - | - | ▓ | - | ▓ | - | ▓ | - | ▓ | - |
| JOE | - | - | + | - | - | ▓ | + | ▓ | - | ▓ | + | ▓ |
| NED | - | - | + | - | ▓ | - | ▓ | - | ▓ | - | - | - |

| Legend | |
|---|---|
| + | Present |
| - | Absent |
| ⊖ | False (Present/Absent) |
| ▓ | Signal ignored |

*Fig 14*
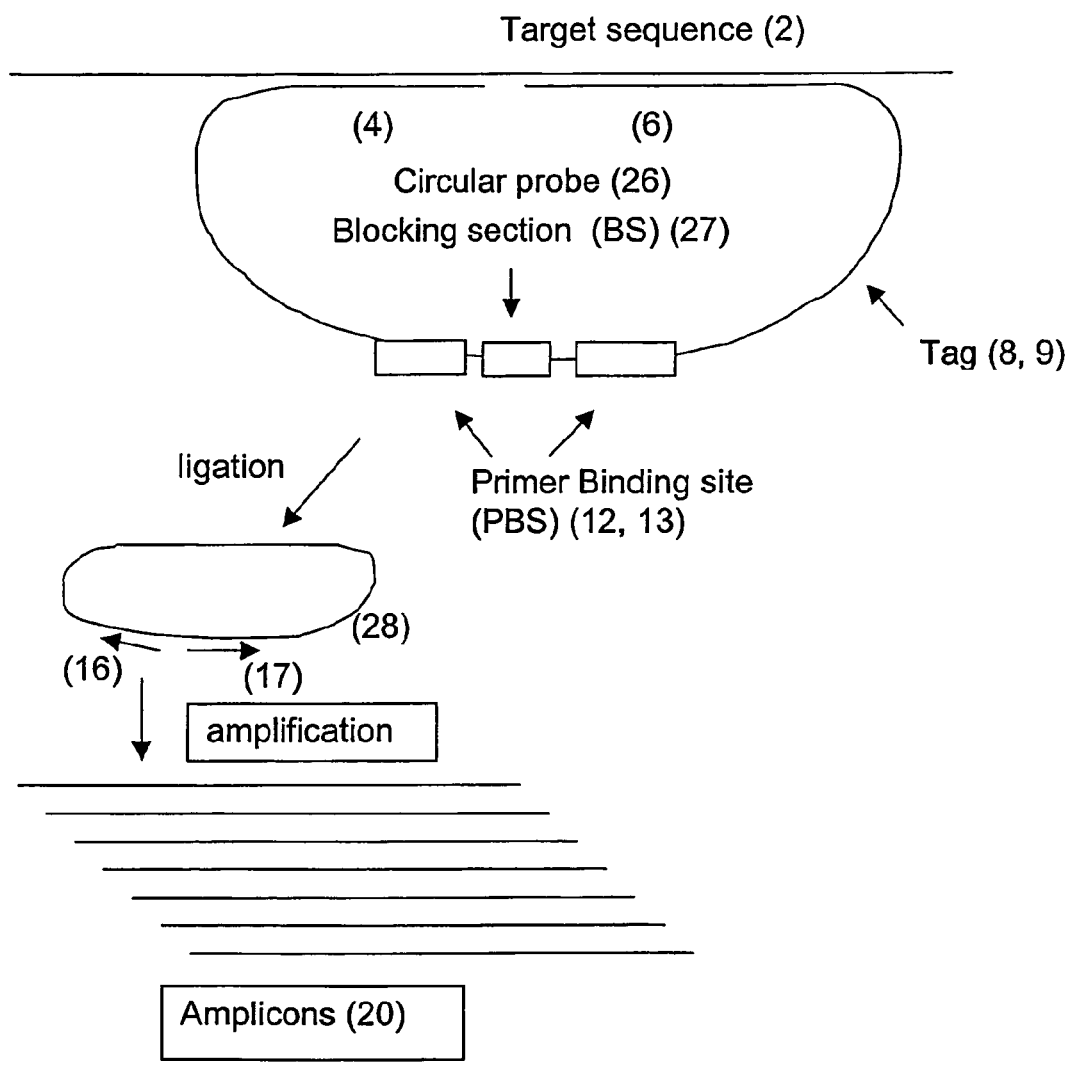
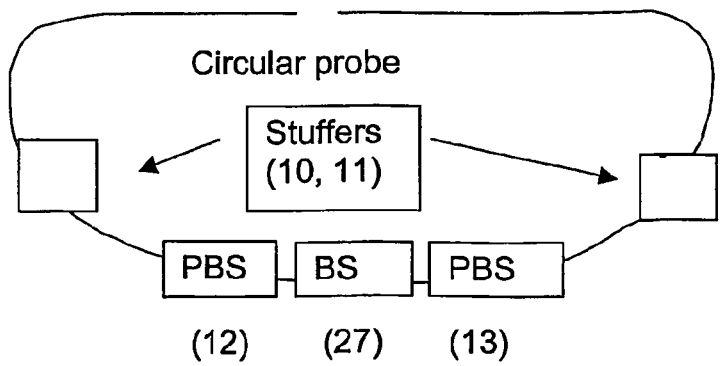

ANALYSIS AND DETECTION OF MULTIPLE TARGET SEQUENCES USING CIRCULAR PROBES

FIELD OF THE INVENTION

The present invention relates to the field of biotechnology. In particular the present invention provides a method for the high throughput separation and detection of nucleotide sequences, and the use of the method in the discrimination and identification of target sequence such as single nucleotide polymorphisms. The invention further provides for probes that are capable of hybridising to the target sequence of interest, primers for the amplification of ligated probes, use of these probes and primers in the identification and/or detection of nucleotide sequences that are related to a wide variety of genetic traits and genes and kits of primers and/or probes suitable for use in the method according to the invention.

BACKGROUND OF THE INVENTION

There is a rapidly growing interest in the detection of specific nucleic acid sequences. This interest has not only arisen from the recently disclosed draft nucleotide sequence of the human genome and the presence therein, as well as in the genomes of many other organisms, of an abundant amount of single nucleotide polymorphisms (SNP), but also from marker technologies such as AFLP. The recognition that the presence of single nucleotide substitutions (and other types of genetic polymorphisms such as small insertion/deletions; indels) in genes provide a wide variety of information has also attributed to this increased interest. It is now generally recognised that these single nucleotide substitutions are one of the main causes of a significant number of monogenically and multigenically inherited diseases, for instance in humans, or are otherwise involved in the development of complex phenotypes such as performance traits in plants and livestock species. Thus, single nucleotide substitutions are in many cases also related to or at least indicative of important traits in humans, plants and animal species.

Analysis of these single nucleotide substitutions and indels will result in a wealth of valuable information, which will have widespread implications on medicine and agriculture in the widest possible terms. It is for instance generally envisaged that these developments will result in patient-specific medication. To analyse these genetic polymorphisms, there is a growing need for adequate, reliable and fast methods that enable the handling of large numbers of samples and large numbers of (predominantly) SNPs in a high throughput fashion, without significantly compromising the quality of the data obtained.

Even though a wide diversity of high-throughput detection platforms for SNPs exist at present (such as fluorometers, DNA microarrays, mass-spectrometers and capillary electrophoresis instruments), the major limitation to achieve cost-effective high throughput detection is that a robust and efficient multiplex amplification technique for non-random selection of SNPs is currently lacking to utilise these platforms efficiently, which results in suboptimal use of these powerful detection platforms and/or high costs per datapoint. "Throughput" as used herein, defines a relative parameter indicating the number of samples and target sequences that can be analysed per unit of time.

Specifically, using common amplification techniques such as the PCR technique it is possible to amplify a limited number of target sequences by combining the corresponding primer pairs in a single amplification reaction but the number of target sequences that can be amplified simultaneously is small and extensive optimisation may be required to achieved similar amplification efficiencies of the individual target sequences. One of the solutions to multiplex amplification is to use a single primer pair for the amplification of all target sequences, which requires that all targets must contain the corresponding primer-binding sites. This principle is incorporated in the AFLP technique (EP-A 0 534 858). Using AFLP, the primer-binding sites result from a digestion of the target nucleic acid (i.e. total genomic DNA or cDNA) with one or more restriction enzymes, followed by adapter ligation. AFLP essentially targets a random selection of sequences contained in the target nucleic acid. It has been shown that, using AFLP, a practically unlimited number of target sequences can be amplified in a single reaction, depending on the number of target sequences that contain primer-binding region(s) that are perfectly complementary to the amplification primers. Exploiting the use of single primer-pair for amplification in combination with a non-random method for SNP target selection and efficient use of a high throughput detection platform may therefore substantially increase the efficiency of SNP genotyping, however such technology has not been provided in the art yet.

One of the principal methods used for the analysis of the nucleic acids of a known sequence is based on annealing two probes to a target sequence and, when the probes are hybridised adjacently to the target sequence, ligating the probes. The OLA-principle (Oligonucleotide Ligation Assay) has been described, amongst others, in U.S. Pat. No. 4,988,617 (Landegren et al.). This publication discloses a method for determining the nucleic acid sequence in a region of a known nucleic acid sequence having a known possible mutation. To detect the mutation, oligonucleotides are selected to anneal to immediately adjacent segments of the sequence to be determined. One of the selected oligonucleotide probes has an end region wherein one of the end region nucleotides is complementary to either the normal or to the mutated nucleotide at the corresponding position in the known nucleic acid sequence. A ligase is provided which covalently connects the two probes when they are correctly base paired and are located immediately adjacent to each other. The presence or absence of the linked probes is an indication of the presence of the known sequence and/or mutation.

Abbot et al. in WO 96/15271 developed a method for a multiplex ligation amplification procedure comprising the hybridisation and ligation of adjacent probes. These probes are provided with an additional length segment, the sequence of which, according to Abbot et al, is unimportant. The deliberate introduction of length differences intends to facilitate the discrimination on the basis of fragment length in gel-based techniques.

WO 97/45559 (Barany et al.) describes a method for the detection of nucleic acid sequence differences by using combinations of ligase detection reactions (LDR) and polymerase chain reactions (PCR). Disclosed are methods comprising annealing allele-specific probe sets to a target sequence and subsequent ligation with a thermostable ligase, optionally followed by removal of the unligated primers with an exonuclease. Amplification of the ligated products with fluorescently labelled primers results in a fluorescently labelled amplified product. Detection of the products is based on separation by size or electrophoretic mobility or on an addressable array.

Detection of the amplified probes is performed on a universally addressable array containing capturing oligonucleotides. These capturing oligonucleotides contain a region that is capable of annealing to a pre-determined region in the amplified probe, a so-called zip-region or zip code. Each amplified probe contains a different zip code and each zip code will hybridise to its corresponding capturing oligonucleotide on the array. Detection of the label in combination with the position on the array provides information on the presence of the target sequence in the sample. This method allows for the detection of a number of nucleic acid sequences in a sample. However, the design, validation and routine use of arrays for the detection of amplified probes involves many steps (ligation, amplification, optionally purification of the amplified material, array production, hybridisation, washing, scanning and data quantification), of which some (particularly hybridisation and washing) are difficult to automate. Array-based detection is therefore laborious and costly to analyse a large number of samples for a large number of SNPs.

The LDR oligonucleotide probes in a given set may generate a unique length product and thus may be distinguished from other products based on size. For the amplification a primer set is provided wherein one of the primers contains a label. Different primers can be provided with different labels to allow for the distinction of products.

The method and the various embodiments described by Barany et al. are found to have certain disadvantages. One of the major disadvantages is that the method in principle does not provide for a true high throughput process for the determination of large numbers of target sequences in short periods of time using reliable and robust methods without compromising the quality of the data produced and the efficiency of the process.

More in particular, one of the disadvantages of the means and methods as disclosed by Barany et al. resides in the limited multiplex capacity when discrimination is based inter alia, on the length of the allele specific probe sets. Discrimination between sequences that are distinguishable by only a relatively small length difference is, in general, not straightforward and carefully optimised conditions may be required in order to come to the desired resolving power. Discrimination between sequences that have a larger length differentiation is in general easier to accomplish. This may provide for an increase in the number of sequences that can be analysed in the same sample. However, providing for the necessary longer nucleotide probes is a further hurdle to be taken. In the art, synthetic nucleotide sequences are produced by conventional chemical step-by-step oligonucleotide synthesis with a yield of about 98.5% per added nucleotide. When longer probes are synthesised (longer than ca. 60 nucleotides) the yield generally drops and the reliability and purity of the synthetically produced sequence can become a problem.

These and other disadvantages of the methods disclosed in WO 97/45559 and other publications based on oligonucleotide ligation assays herein lead the present inventors to the conclusion that the methods described therein are less preferable for adaptation in a high throughput protocol that is capable of handling a large number of samples each comprising large numbers of sequences.

The specific problem of providing for longer probes has been solved by Schouten et al. (WO 01/61033). WO 01/61033 discloses the preparation of longer probes for use in ligation-amplification assays. They provided probes that are considerably longer than those that can be obtained by conventional chemical synthesis methods to avoid the problem associated with the length-based discrimination of amplified products using slab-gels or capillary electrophoresis, namely that only a small part of the detection window/resolving capacity of up to 1 kilo base length is used when OLA probes are synthesised by chemical means. With an upper limit in practice of around 100-150 bases for chemically synthesised oligonucleotides according to the current state of technology, this results in amplification products that are less than 300 base pairs long at most, but often much less (see Barany et al.). The difficulty of generating such long probes (more than about 150 nucleotides) with sufficient purity and yield by chemical means has been countered by Schouten et al., using a method in which the probes have been obtained by an in vivo enzymatic template directed polymerisation, for instance by the action of a DNA polymerase in a suitable cell, such as an M13 phage.

However, the production and purification of such biological probes requires a collection of suitable host strains containing M13 phage conferring the desired length variations and the use of multiple short chemically synthesised oligonucleotides in the process, thus their use is very laborious and time-consuming, hence costly and not suitable for high-throughput assay development. Furthermore, the use of relatively long probes and relatively large length differences between the amplifiable target sequences may result in differential amplification efficiencies in favour of the shorter target sequences. This adversely affects the overall data quality, hampering the development of a true high throughput method. Thus the need for a reliable and cost-efficient solution to multiplex amplification and subsequent length-based detection for high throughput application remains.

Other solutions that have been suggested in the art such as the use of circular (padlock) probes in combination with isothermal amplification such as rolling circle amplification (RCA) are regarded as profitable because of the improved hybridisation characteristics of circular probes and the isothermal character of RCA.

Rolling circle amplification is an amplification method wherein a first primer is hybridised to a ligated or connected circular probe. Subsequent primer elongation, using a polymerase with strand displacement activity results in the formation of a long polynucleotide strand which contains multiple representations of the connected circular probe. Such a long strand of concatamers of the connected probe is subsequently detected by the use of hybridisation probes. These probes can be labelled. Exponential amplification of the ligated probe can be achieved by the hybridisation of a second primer that hybridises to the concatameric strand and is subsequently elongated. (Exponential) Rolling Circle Amplification ((E)RCA) is described inter alia in U.S. Pat. No. 5,854,033, U.S. Pat. No. 6,143,495 WO97/19193, Lizardi et al, Nature genetics 19(3):225-232 (1998).

U.S. Pat. No. 5,876,924, WO98/04745 and WO98/04746 by Zhang et al. describe a ligation reaction using two adjacent probes wherein one of the probes is a capture probe with a binding element such as biotin. After ligation, the unligated probes are removed and the ligated captured probe is detected using paramagnetic beads with a ligand (biotin) binding moiety. Zhang also discloses the amplification of circular probes using PCR primers in a rolling circle amplification, using a DNA polymerase with strand displacement activity, thereby generating a long concatamer of the circular probe, starting from extension of the first primer. A second PCR primer subsequently hybridises to the long concatamer and elongation thereof provides a second generation of concatamers and facilitates exponential amplification. Detection is generally based on the hybridisation of labelled probes.

However, these methods have proven to be less desirable in high throughput fashion. One of the reasons is that, for a high throughput method based on length discrimination, the use of (E)RCA results in the formation of long concatamers. These concatamers are problematic, as they are not suitable for high throughput detection.

U.S. Pat. No. 6,221,603 disclosed a circular probe that contains a restriction site. The probe is amplified using (E)RCA and the resulting concatamers are restricted at the restriction site. The restriction fragments are then separated by length and detected. Separation and detection is performed on a capillary electrophoretic platform, such as the MegaBACE equipment available from Molecular Dynamics Amersham-Pharmacia For detection labelled dNTP's may be incorporated into the fragments during amplification, or the fragments may be detected by staining or by labelled detection probes. Partial digestion by the restriction enzyme may however affect the reliability of the method. Furthermore, the methods for labelling of the fragments as disclosed in U.S. Pat. No. 6,221,603, do not allow to fully utilise the MegaBACE's capacity of simultaneous detection of multiple colours.

The present inventors have set out to eliminate or at least diminish the existing problems in the art while at the same time attempting to maintain the advantageous aspects thereof, and to further improve the technology. Other problems in the art and solutions provided thereto by the present invention will become clear throughout the description, the figures and the various embodiments and examples.

DESCRIPTION OF THE INVENTION

The present invention relates to methods for high throughput separation and detection of multiple sequences. The present method resolves many of the problems previously encountered in the art. More in particular the present invention provides for a multiple ligation and amplification assay that allows for the rapid and high throughput analysis of a multiplicity of samples, preferably containing a multiplicity of sequences. The present invention also provides for a method for the high throughput discrimination and detection of a multitude of nucleotide sequences based on a combination of length differences and labels. The present invention combines the advantages of certain methods while at the same time avoids disadvantages associated with the various technique, thereby providing for an improved method for the detection of targets sequences in a reliable and reproducible manner and suitable for a high throughput detection method.

DETAILED DESCRIPTION OF THE INVENTION

In a first aspect the invention relates to a method for high throughput separation and detection of a multiplicity of target sequences, optionally in a multiplicity of samples comprising subjecting each sample to a ligation-dependent amplification assay.

The method preferably is a method for determining the presence or absence of at least one target sequence (2) in a sample, wherein the method comprises the steps of:

(a) providing to a nucleic acid sample at least one circular probe (26) for each target sequence to be detected in the sample, whereby the probe has a first target specific section at its 5'-end (4) that is complementary to a first part of a target sequence (5) and a second target specific section at its 3'-end (6) that is complementary to a second part of the target sequence (7), whereby the first and second part of the target sequence are located adjacent to each other, and whereby the probe further comprises a tag section (8, 9) that is essentially non-complementary to the target sequence, whereby the tag section may comprise a stuffer sequence (10, 11) and whereby the tag section comprises at least one primer-binding sequence (12, 13);

(b) allowing the first and second target specific sections of the circular probe to anneal to the first and second parts of target sequences whereby the first and second target specific sections of the probe are annealed adjacent on the target sequence;

(c) providing means for connecting the first and second target specific sections annealed adjacently to the target sequence and allowing the first and second target specific sections to be connected, to produce a connected circular probe (28), corresponding to a target sequence in the sample;

(d) providing a primer pair comprising a first primer (16) that is complementary to a first primer-binding sequence (12), a polymerase enzyme and an optional second primer (17) that is complementary to a second primer-binding sequence (13);

(e) amplifying the resulting mixture to produce an amplified sample (19) comprising amplicons (20) that are linear representations of the connected circular probes;

(f) determining the presence or absence of a target sequence in a sample by detecting the presence or absence of the corresponding amplicon.

Probe

The circular oligonucleotide probe used in the present invention is a single linear oligonucleotide probe that is provided in step (a) for each target sequence in a sample. This single linear oligonucleotide probe combines the two target specific section into a single molecule that is circularised in step (c) when the annealed complementarity sections are connected. Thus, in the single linear probe the sections of target complementarity are each present at the extreme ends of the single linear probe. The complementarity sections at the extreme ends are intervened by the sequences that may serve as primer-binding sequences and may further be intervened by stuffer sequences of variable length. An example of such an arrangement of functional groups in the circular probe is: (target-complementarity section 1-stuffer sequence 1, primer-binding sequence 1-primer-binding sequence 2-stuffer sequence 2-target-complementarity section 2). The skilled person will appreciate that the circular probes are synthesised and applied in a linear form and that they will only be circular when the two complementary sections at the extreme ends of the probe are connected (ligated) annealing to the appropriate target sequence. Thus, the term "circular probe" as used herein actually refers to a linear molecule that is circularised by target sequence dependent connection (ligation). Only the term "connected circular probe" as used herein refers to a molecule in true circular form.

The complementary sections of the oligonucleotide probes are designed such that for each target sequence in a sample a probe is provided, preferably a specific probe, whereby the probes each contain a section at both their extreme ends that is complementary to a part of the target sequence and the corresponding complementary parts of the target sequence are located essentially adjacent to each other. Within a circular oligonucleotide probe, the oligonucleotide probe has a section at its 5'-end that is complementary to a first part of a target sequence and a section at its 3'-end that is complementary to a second part of the target sequence. Thus, when the circular probe is annealed to complementary parts of a target sequence the 5'-end of the oligonucleotide probe is essentially adjacent to the 3'-end of the oligonucleotide probe such that the respective ends of the probe may be ligated to form a phosphodiester bond and hence become a circular probe.

Circular probes are advantageous in the ligation step (c) because both target-complementarity sections are contained in the same molecule. Compared with conventional linear probes such as disclosed inter alia by WO97/45559, this means that there are equimolar amounts of the two target specific sections present and in each others vicinity. Such probes are more likely to hybridise to their respective target sequences because hybridisation of the first target-complementarity section to the target facilitates hybridisation of the second one and vice versa. In addition, the use of circular probes reduces the chances of the formation of incorrect ligation products that result from ligation between probes of different target sequences, due to the lower number of possible combinations of ligation products that can be formed when the first and second probes are part of the same circular molecule.

For more details regarding the characteristics, design and construction, use and advantages of padlock probes reference is made, inter alia, to the following documents: M. Nilsson et. al., "Padlock Probes: Circularizing Oligonucleotides for Localized DNA Detection," Science 265: 2085-88 (1994); Pickering et al. in Nucleic Acids Research, 2002, vol. 30, e60-U.S. Pat. No. 5,854,033; U.S. Pat. No. 5,912,124; WO 02/068683, WO 01/06012, WO 0077260, WO 01/57256 the contents of which are hereby incorporated by reference.

For each target sequence for which the presence or absence in a sample is to be determined, a specific oligonucleotide probe is designed with sections complementary to the adjacent complementary parts of each target sequence. Thus, in the method of the invention, for each target sequence that is present in a sample, a corresponding (specific) amplicon may be obtained in the amplified sample. Preferably, a multiplicity of oligonucleotide probes complementary to a multiplicity of target sequences in a sample is provided. An oligonucleotide probe for a given target sequence in a sample will at least differ in nucleotide sequence from probes for other target sequences, and will preferably also differ in length from probes for other targets, more preferably a probe for a given target will produce a connected probe and/or amplicon that differs in length from connected probes corresponding to other targets in the sample as described below. Alternatively, amplicons corresponding to different targets may have an identical length if they can be otherwise distinguished e.g. by different labels as described below.

Tag & Primer Binding Sites

The oligonucleotide probe further contains a tag that is essentially non-complementary to the target sequence. The tag does not or not significantly hybridise, preferably at least not under the above annealing conditions, to any of the target sequences in a sample, preferably not to any of the sequences in a sample. The tag preferably comprises at least one, preferably two primer-binding sites and may optionally comprises one or more stuffer sequences of variable length and/or a blocking section (see below).

Stuffers

The tag of the oligonucleotide probes may comprise one or more stuffer sequence of a variable length. The length of the stuffer varies from 0 to 500, preferably from 0 to 100, more preferably from 1 to 50. The length of the tag varies from 15 to 540, preferably from 18 to 140, more preferably from 20 to 75. The stuffer may be a unique sequence as is known as a Zip-code sequence as described by Iannone et al. (2000), Cytometry 39: pp. 131-140.

Blocking Section

In an alternative embodiment, the circular probe can contain a blocking section (27). The blocking section blocks primer elongation. The blocking section is preferably located between the two primer binding sites. Preferably the blocking section is located essentially adjacent to the 3'-end of the forward primer and essentially adjacent to the 5'-end of the reverse primer binding site, see also FIG. 14. An example of such an arrangement of functional groups in the circular probe is: (target-complementarity section 1-stuffer sequence 1, primer-binding sequence 1-blocking section-primer-binding sequence 2-stuffer sequence 2-target-complementarity section 2). This blocking section will effectively limit the primer elongation during amplification, thereby providing linear representations of the connected circular probes. Preferably the blocking section itself is located such between the two primer binding sites that the section is excluded from the amplification. The blocking section can comprise non-nucleotide polymers such as HEG (Hexaethylene glycol). If a blocking section is present, such as a HEG group, the DNA polymerase used may have a strand displacement activity as the blocking section will prevent the formation of long concatamers.

In an alternative embodiment, the ligated or connected circular probe comprising a blocking section can also be amplified using only one primer, preferably the forward primer. This amplification will result in the linear accumulation of amplicons with each amplification round. The circular probe in this case may contain one or more primer binding sites as long as only one primer is provided.

The blocking section can also be in the form of a recognition site for a restriction endonuclease. After ligation, the connected circular probe can be restricted with a suitable restriction endonuclease to provide linearised connected circular probes. To facilitate restriction a suitable oligonucleotide can be provided to locally generate a double stranded sequence that can be restricted using a restriction endonuclease. The connected circular probe is preferably restricted prior to the amplification step.

The advantage associated with the restriction of the circular probe prior to the amplification step is that, in the case that the polymerase has a strand displacement activity, whether residual or not, the formation of (long) concatamers is prevented. The absence or reduced presence of (long) concatamers is advantageous in length based separation such as preferably used in the detection step of the present invention as the resulting sample to be detected contains oligonucleotides with a length in a pre-determined size range. This increases the high throughput capacity as it reduces the time period between the subsequent analysis of more than one sample. A sample comprising ligated circular probes that is restricted incompletely, i.e. circularised probes remain present in the sample does not significantly, or only to a reduced extent, influence the detection step. More in particular, remaining circular probes in the sample do not or to a lesser extent influence the separation time (23) between consecutively injected samples in the way that a (long) concatamer does when a post-amplification restriction step is performed incompletely. Another advantage is that the amplification of short strands is generally more reliable than the formation of long strands. To amplify a multitude of short strands to generate amplicons is more reliable and quicker in general than the generation of one long concatamer. This attributes to an increased reliability of the method of the invention in a high through put fashion. These linearised connected circular probes can subsequently be amplified, essentially as described hereinbefore, using one or two primers. The restriction endonuclease can be any restriction endonuclease. Preferably it is a simple and cheap endonuclease such as MseI. It is preferred that the sequence of the oligonucleotide probe does not contain any further restriction sites for this endonuclease. An alternative is the incorporation of at least one RNA at the position of the blocking section and subsequent restriction with an RNAse.

Generating linear representations of the connected circular probes, the amplicons, the problem of long concatamers can be overcome, rendering the method suitable for true high throughput electrophoretic technologies. By amplification of only short strands of oligonucleotides, using the blocking section as described hereinabove or by using at least one primer in combination with a polymerase lacking in strand displacement activity, a set of amplicons representing a sample can be obtained wherein the amplicons are of a discrete length within a predetermined range, based on the design of the probes. Subsequent loading on a electrophoretic device will result in the swift separation of the amplicons.

Hybridisation

In step (a) a multiplicity of different target sequences, i.e. at least two different target sequences, is brought into contact with a multiplicity of specific oligonucleotide probes under hybridising conditions. The oligonucleotide probes are subsequently allowed to anneal to the adjacent complementary parts of the multiple target sequences in the sample. Methods and conditions for specific annealing of oligonucleotide probes to complementary target sequences are well known in the art (see e.g. in Sambrook and Russel (2001) "Molecular Cloning: A Laboratory Manual ($3^{rd}$ edition), Cold Spring Harbor Laboratory, Cold Spring Harbor Laboratory Press). Usually, after mixing of the oligonucleotide probes and target sequences the nucleic acids are denatured by incubation (generally at between 94° C. and 96° C.) for a short period of time (e.g. 30 seconds to 5 minutes) in a low salt buffer (e.g. a buffer containing no salts or less salts than the ionic strength equivalent of 10 mM NaCl). The sample containing the denatured probes and target sequences is anthen allowed to cool to an optimal hybridisation temperature for specific annealing of the probes and target sequences, which usually is about 5° C. below the melting temperature of the hybrid between the complementary section of the probe and its complementary sequence (in the target sequence). In order to prevent aspecific or inefficient hybridisation of one of the two probe sections, or in a sample with multiple target sequences, it is preferred that, within one sample, the sections of the probes that are complementary to the target sequences are of a similar, preferably identical melting temperatures between the different target sequences present in the sample. Thus, the complementary sections of the probes preferably differ less than 20, 15, 10, 5, or 2° C. in melting temperature. This is facilitated by using complementary sections of the probes with a similar length and similar G/C content. Thus, the complementary sections preferably differ less than 20, 15, 10, 5, or 2 nucleotides in length and their G/C contents differ by less than 30, 20, 15, 10, or 5%. Complementary as used herein means that a first nucleotide sequence is capable of specifically hybridising to second nucleotide sequence under normal stringency conditions. A nucleotide sequence that is considered complementary to another nucleotide sequence may contain a minor amount, i.e. preferably less than 20, 15, 10, 5 or 2%, of mismatches. Alternatively, it may be necessary to compensate for mismatches e.g. by incorporation of so-called universal nucleotides, such as for instance described in EP-A 974 672, incorporated herein by reference or by the use of suitable locked nucleic acids (LNAs) and peptide nucleic acids (PNAs). Since annealing of probes to target sequences is concentration dependent, annealing is preferably performed in a small volume, i.e. less than 10 μl. Under these hybridisation conditions, annealing of probes to target sequences usually is fast and does not to proceed for more than 5, 10 or 15 minutes, although longer annealing time may be used as long as the hybridisation temperature is maintained to avoid aspecific annealing.

In a preferred embodiment of the invention, excellent results have been obtained by prolonged hybridisation times such as overnight hybridisation or for more than one hour. Prolonged hybridisation times can be advantageous in these assays as the difference in signal due to different hybridisation efficiencies is reduced and it is considered desirable to achieve complete hybridisation and ligation of all probes for which a target sequence is present. Excellent results have been obtained by a combined hybridisation-ligation step using a thermostable ligase described herein. In this embodiment the hybridisation-ligation was performed by allowing the probes to hybridise during 1 hour in the presence of a thermostable ligase, followed by a denaturation step. Repeating these steps for at least 2 times provided good results. Repeating these steps 10 times provided excellent results.

To avoid evaporation during denaturation and annealing, the walls and lids of the reaction chambers (i.e. tubes or microtitre wells) may also be heated to the same temperature as the reaction mixture. In preferred oligonucleotide probes the length of the complementary section is preferably at least 15, 18 or 20 nucleotides and preferably not more than 30, 40, or 50 nucleotides and the probes preferably have a melting temperature of at least 50° C., 55° C. or 60° C.

Non-Hybridised Probes

The probes that are not complementary to a part of the target sequence or that contain too many mismatches will not or only to a reduced extent hybridise to the target sequence when the sample is submitted to hybridisation conditions. Accordingly ligation is less likely to occur. The number of spurious ligation products from these probes in general will therefore not be sufficient and much smaller than the bonafide ligation products such that they are outcompeted during subsequent multiplex amplification. Consequently, they will not be detected or only to a minor extent.

Ligation

The respective 5'- and 3'-ends of the oligonucleotide probe that are annealed essentially adjacent to the complementary parts of a target sequence are connected in step (c) to form a covalent bond by any suitable means known in the art. The ends of the probes may be enzymatically connected in a phosphodiester bond by a ligase, preferably a DNA ligase. DNA ligases are enzymes capable of catalysing the formation of a phosphodiester bond between (the ends of) two polynucleotide strands bound at adjacent sites on a complementary strand. DNA ligases usually require ATP (EC 6.5.1.1) or NAD (EC 6.5.1.2) as a cofactor to seal nicks in double stranded DNA. Suitable DNA ligase for use in the present invention are T4 DNA ligase, *E. coli* DNA ligase or preferably a thermostable ligase like e.g. *Thermus aquaticus* (Taq) ligase, *Thermus thermophilus* DNA ligase, or *Pyrococcus* DNA ligase. Alternatively, chemical autoligation of modified polynucleotide ends may be used to ligate two oligonucleotide probes annealed at adjacent sites on the complementary parts of a target sequence (Xu and Kool, 1999, Nucleic Acid Res. 27: 875-881).

Both chemical and enzymatic ligation occur much more efficient on perfectly matched probe-target sequence complexes compared to complexes in which one or both of the ends of the probe form a mismatch with the target sequence at, or close to the ligation site (Wu and Wallace, 1989, Gene 76: 245-254; Xu and Kool, supra). In order to increase the ligation specificity, i.e. the relative ligation efficiencies of perfectly matched oligonucleotides compared to mismatched oligonucleotides, the ligation is preferably performed at elevated temperatures. Thus, in a preferred embodiment of the invention, a DNA ligase is employed that remains active at 50-65° C. for prolonged times, but which is easily inactivated at higher temperatures, e.g. used in the denaturation step during a PCR, usually 90-100° C. One such DNA ligase is a NAD requiring DNA ligase from a Gram-positive bacterium (strain MRCH 065) as known from WO 01/61033. This ligase is referred to as "Ligase 65" and is commercially available from MRC Holland, Amsterdam.

Gap Ligation

In an alternative embodiment, for instance directed to the identification of indels, the respective ends may be annealed such that a gap is left. This gap can be filled with a suitable oligonucleotide and ligated. Such methods are known in the art as 'gap ligation' and are disclosed inter alia in WO 00/77260. Another possibility to fill this gap is by extension of one end of the probe using a polymerase and a ligase in combination with single nucleotides, optionally preselected from A, T, C, or G, or di-, tri- or other small oligonucleotides.

Primers

The connected probes are amplified using a pair of primers corresponding to the primer-binding sites. In a preferred embodiment at least one of the primers or the same set of primers is used for the amplification of two or more different connected probes in a sample, preferably for the amplification of all connected probes in a sample. Such a primer is sometimes referred to as a universal primer as these primers are capable of priming the amplification of all probes containing the corresponding universal primer binding site and consequently of all ligated probes containing the universal primer binding site. The different primers that are used in the amplification in step (d) are preferably essentially equal in annealing and priming efficiency. Thus, the primers in a sample preferably differ less than 20, 15, 10, 5, or 2° C. in melting temperature. This can be achieved as outlined above for the complementary section of the oligonucleotide probes. Unlike the sequence of the complementary sections, the sequence of the primers is not dictated by the target sequence. Primer sequences may therefore conveniently be designed by assembling the sequence from tetramers of nucleotides wherein each tetramer contains one A, T, C and G or by other ways that ensure that the G/C content and melting temperature of the primers are identical or very similar. The length of the primers (and corresponding primer-binding sites in the tags of the probes) is preferably at least 12, 15 or 17 nucleotides and preferably not more than 25, 30, 40 nucleotides.

In a preferred embodiment, at least two of the oligonucleotide probes that are complementary to at least two different target sequences in a sample comprise a tag sequence that comprises a primer-binding site that is complementary to a single primer sequence. Thus, preferably at least one of the first and second primer in a primer pair is used for the amplification of connected probes corresponding to at least two different target sequences in a sample, more preferably for the amplification of connected probes corresponding to all target sequences in a sample. Preferably only a single first primer is used and in some embodiments only a single first and a single second primer is used for amplification of all connected probes. Using common primers for amplification of multiple different fragments usually is advantageous for the efficiency of the amplification step.

The connected probes obtained from the ligation of the adjacently annealed probe sections are amplified in step (d), using a primer set, preferably consisting of a pair of primers for each of the connected probes in the sample. The primer pair comprises primers that are complementary to primer-binding sequences that are present in the connected probes. A primer pair usually comprises a first and at least a second primer, but may consist of only a single primer that primes in both directions. Excellent results have been obtained using primers that are known in the art as AFLP—primers such as described inter alia in EP534858 and in Vos et al., Nucleic Acid Research, 1995, vol. 23, 4407-44014.

Selective Primers

In a particular preferred embodiment, one or more of the primers used in the amplification step of the present invention is a selective primer. A selective primer is defined herein as a primer that, in addition to its universal sequence which is complementary to a primer binding site in the probe, contains a region that comprises so-called "selective nucleotides". The region containing the selective nucleotides is located at the 3'-end of the universal primer.

The principle of selective nucleotides is disclosed inter alia in EP534858 and in Vos et al., Nucleic Acid Research, 1995, vol. 23, 4407-44014. The selective nucleotides are complementary to the nucleotides in the (ligated) probes that are located adjacent to the primer sequence. The selective nucleotides generally do not form part of the region in the (ligated) probes that is depicted as the primer sequence. Primers containing selective nucleotide are denoted as +N primers, in which N stands for the number of selective nucleotides present at the 3'-end of the primer. N is preferably selected from amongst A, C, T or G.

N may also be selected from amongst various nucleotide alternatives, i.e. compounds that are capable of mimicking the behavior of ACTG-nucleotides but in addition thereto have other characteristics such as the capability of improved hybridisation compared to the ACTG-nucleotides or the capability to modify the stability of the duplex resulting from the hybridisation. Examples thereof are PNA's, LNA's, inosine etc. When the amplification is performed with more than one primer, such as with PCR using two primers, one or both primers can be equipped with selective nucleotides. The number of selective nucleotides may vary, depending on the species or on other particulars determinable by the skilled man. In general the number of selective nucleotides is not more than 10, but at least 5, preferably 4, more preferably 3, most preferred 2 and especially preferred is 1 selective nucleotide.

A +1 primer thus contains one selective nucleotide, a +2 primer contains 2 selective nucleotides etc. A primer with no selective nucleotides (i.e. a conventional primer) can be depicted as a +0 primer (no selective nucleotides added). When a specific selective nucleotide is added, this is depicted by the notion +A or +C etc.

By amplifying a set of (ligated) probes with a selective primer, a subset of (ligated) probes is obtained, provided that the complementary base is incorporated at the appropriate position in the desired of the probes that are supposed to be selectively amplified using the selective primer. Using a +1 primer, for example, the multiplex factor of the amplified mixture is reduced by a factor 4 compared to the mixture of ligated probes prior to amplification. Higher reductions can be achieved by using primers with multiple selective nucleotides, i.e. 16 fold reduction of the original multiplex ration is obtained with 2 selective nucleotides etc.

When an assay is developed which, after ligation, is to be selectively amplified, it is preferred that the probe contains the complementary nucleotide adjacent to the primer binding sequence. This allows for pre-selection of the ligated probe to be selectively amplified.

The use of selective primers in the present invention has proven to be advantageously when developing ligation based assays with high multiplex ratios of which subsequently only a specific part needs to be analyzed resulting in further cost reduction of the ligation reaction per datapoint. By designing primers together with adjacent selective nucleotides, the specific parts of the sample that are to be amplified separately can be selected beforehand.

One of the examples in which this is useful and advantageous is in case of analysis of samples that contain only minute amounts of DNA and/or for the identification of different (strains of) pathogens. For example, in an assay directed to the detection of various strains of anthrax (*Bacillus anthracis*), for each of the strains a set of representative probes is designed. The detection of the presence or absence of this set (or a characterizing portion thereof) of ligated probes after the hybridisation and ligation steps of the method of the invention may serve as an identification of the strain concerned. The selective amplification with specifically designed primers (each selective primer is linked to a specific strain) can selectively amplify the various strains, allowing their identification. For instance, amplification with an +A primer selectively amplifies the ligated probes directed to strain X where a +G primer selectively amplifies the ligated probes directed to strain Y. If desired, for instance in the case of small amounts of sample DNA, an optional first amplification with a +0 primer will increase the amount of ligated probes, thereby facilitating the selective amplification.

For example, a universal primer of 20 nucleotides becomes a selective primer by the addition of one selective nucleotide at its 3' end, the total length of the primer now is 21 nucleotides. See also FIG. 15. Alternatively, the universal primer can be shortened at its 5' end by the number of selective nucleotides added. For instance, adding two selective nucleotides at the 3'end of the primer sequence can be combined with the absence (or removal) of two nucleotides from the 5'end of the universal primer, compared to the original universal primer. Thus a universal primer of 20 nucleotides is replaced by a selective primer of 20 nucleotides. These primers are depicted as 'nested primers' throughout this application. The use of selective primers based on universal primers has the advantage that amplification parameters such as stringency and temperatures may remain essentially the same for amplification with different selective primers or vary only to a minor extent. Preferably, selective amplification is carried out under conditions of increased stringency compared to non-selective amplification. With increased stringency is meant that the conditions for annealing the primer to the ligated probe are such that only perfectly matching selective primers will be extended by the polymerase used in the amplification step. The specific amplification of only perfectly matching primers can be achieved in practice by the use of a so-called touchdown PCR profile wherein the temperature during the primer annealing step is stepwise lowered by for instance 0.5° C. to allow for perfectly annealed primers. Suitable stringency conditions are for instance as described for AFLP amplification in EP 534858 and in Vos et al., Nucleic Acid Research, 1995, vol. 23, 4407-44014. The skilled man will, based on the guidance find ways tot adapt the stringency conditions to suit his specific need without departing from the gist of the invention.

One of the further advantages of the selective amplification of ligated probes is that an assay with a high multiplex ratio can be adapted easily for detection with methods or on platforms that prefer a lower multiplex ratio.

One of many examples thereof is the detection based on length differences such as electrophoresis and preferably capillary electrophoresis such as is performed on a MegaBACE or using nano-technology such as Lab-on-a-Chip.

Amplification

In step (d) of the method of the invention, the connected probes are amplified to produce (detectable) amplified connected probes (amplicons) that are linear representations of the connected circular probes by any suitable nucleic acid amplification method known in the art. Nucleic acid amplification methods usually employ two primers, dNTP's, and a (DNA) polymerase. A preferred method for amplification is PCR. "PCR" or "Polymerase Chain Reaction" is a rapid procedure for in vitro enzymatic amplification of a specific DNA segment. The DNA to be amplified is denatured by heating the sample. In the presence of DNA polymerase and excess deoxynucleotide triphosphates, oligonucleotides that hybridise specifically to the target sequence prime new DNA synthesis. It is preferred that the polymerase is a DNA polymerase that does not express strand displacement activity or at least not significantly. Examples thereof are Amplitaq and Amplitaq Gold (supplier Perkin Elmer) and Accuprime (Invitrogen). One round of synthesis results in new strands of determinate length, which, like the parental strands, can hybridise to the primers upon denaturation and annealing. The second cycle of denaturation, annealing and synthesis produces two single-stranded products that together compose a discrete double-stranded product, exactly the length between the primer ends. This discrete product accumulates exponentially with each successive round of amplification. Over the course of about 20 to 30 cycles, many million-fold amplification of the discrete fragment can be achieved. PCR protocols are well known in the art, and are described in standard laboratory textbooks, e.g. Ausubel et al., Current Protocols in Molecular Biology, John Wiley & Sons, Inc. (1995). Suitable conditions for the application of PCR in the method of the invention are described in EP-A 0 534 858 and Vos et al. (1995; Nucleic Acids Res.23: 4407-23:4407-4407-4407-4414), where multiple DNA fragments between 70 and 700 nucleotides and containing identical primer-binding sequences are amplified with near equal efficiency using one primer pair. Other multiplex and/or isothermal amplification methods that may be applied include e.g. LCR, self-sustained sequence replication (3SR), Q-β-replicase mediated RNA amplification, or strand displacement amplification (SDA). In some instances this may require replacing the primer-binding sites in the tags of the probes by a suitable (RNA) polymerase-binding site as long as they lead to linear amplification products as defined herein before, i.e. of discrete lengths and corresponding to the length of the circular probes.

As described herein, linear representations of the connected circular probes can be obtained by exponential amplification of the circular probe with two primers, one forward and one reverse, using a polymerase that does not or not significantly have a strand displacement activity. The first primer elongation in the amplification with the forward primer generates an oligonucleotide product until the 5'end of the forward primer is reached. There the primer elongation is terminated, due to the substantial absence of strand displacement activity of the polymerase used, leaving a elongated primer with substantially the same length as the connected circular probe. The second cycle of denaturation, primer hybridisation and primer elongation will, for the forward primer, produce the identical strand as during the first primer elongation, while the reverse primer will hybridise to the oligonucleotide product from the elongation of the first primer elongation and thereby produce the complementary strand, resulting in the exponential amplification of the circular probe to thereby produce amplicons of discrete length which are representations of the connected circular oligonucleotide probes.

Amplicons

The term 'amplicon' as used herein refers to the product of the amplification step of the connected or ligated probe. The term 'amplicon' as used herein thus refers to an amplified connected probe. After the ligation step wherein the two target specific section are connected by mean of a ligase, the connected or ligated probe is combined with one or more primers and a polymerase and amplified. The ligated probe, the primers, the polymerase and/or other parameters and variables are such that the amplification results in linear representations of the circular probe. In the present invention the amplicon is a linear oligonucleotide having a length that does not substantially exceed the length of the circular probe. The minimum length of the amplicon is at least the sum of the length of the two target complementary sections. It is preferred that the length of the amplicon corresponds to the length of the circular probe. It is more preferred that the length of the amplicon is indicative of the ligation of the corresponding circular probe. Preferably an amplicon does not contain repetitions of sections of the circular probe, i.e. is not a concatamer or a multimer of the circular probe or a multimeric representation thereof. Preferably an amplicon is a linear and monomeric representation of the connected circular probe.

The advantage obtained by the conversion from circular probes to linear amplicons is that the advantageous characteristics of the circular probe are used (improved kinetics, increased hybridisation to the target strand due to the formation of the 'padlock' conformation), while the resulting amplicons are of a discrete length an can be detected subsequently without the need for additional steps such as restriction and labelling. FIG. 14 displays a schematic representation of circular probes and amplicons. The various embodiments of the present invention will provide further detail in this respect.

Detection

Detection of the labelled separated samples is performed by a detector to result in detection data. The detector is of course dependent on the general system on which the separation is carried out (capillary electrophoresis, slab-gel electrophoresis, fixed detector-continuous gel-electrophoresis) but is also depending on the label that is present on the primer, such as a fluorescent or a radioactive label.

The amplicons in a sample are preferably analysed on an electrophoretic device. The electrophoretic device preferably separates the different amplicons in an amplified sample on the basis of length, after which the separated amplicons may be detected as described below. A suitable electrophoretic device may be a gel-electrophoresis device, e.g. for conventional (polyacrylamide) slab gel-electrophoresis, or a capillary electrophoresis device such as exemplified by the MegaBACE equipment available from Molecular Dynamics Amersham-Biosciences. An alternative is the nano-sized capillary electrophoretic devices known as Lab-on-a-Chip. The electrophoretic device preferably is a multichannel device in which multiple samples are electrophoresed in multiple channels in parallel. The electrophoretic device has an application location (per channel) for application (loading) of the amplified sample to be electrophoresed, a separation area over which the fragments in the sample migrate by electrophoresis, and preferably also a detection device located at a detection location distal from the application location. The detection device will usually comprises a photomultiplier for the detection of fluorescence, phosphorescence or chemiluminescence. Alternatively, in the case of gel-electrophoresis, the separated fragments may be detected in the gel e.g. by autoradiography or fluorography.

Length Discrimination

To discriminate between different target sequences in the sample preferably a difference in length of the respective corresponding amplicons is used. By separating the amplicons based on length, the presence of the corresponding target nucleotides sequences in the sample can be determined. Accordingly, in a preferred embodiment of the present invention, the discrimination between amplicons derived from different target sequences in a sample is based on a length difference between the respective amplicons corresponding to different target sequences in a sample or amplified sample.

Preferably, the length difference is provided by the length of the stuffer sequence(s) in the oligonucleotide probes. By including in each oligonucleotide probe a stuffer of a predetermined length, the length of each amplicon in an amplified sample can be controlled such that an adequate discrimination based on length differences of the amplicon obtained in step (d) is enabled. In a preferred embodiment of a probe according to the invention, the stuffer is located between the probe's section complementary to the target sequence and a primer-binding sequence. As there are two target specific sections at both ends of the probe and two primer binding sites, two stuffer can be incorporated in the probe therein between. As such, the total length of the stuffer is provided by the combination of the length of the first stuffer and second stuffer in the probe. Accordingly, in a preferred embodiment, the oligonucleotide probe comprises two stuffers, preferably in the non target complementary tags. A graphic representation thereof can be found in FIG. 14.

The length differentiation between amplicons obtained from target sequences in the sample is preferably chosen such that the amplicons can be distinguished based on their length. This is accomplished by using stuffer sequences or combinations of stuffer sequences which (together) result in clear length differences that may be distinguished on electrophoretic devices. Thus, from the perspective of resolving power, the length differences between the different amplicons, as may be caused by their stuffers, are as large as possible. However, for several other important considerations, as noted before, the length differences between the different amplicon is preferably as small as possible: (1) the upper limit that exists in practice with respect to the length of chemically synthesised probes of about 100-150 bases at most; (2) the less efficient amplification of larger fragments, (3) the increased chances for differential amplification efficiencies of fragments with a large length variation; and (4) the use of multiple injections of detection samples on the detection device which works best with fragments in a narrow length range. Preferably the length differences between the sequences to be determined and provided by the stuffers is at least sufficient to allow discrimination between essentially all amplicons. By definition, based on chemical, enzymatic and biological nucleic acid synthesis procedures, the minimal useable size difference between different amplicon in an amplified sample is one base, and this size difference fits within the resolving power of most electrophoresis devices, especially in the lower size ranges. Thus based on the above it is preferred to use multiplex assays with amplification products with differ in length by a single base(pair). In a preferred embodiment, the length difference between different amplicons in an amplified sample is at least two nucleotides. In a particularly preferred embodiment of the invention the amplicon corresponding to different target sequences in a sample have a length difference of two nucleotides.

Labels

In a preferred embodiment, at least one of the primers complementary to the primer-binding sites of the first and second oligonucleotide probes in the sample comprises a label, preferably the second primer comprises a label. The label can be selected from a large group, amongst others comprising fluorescent and/or phosphorescent moieties such as dyes, chromophores, or enzymes, antigens, heavy metals, magnetic probes, phosphorescent moieties, radioactive labels, chemiluminescent moieties or electrochemical detecting moieties. Preferably the label is a fluorescent or phosphorescent dye, more preferably selected from the group of FAM, HEX, TET, JOE, NED, and (ET-)ROX. Dyes such as FITC, Cy2, Texas Red, TAMRA, Alexa fluor 488™, Bodipy™ FL, Rhodamine 123, R6G, Bodipy 530, Alexafluor™532 and IRDyes™ by Licor as used on the NEN Glober IR$^2$ platform are also suitable for use in the present invention. Preferably the label may be chosen from amongst the fluorescent or phosphorescent dyes in the group consisting of FAM, TET, JOE, NED, HEX, (ET-)ROX, FITC, Cy2, Texas Red, TAMRA, Alexa fluor 488™, Bodipy™ FL, Rhodamine 123, R6G, Bodipy 530, Alexafluor™532 and IRDyes™.

By using a primer set comprising differently labelled primers, the number of connected probes that can be discriminated in a sample and hence the number of target sequences in a sample can be doubled for each additional label. Thus, for each additional label that is used in a sample, the number of target sequences that can be analysed in a sample is doubled. The maximum number of labels that can be used in one sample in a high throughput method is governed mostly by the limitations in the detection capabilities of the available detection platforms. At present, one of the most frequently used platforms (MegaBACE, by Molecular Dynamics—Amersham-Biosciences Ltd. allows the simultaneous detection of up to four fluorescent dyes, being FAM, JOE or HEX, NED and (ET-)ROX. However, alternative capillary electrophoresis instruments are also suitable, which includes ABI310, ABI3100, ABI3700 (Perkin-Elmer Corp.), CEQ2000 XL (Beckman Coulter) and others. Non-limiting examples of slab-gel based electrophoresis devices include ABI377 (Perkin Elmer Corp.) and the global IR$^2$ automated DNA sequencing system, available from LI-COR, Lincoln, Nebr., USA.

Length and Label

Throughput can be increased by the use of multiple labelled primers. One of the problems associated with the use of different labels in one sample is cross talk or residual cross talk. Cross talk or residual cross talk, as used herein, refers to the overlap between the emission spectra of different (fluorescent) labels. For instance when fluorescent dyes are used, each dye has a different emission (and absorption) spectrum. In case of two dyes in one sample, these spectra can overlap and may cause a disturbance of the signal, which contravenes the quality of the data obtained. Particularly when two nucleotide fragments to be detected in a sample are labelled with a different label and one of the fragments is present in an abundant amount whereas the other is present only in minute amounts, residual cross talk can cause that the measured signal of the fragment that is present in only minute amounts is mostly derived from the emission of another label with an overlapping emission spectrum that is abundantly contained in a fragment with identical size of another sample. The reciprocal effect of the other dye may also occur but in this example its effect is probably less because of the abundance differences between the amplicons labelled with the respective dyes.

Chehab et al. (Proc. Natl. Acad. Sci. USA, 86:9178-9182 (1989) have attempted to discriminate between alleles by attaching different fluorescent dyes to competing alleles in a single reaction tube by selecting combinations of labels such that the emission maximum of one dye essentially coincides with the emission minimum of the other dye. However, at a certain wavelength at which one dye expresses an absorption maximum, there is always also some remaining absorption from another dye present in the sample, especially when the sample contains multiple dyes.

This route to multiplex analysis was found to be limited in scale by the relatively few dyes that can be spectrally resolved. One of the major problems with the use of multiple dyes is that the emission spectra of different fluorescent labels often overlap. The resulting raw data signals have to be corrected for the contribution of similar size fragments that are detected simultaneously and are labelled with another fluorescent dye by a process called cross-talk correction. Cross-talk correction is commonly carried out by mathematical means, based on the known theoretical absorption spectra for both dyes, after "raw" data collection from the detection device. Mathematical correction is based on theoretical spectra and ignores that emission spectra of labels are sensitive and often affected by the composition of the detection sample. These sensitivities can affect the brightness and/or the wavelength of the emission. This means that parameters such as pH, temperature, excitation light intensity, non-covalent interactions, salt concentration and ionic strength strongly influence the resulting emission spectrum. In particular, it is known that the presence of residual salts in a sample affects the fluorescence signal emitted by the dye and is a critical factor in case of detection by capillary electrophoresis using electrokinetic injection because it then also affects the injection efficiency. Thus, spectral overlap is a potential source of error that negatively impacts on data quality in case of multiplex detection using different fluorescent dyes.

The present invention provides for a solution to this problem such that two (or more) labels with overlapping spectra can be used in the same sample without significantly affecting data quality. By a predetermined combination of length differences and labels, an increase in the number of target nucleotide sequences that can be detected in sample is obtained while the quality of the data remains at least constant. In a preferred embodiment of the invention, spectral overlap between two differently labelled sequences is reduced by the introduction of a length difference between the two sequences. This label-related length difference can be provided for by the length of the stuffer sequence as described herein. The number of different labels that can be used in the same sample in the present method is at least two, preferably at least three, more preferably at least four. The maximum number of labels is functionally limited by the minimum of spectral overlap that remains acceptable, which for most applications typically amounts to less than 15 percent of the true signal, preferably less than 10 percent, more preferably lees than 5 percent and most preferably less than 1 percent of the true signal.

In order to avoid the potential influence of residual cross-talk on the data quality in case different samples are labelled with multiple fluorescent dyes with overlapping emission spectra and fragments with identical length are detected simultaneously in the same run, in a particular preferred embodiment it is preferred to choose the stuffer sequences such that amplicons differ by at least two base pairs within a multiplex set and differ by a single base pair between multiplex sets labelled with the different dyes that have overlapping spectra. By doing so, the length of the fragments labelled with the respective dyes can be chosen such that the potential influence of residual cross-talk on the quality of the data is circumvented because unique combinations of fragments size and labelling dye are defined (FIG. 3).

A particular preferred embodiment of the invention is directed to a method in which a sample comprising amplicons is derived from a multiplicity of target sequences. These amplicons are differently labelled, thereby defining groups of amplicons carrying the same label. Within each group, the stuffer provided for a length difference of at least two, preferably two nucleotides. Between two groups with labels having spectral overlap, the stuffer provides a length difference of one nucleotide, effectively resulting in one group having an even number of nucleotides and one group having an odd number of nucleotides as described above.

In one aspect the present invention pertains to a method for the improved discrimination and detection of target sequences in a sample, comprising providing at least a two or more groups of oligonucleotide probes, wherein the amplicons obtained with different groups of oligonucleotide probes have different labels, wherein substantially each amplified connected probe target sequence within a group has the same label, wherein within a group of identically labelled amplicons a length difference is provided between each identically labelled probe within that group, wherein between the first and second group an additional length difference is provided such that each amplified connected probe in the amplified sample is characterised by a combination of length of the sequence and the label.

In a preferred embodiment of the method of the invention, at least two groups of oligonucleotide probes are provided to a sample, whereby each group of oligonucleotide probes has tag sequences with at least one group specific primer-binding site. The connected probes of each group are amplified from a primer pair wherein at least one of the first and second primers is complementary to the group specific primer-binding site, and whereby at least one of the first and second primers of a group comprises a group specific label. In each group, an amplicon corresponding to a target sequence in the sample differs in length from an amplicon corresponding to a different target sequence in the sample. The group specific labels are preferably such that the detection device can distinguish between the different group specific labels. The length difference is preferably provided by the length of the stuffer sequence. Preferably in this embodiment of the method of the invention, a first part of the groups has amplicons having an even number of nucleotides and a second part of the groups has amplicons having an odd number of nucleotides. Preferably, the groups of amplicons having an even number of nucleotides and the groups amplicons having an odd number of nucleotides are labelled with (fluorescent) labels, which have the least overlap in their emission spectra. Thus, two groups of amplicons, each group having an odd number of nucleotides are labelled with labels, which have the least overlap in their emission spectra. The same holds for two groups of amplicons, each group having an even number of nucleotides. Two groups of amplicons, one group having an odd number of nucleotides and the other group having an even number of nucleotides are labelled with labels that have a larger overlap in their emission spectra. The relative notions as used herein of 'the least overlap in their emission spectra' and 'have a larger overlap in their emission spectra' refer to a group of labels from which a selection of the labels can be made for use in the present invention. This group of labels may depend on the detection platform used to other factors such as those disclosed herein before. In a particularly preferred embodiment of this method, a first and second groups of amplicons having an even number of nucleotides are produced and a third and fourth group of connected amplified probes having an odd number of nucleotides are produced and whereby the first and second group are labelled with FAM and NED, respectively, and the third and fourth group are labelled with (ET-)ROX and either JOE or HEX, respectively; or vice versa, whereby the first and second group are labelled with (ET-)ROX and either JOE or HEX, respectively, and the third and fourth group are labelled with FAM and NED, respectively. Thus, in these embodiments, the fluorescent labels are chosen such that the groups of amplicons that co-migrate, because they both contain fragments with either even or odd numbers of nucleotides, have labels which have the least overlap in their emission spectra, thereby avoiding as much as possible cross-talk in the detection of amplicons in different groups (see also below).

In a preferred embodiment to avoid cross-talk it is therefore desirable to combine a difference in length with a different label when analysing a set of amplicons in such a way that the influence of spectral overlap on the data quality is avoided by length differences between the amplicons labelled with the dyes that have overlapping emission spectra.

It is preferred that in each sample the connected probes derived from each target sequence differ from any other connected probe in the sample in length, and/or in the label or, preferably in the combination of the length and the label. To provide for an adequate separation of the amplicons of different length it is preferred that the length difference between two different connected probes is at least two nucleotides, preferably two. When detecting polymorphisms it is preferred that the difference in length between two or more (SNP) alleles of the polymorphism is not more than two, thereby ensuring that the efficiency of the amplification is similar between different alleles or forms of the same polymorphism. This implies that preferably both alleles are amplified with the same pair of primers and hence will be labelled with the same dye.

In a preferred embodiment, for example directed to the detection of different alleles of a multiplicity of loci, the distribution between odd/even lengths within a group can be designed in the following way. Two loci L1, L2 are each represented by two alleles A11, A12 for L1 and A21, A22 for L2. The lengths of the various alleles (or ligated and amplified probes representing those alleles) is such that A11>A12>A21>A22; A12-A11=2; A22-A21=2; A12-A21=3. Between groups G1 and G2 carrying labels that may have an overlap in their spectra there can be a length difference of 1 nucleotide. Thus G1(A11)-G2(A11)=1, hence the group starts with either an even or an uneven length.

This distribution has some significant advantages compared to the more densely packed distribution disclosed herein. It is known that due to conformational differences that different sequences of identical length generally differ in their electrophoretic mobility. When there is only a difference in length of one nucleotide, this may cause overlap between the peaks if the sequences are of a very different mobility. For instance the difference in mobility between two alleles of one locus (A11, A12), will be less than the difference in mobility between two alleles from different loci (A12, A21). When there is a significant difference in mobility between A12 and A21, this may lead to unreliable detection. By creating length distributions as herein disclosed this can be avoided. The lower throughput is then weighed against the reliability of the detection.

The problem of the overlap between the spectra of the different labels is then adequately avoided. This is schematically depicted in Table A.

TABLE A

Alternative distribution scheme of labels and lengths of probes.

| Length | Group 1-Label 1 | Group 2-Label 2 | Group 3-Label 3 | Group 4-Label 4 |
|---|---|---|---|---|
| N | G1A11 | | G3A11 | |
| N + 1 | | G2A11 | | G4A11 |

TABLE A-continued

Alternative distribution scheme of labels and lengths of probes.

| Length | Group 1-Label 1 | Group 2-Label 2 | Group 3-Label 3 | Group 4-Label 4 |
|---|---|---|---|---|
| N + 2 | G1A12 | | G3A12 | |
| N + 3 | | G2A12 | | G4A12 |
| N + 4 | | | | |
| N + 5 | G1A21 | | G3A21 | |
| N + 6 | | G2A21 | | G4A21 |
| N + 7 | G1A22 | | G3A22 | |
| N + 8 | | G2A22 | | G4A22 |
| N + 9 | | | | |
| N + 10 | G1A31 | | G3A31 | |
| N + 11 | | G2A31 | | G4A31 |
| N + 12 | G1A32 | | G3A32 | |
| N + 13 | | G2A32 | | G4A32 |
| N + 14 | | | | |
| N + 15 | G1A41 | | G3A41 | |
| N + 16 | | G2A41 | | G4A41 |
| N + 17 | G1A42 | | G3A42 | |
| N + 18 | | G2A42 | | G4A42 |

In an embodiment of the present invention there is provided between the amplicons within one group, a length difference of alternating two and three nucleotides, i.e. 0, 2, 5, 7, 10, 12 etc. The other group then has a length difference of 1, 3, 6, 8, 11, 13 etc.

Target Sequences

In its widest definition, the target sequence may be any nucleotide sequence of interest. The target sequence preferably is a nucleotide sequence that contains, represents or is associated with a polymorphism. The term polymorphism herein refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wild type form. Diploid organisms may be homozygous or heterozygous for allelic forms. A diallelic polymorphism has two forms. A triallelic polymorphism has three forms. A single nucleotide polymorphism occurs at a polymorphic site occupied by a single nucleotide, which is the site of variation between allelic sequences. The site is usually preceded by and followed by highly conserved sequences of the allele (e.g., sequences that vary in less than 1/100 or 1/1000 members of the populations). A single nucleotide polymorphism usually arises due to substitution of one nucleotide for another at the polymorphic site. Single nucleotide polymorphisms can also arise from a deletion of a nucleotide or an insertion of a nucleotide relative to a reference allele. Other polymorphisms include small deletions or insertions of several nucleotides, referred to as indels. A preferred target sequence is a target sequence that is associated with an AFLP® marker, i.e. a polymorphism that is detectable with AFLP®.

DNA

In the nucleic acid sample, the nucleic acids comprising the target may be any nucleic acid of interest. Even though the nucleic acids in the sample will usually be in the form of DNA, the nucleotide sequence information contained in the sample may be from any source of nucleic acids, including e.g. RNA, polyA$^+$ RNA, cDNA, genomic DNA, organellar DNA such as mitochondrial or chloroplast DNA, synthetic nucleic acids, DNA libraries, clone banks or any selection or combinations thereof. The DNA in the nucleic acid sample may be double stranded, single stranded and double stranded DNA denatured into single stranded DNA. Denaturation of double stranded sequences yields two single stranded fragments one or both of which can be analysed by probes specific for the respective strands. Preferred nucleic acid samples comprise target sequences on cDNA, genomic DNA, restriction fragments, adapter-ligated restriction fragments, amplified adapter-ligated restriction fragments. AFLP fragments or fragments obtained in an AFLP-template preamplification.

Samples

It is preferred that a sample contains two or more different target sequences, i.e. two or more refers to the identity rather than the quantity of the target sequences in the sample. In particular, the sample comprises at least two different target sequences, in particular at least 10, preferably at least 25, more preferably at least 50, more in particular at least 100, preferably at least 250, more preferably at least 500 and most preferably at least 1000 additional target sequences. In practice, the number of target sequences is limited, among others, by the number of connected circular probes. E.g., too many different oligonucleotide probes in a sample may corrupt the reliability of the multiplex amplification step.

A further limitation is formed e.g. by the number of fragments in a sample that can be resolved by the electrophoretic device in one injection. The number can also be limited by the genome size of the organism or the transcriptome complexity of a particular cell type from which the DNA or cDNA sample, respectively, is derived.

Multiple Injection

In a preferred embodiment of the invention, in order to come to a high throughput method of a multiplicity of samples, a number of samples are treated similar to thereby generate a multiplicity of amplified detection samples which can then be analysed on a multichannel device which is at least capable of detecting the labels and/or length differences. Suitable devices are described herein.

To increase throughput on electrophoretic platforms methods have been developed that are described in this application and are commonly depicted as multiple injection. By injecting multiple samples containing fragments of discrete, predetermined lengths, in the same electrophoretic matrix and/or in short consecutive runs, throughput can be increased. All detectable fragments preferably have a length within a specific span and only a limited number of fragments can be detected in one sample, hence the advantage of selective amplification for the reduction of the multiplex ratio by the selection of a subset of the connected probes in the amplification step resulting in a subset of amplicons.

Steps (a) to (e) of the method of the invention may be performed on two or more nucleic acid samples, each containing two or more different target nucleic acids, to produce two or more amplified samples in which is presence or absence of amplicons is analysed.

The multiplex analysis of the amplified samples following the method of the invention comprises applying at least part of an amplified sample to an electrophoretic device for subsequent separation and detection. Preferably such an amplified sample contains, or is at least suspected to contain, amplified connected probes, which is an indication that a target sequence has hybridised with the provided oligonucleotide probes and that those probes were annealed adjacently on the complementary target sequence so that they where connected, i.e. ligated. Subsequently, an amplified sample is subjected to a separating step for a selected time period before a next amplified sample is submitted.

In the method of the invention, (parts of) two or more different amplified samples are applied consecutively to the same channel of the electrophoretic device (FIG. 8). Depending on the electrophoresis conditions, the time period (23) between two (or more) consecutively applied amplified samples is such that the slowest migrating amplified connected probe (19) in an amplified sample is detected at the detection location (24), before the fastest migrating amplified connected probe of a subsequently applied amplified sample is detected at the detection location (24). Thus, the time intervals between subsequent multiple injections in one channel of the device are chosen such that consecutively applied samples after separation do not overlap at a point of detection.

In a preferred embodiment the method of the invention further comprises the following steps:

(e1) repeating steps (a) to (e) to generate at least two amplified samples;

(e2) consecutively applying at least part of the amplified samples obtained in steps (e) and (e1), to an application location of a channel of an electrophoretic device, electrophoretically separating the amplicons in the amplified samples and detecting the separated amplicons at a detection location located distal from the application location of the channel; whereby the time period between the consecutively applied amplified samples is such that the slowest migrating amplified connected probe in an amplified sample is detected at the detection location before the fastest migrating amplified connected probe of a subsequently applied amplified sample is detected at the detection location.

The method according to the invention allows for the high throughput analysis of a multiplicity of samples each comprising a multiplicity of different target sequences by the consecutive injection of amplified samples, comprising amplicons corresponding to the target sequences in the samples, in a channel of a multichannel electrophoretic device such as a capillary electrophoresis device. The method according to the invention allows for the analysis of a multiplicity of target sequences in a multiplicity of samples on a multiplicity of channels, thereby significantly increasing the throughput of the number of samples that can be analysed in a given time frame compared to conventional methods for the analysis of nucleotide sequences. This method profits from samples containing amplicons to be detected that are of a discrete size range as thereby the time period (23) between the successive injections can be significantly reduced compared to methods wherein the (remains of) concatamers are present.

The selected time period prevents that consecutively applied samples after separation have an overlap of amplicons at the detection point. The selected time period is influenced by i). the length of the amplicons; ii). the length variation in amplicons; and iii). the detection device and its operating conditions. Applying samples and separating consecutively applied samples in the same channel can be repeatedly performed in one or more channels, preferably simultaneously to allow for consecutive electrophoretic separation of multiple samples in one channel and/or simultaneous analysis of multiple samples over multiple channels and/or simultaneous analysis of multiple samples over multiple channels carried out consecutively. A graphic representation thereof is given in FIG. 8.

The period of time between two consecutively loaded amplified samples can be determined experimentally prior to executing the method. This period of time is selected such that, given the characteristics of an amplified sample, especially the difference in length between the shortest and the longest amplicons in an amplified sample, as well as other experimental factors such as gel (matrix) and/or buffer concentrations, ionic strength etc., the fragments in an amplified samples are separated to such extent at the detection location which is located at the opposite end (distal) from the application location where the sample was applied, that the different amplicons in a sample may be individually detected. After applying the last amplified sample, the separation can be continued for an additional period of time to allow the amplicons of the last sample to be separated and detected. The combination of the selected period of time between applying two consecutive samples and the optional additional time period is chosen such that at the detection location the different amplicons in consecutively applied samples are separated such that they may be individually detected, despite the limited length variation that exists between the different amplicons within a single sample. Thus overlapping migration patterns are prevented when samples containing fragments of varying length are consecutively applied (injected) on the electrophoretic device.

Using the method according to the invention, it is in principle possible and preferred to continuously apply, load or inject samples. Preferably the device is able to perform such operation automatically, e.g. controlled by a programmable computer. Preferably the multichannel device is suitable for such operation or is at least equipped for a prolonged operation without maintenance such as replacement of buffers, parts etcetera. However, in practice this will generally not be the case. When a final sample is submitted it is generally needed to continue the separation for an additional time period until the last fragment of the final sample has been detected. In a preferred embodiment of the invention, the stuffers present in the tags of the oligonucleotide probes is are used to provide the length differences (i.e. 0 to 500 nucleotides, bases or base pairs) between the amplified connected probes. The total length of the amplicon and the variation in the length is governed mostly by the techniques by which these fragments are analysed. In the high throughput multiple injection method of the present invention, it is preferred that the range of lengths of amplicons in an amplified sample has a lower limit of 40, 60, 80, or 100 and an upper limit of 120, 140, 160, or 180 nucleotides, bases or base pairs, for conventional (capillary) electrophoresis platforms. It is particularly preferred that the range of lengths of the amplicons varies from 100 to 140 nucleotides. However, these numbers are strongly related to the current limits of the presently known techniques. Based on the knowledge provided by this invention, the skilled artisan is capable of adapting these parameters when other circumstances apply.

The reliability of the multiplex amplification is further improved by limiting the variation in the length of the amplified connected probes. Limitations in the length variation of amplicons is preferred to use multiple injection more efficiently and further results in reduction of the preferential amplification of smaller amplicon in a competitive amplification reaction with larger connected probes. This improves the reliability of the high throughput method of the present invention. Together with the multiple injection protocol as herein disclosed, these measures, alone or in combination provide for a significant increase in throughput in comparison with the art. A further improvement of the high throughput capacity is obtained by limiting the number of different amplicons in a sample. It is regarded as more efficient and economical to limit the multiplex capacity of the ligation/ amplification step in combination with the introduction of a multiple injection protocol. One of the most advantageous aspects of the present invention lies in the combination of multiplex ligation, multiplex amplification, preferably with a single primer pair or with multiple primer pairs which each amplify multiple connected probes, repeated injection and multiplex detection of different labels. One of the further advantageous aspects of the present invention resides in the combined application of length differences with different (overlapping) labels such that each connected probe and hence each target sequence within one sample can be characterised by a unique combination of length and label. This allows for a significant improvement of the efficiency of the analysis of target sequences as well as a significant reduction in the costs for each target analysed.

The multiple injection protocol can be performed in a variety of ways. One of these is the multiple loading of two or more samples in the same matrix. This is considered as advantageously as the matrix is re-used by performing consecutive short runs, thereby increasing efficiency and throughput. Another one is the multiple loading of two or more samples in the same matrix in the same run. It is preferred to re-use the matrix by performing short consecutive runs. In this embodiment, a first sample is injected and separated. As soon as the last fragment is detected, the next sample is loaded. Preferably, between these two consecutive short runs the matrix is not replaced so that the runs are performed in the same matrix. This provides for additional efficiency and improved economics as less changes o the matrix need to occur, reducing the amount of consumables of this type of analysis (i.e. buffers etc.), reducing the cost per datapoint. Furthermore time-consuming replacements of the matrix can be avoided to a large extent, further increasing the efficiency of the method.

In itself, certain aspects of multiple loading or multiple injection have been described inter alia in U.S. Pat. No. 6,156, 178 and WO 01/04618. The latter publication discloses an apparatus and a method for the increased throughput analysis of small compounds using multiple temporally spaced injections. The publication discloses that samples comprising primers, extended by one nucleotide (single nucleotide primer extension or SnuPE, also known as minisequencing) could be detected using multiple temporally spaced injections on a capillary electrophoresis device. Minisequencing is based on annealing a complementary primer to a previously amplified target sequence. Subsequent extension of the primer with a separately provided labelled nucleotide provides for identification of the nucleotide adjacent to the primer. Principally, the primer extension product is of a constant length. To increase throughput the use of successive injections of extension products of the same length per run is suggested. To further increase the throughput, primers of a different length can be used, varying typically from 15 to 25 nucleotides. In contrast, the present invention contemplates analysing multiplex amplification products themselves directly with a length variation typically between 50 and 150 nucleotides. This is significantly more economical than minisequencing or SnuPE as outlined hereinbefore because multiple target sequences are amplified in a single reaction, whereas with minisequencing or SnuPE amplification is carried out individually for each target sequence. Furthermore, the use of primers of a different length and complementary to the target sequence compromises the efficiency of the subsequent amplification step needed in the method of the present invention. These applications in general do not address the problems associated with high throughput detection of highly multiplexed samples, nor provide solutions thereto.

Exonucleases

A preferred method of the invention further comprises a step for the removal of oligonucleotide probes that are not annealed to target sequences and/or that are non-connected/ligated. Removal of such probes preferably is carried out prior to amplification, and preferably by digestion with exonucleases. By removal/elimination of the oligonucleotide probes that are not connected/ligated a significant reduction of ligation independent (incorrect) target amplification can be achieved, resulting in an increased signal-to-noise ratio. One solution to eliminate one or more of the non-connected/ligated components without removing the information content of the connected probes is to use exonuclease to digest non-connected/ligated oligonucleotide probes.issensitive. sensitive. Blocking groups include use of a thiophosphate group and/or use of 2-O-methyl ribose sugar groups in the backbone. Exonucleases include ExoI (3'-5' activity), Exo III (3'-5' activity), and Exo IV (both 5'-3' and 3'-5' activity). The circular probes of the present invention are, once ligated, insensitive to the exonuclease, as opposed to the unligated circular probes This is a further advantage of the use of padlock probes in the present invention.

An advantage of using exonucleases, for example a combination of Exo I (single strand specific) and Exo III (double strand specific), is the ability to destroy both the target sequence and the unligated oligonucleotide probes, while leaving the ligation product sequences substantially undigested. By using an exonuclease treatment prior to amplification, the oligonucleotide probes in each set are substantially reduced, and thus hybridisation of the remaining unligated oligonucleotide probes to the original target DNA (which is also substantially reduced by exonuclease treatment) and formation of a ligation product sequence which is a suitable substrate for PCR amplification by the oligonucleotide primer set is substantially reduced, thereby improving the signal to noise ratio.

Size Ladder

The sample can be supplied with a nucleotide fragment size standard comprising one or more nucleotide fragments of known length. Methods of preparing and using nucleotide size standards are well known in the art (see e.g. Sambrook and Russel, 2001, supra). Such a size standard forms the basis for appropriate sizing of the amplicons in the sample, and hence, for the proper identification of the detected fragment. The size standard is preferably supplied with every sample and/or with every injection. A size standard preferably contains a variety of lengths that preferably spans the entire region of lengths to be analysed. In a particular embodiment of the invention, it is considered advantageously to add flanking size standards from which the sizes of the amplicons can be derived by interpolation. A flanking size standard is a size standard that comprises at least two labelled oligonucleotide sequences of which preferably one has a length that is at least one base shorter than the shortest amplified connected probe and preferably one that is a least one base longer than the longest amplified connected probe to allow interpolation and minimise the introduction of further length variation in the sample. A preferred flanking size standard contains one nucleotide that is one nucleotide shorter the shortest amplified connected probe and one that is a least one base longer than the longest amplified connected probe and is labelled with at least one dye that is identical to the label used for labelling the amplicons contained in the sample.

A convenient way to assemble a suitable size standard is by (custom) chemical synthesis of oligonucleotides of the appropriate lengths, which are end-labelled with a suitable label.

The size standard is applied with every consecutively applied sample to serve as local size references to size the loaded sample fragments. The size standard may be applied in the same channel or lane of the electrophoretic device as the sample to be analysed, i.e. together with the sample, or may be applied in a parallel channel or lane of a multichannel/lane device. The flanking size standard can be labelled with any of the labels used in the method. If the size standard is applied in the same channel of the device, the fragments of the standard are preferably labelled with a label that can be distinguished from the labels used for the detection of the amplicons in a sample.

Pooling

In a variant of the technology, the starting (DNA) material of multiple individuals are pooled such that less detection samples containing this material are loaded on the detection device, This can be advantageous in the case of Linkage Disequilibrium (LD mapping) when the objective is to identify amplified connected probes (such as those representing SNP alleles) that are specific for a particular pool of starting samples, for example pools of starting material derived from individuals which have different phenotypes for a particular trait.

Application

One aspect of the invention pertains to the use of the method in a variety of applications. Application of the method according to the invention is found in, but not limited to, techniques such as genotyping, transcript profiling, genetic mapping, gene discovery, marker assisted selection, seed quality control, hybrid selection, QTL mapping, bulked segregant analysis, DNA fingerprinting and microsatellite analysis. Another aspect pertains to the simultaneous high throughput detection of the quantitative abundance of target nucleic acids sequences. This approach is commonly known as Bulk Segregant Analysis (BSA).

Detection of Single Nucleotide Polymorphisms

One particular preferred application of the high throughput method according to the invention is found in the detection of single nucleotide polymorphisms (SNPs). A first target complementary part of the circular oligonucleotide probes is preferably located adjacent to the polymorphic site, i.e. the single polymorphic nucleotide. A second target complementary part is designed such that its terminal base is located at the polymorphic site, i.e. is complementary to the single polymorphic nucleotide. If the terminal base is complementary to the nucleotide present at the polymorphic site in a target sequence, it will anneal to the target sequence and will result in the ligation of the two target complementary parts. When the end-nucleotide, i.e. the allele-specific nucleotide does not match, no ligation or only a low level of ligation will occur and the polymorphism will remain undetected.

When one of the target sequences in a sample is derived from or contains a single nucleotide polymorphism (SNP), in addition to the probes specific for that allele, further probes can be provided that not only allow for the identification of that allele, but also for the identification of each of the possible alleles of the SNP (co-dominant scoring). To this end a combination of target complementary parts can be provided: one complementary part is the same for all alleles concerned and one or more of the other complementary parts which is specific for each of the possible alleles. These one or more other type of complementary parts contain the basically the same complementary sequence but differ in that each contains a nucleotide, preferably at the end, that corresponds to the specific allele. The allele specific part can be provided in a number corresponding to the number of different alleles expected. The result is that one SNP can be characterised by the combination of one complementary part with four other (allele-specific) complementary parts, identifying all four theoretically possible alleles (one for A, T, C, and G), by incorporating stuffer sequences of different lengths (preferred) or different labels into the allele specific probes.

In a particular embodiment, preferably directed to the identification of single nucleotide polymorphisms, the first complementary part of the oligonucleotide probe is directed to a part of the target sequence that does not contain the polymorphic site and the second complementary part of the oligonucleotide probe contains, preferably at the end distal from first complementary part, one or more nucleotide(s) complementary to the polymorphic site of interest. After ligation of the adjacent parts, the connected probe is specific for one of the alleles of a single nucleotide polymorphism.

To identify the allele of polymorphic site in the target sequence, a set of oligonucleotide probes can be provided wherein one first complementary part is provided and one or more second complementary parts. Each second complementary part then contains a specific nucleotide at the end of the complementary sequence, preferably the 3'-end, in combination with a known length of the stuffer. For instance, in case of an A/C polymorphism, the second complementary part can contain a specific nucleotide T in combination with a stuffer length of 2 nucleotides and another second complementary part for this polymorphism combines G with a stuffer length of 0. As the primers and the complementary parts of the probes are preferably the same length, this creates a length difference of the resulting amplicons of 2 nucleotides. In case the presence and/or the absence of all four theoretically possible nucleotides of the polymorphic site is desired, the stuffer-specific nucleotide combination can be adapted accordingly. In a sample containing multiple target sequences, amplified with the same pair of amplification-primers (and hence label) or with multiple pairs of amplifications primers with labels that have overlapping emission spectra, the combined stuffer lengths are chosen such that all connected probes are of a unique length. In FIG. 4 an illustration of this principle is provided of two loci and for each locus two alleles. In a preferred embodiment this principle can be extended to at least ten loci with at least two alleles per locus.

Detection of Specific Target Sequence

The target sequence contains a known nucleotide sequence derived from a genome. Such a sequence does not necessarily contain a polymorphism, but is for instance specific for a gene, a promoter, an introgression segment or a transgene or contains information regarding a production trait, disease resistance, yield, hybrid vigour, is indicative of tumours or other diseases and/or gene function in humans, animals and plants. To this end, the first and second complementary parts of the circular probe are designed to correspond to a, preferably unique, target sequence in genome, associated with the desired information. The complementary parts in the target sequence are located adjacent to each other. In case the desired target sequence is present in the sample, the two probes will anneal adjacently and after ligation and amplification can be detected.

Detection of AFLP Markers

AFLP, its application and technology is described in Vos et al., Nucleic Acids Research, vol. 23, (1995), 4407-4414 as well as in EP-A 0 534 858 and U.S. Pat. No. 6,045,994, all incorporated herein by reference. For a further description of AFLP, its advantages, its embodiments, its techniques, enzymes, adapters, primers and further compounds, tools and definitions used, explicit reference is made to the relevant passages of the publications mentioned hereinbefore relating to AFLP. AFLP and its related technology is a powerful DNA fingerprinting technique for the identification of for instance specific genetic markers (so-called AFLP-markers), which can be indicative of the presence of certain genes or genetic traits or can in general be used for comparing DNA, cDNA or RNA samples of known origin or restriction pattern. AFLP-markers are in general associated with the presence of polymorphic sites in a nucleotide sequence to be analysed. Such a polymorphism can be present in the restriction site, in the selective nucleotides, for instance in the form of indels or substitutions or in the rest of the restriction fragment, for instance in the form of indels or substitutions. Once an AFLP marker is identified as such, the polymorphism associated with the AFLP-marker can be identified and probes can be developed for use in the ligation assay of the present invention.

In another aspect the present invention pertains to a circular nucleic acid probe comprising a first and a second part that is capable of hybridising to corresponding parts of a target sequence and further comprising at least one, preferably two primer-binding sequence and a stuffer. Further embodiments of the probe according to the present invention are as described herein above. The invention also pertains to a set of probes comprising two or more probes wherein each probe comprises a first part and a second part that is complementary to part of a target sequence and wherein the complementary first an second parts are located essentially adjacent when hybridised to the target sequence and wherein each probe further comprises a stuffer, which stuffer is located essentially next to the complementary part and at least one, preferably two primer-binding sequence located essentially adjacent to the stuffer.

The invention in a further aspect, pertains to the use of a circular probe or set of probes in the analysis of at least one nucleotide sequence and preferably in the detection of a single nucleotide polymorphism, wherein the set further comprises at least one additional probe that contains a nucleotide that is complementary to the known SNP allele. Preferably the set comprises a probe for each allele of a specific single nucleotide polymorphism. The use of a set of probes is further preferred in a method for the high throughput detection of single nucleotide polymorphisms wherein the length of the stuffer in the probe is specific for a locus and/or allele of a single nucleotide polymorphism Another aspect of the invention relates to the primers and more in particular to the set of primers comprising a first primer and one or more second primers, wherein each second primer contains a label and which second primer comprises a nucleotide sequence that is specific for said label.

The present invention also finds embodiments in the form of kits. Kits according to the invention are for instance kits comprising probes suitable for use in the method as well as a kit comprising primers, further a combination kit, comprising primers and probes, preferably all suitably equipped with enzymes buffers etcetera, is provided by the present invention.

The efficiency of the present invention can be illustrated as follows. When a capillary electrophoretic device with 96 channels and capable of detecting four labels simultaneously is used, allowing for 12 subsequent injections per run per channel with a empirically optimised minimum selected time period between the injections, a sample containing 20 target sequences of interest allows for the high throughput detection of 96 (channels)*12 (injections)*20 (targets)*4 (labels) =92160 target sequences, using the method of the present invention. In the case of co-dominant SNP-detection, data regarding 46080 SNPs can be detected in a single run.

DESCRIPTION OF THE FIGURES

This invention is illustrated by the accompanying figures. In the figures, many of the features of the invention are demonstrated using two linear probes that hybridise adjacently. The skilled man will appreciate that most of these features also apply to other embodiments disclosed herein such as the circular probes and how to include those features in the other embodiments such as the circular probes based on the information provided in this application.

Figure 1:
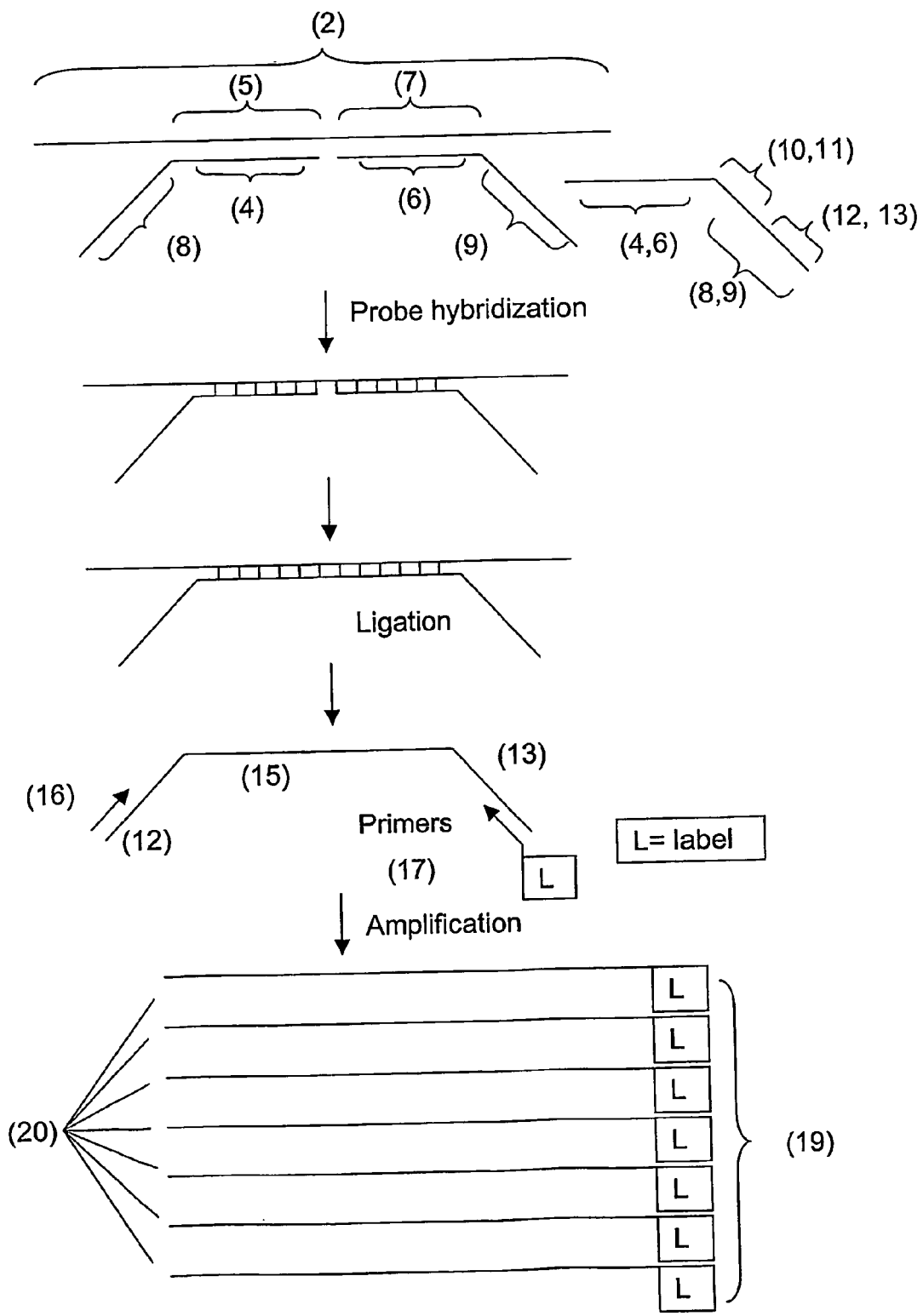
FIG. 1: Schematic representation of the oligonucleotide ligation-amplification assay, resulting in amplified connected probes.

A target sequence (2) comprising a first (5) and a second (7) part to which parts first and second probes can be hybridised with sections (4) and (6) that are complementary, respectively. The probes contain a tag sequence (8,9) that is not complementary to the target sequence. The tag sequence may comprise a stuffer sequence (10,11) and a primer-binding site (12,13). After probe hybridisation and ligation the connected probe (15) can be amplified using primers (16, 17) capable of hybridising to the corresponding primer-binding sites. At least one of the primers contains a label (L). Amplification results in an amplified sample, comprising amplicons (20)

Figure 2:
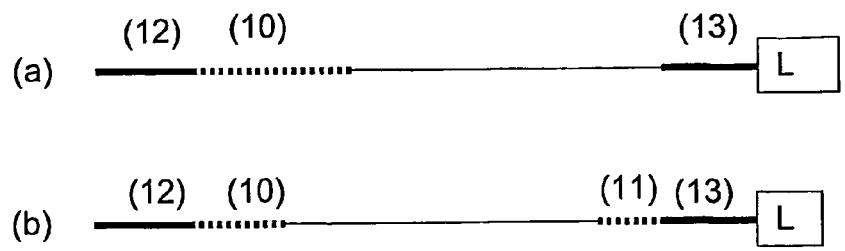

FIG. 2: Schematic representation of two connected probes, wherein
(a) only one probe contains a stuffer (10) and primer-binding sequences (12,13); and
(b) both probes contain a stuffer (10, 11) and primer-binding sequences (12,13).

Figure 3:
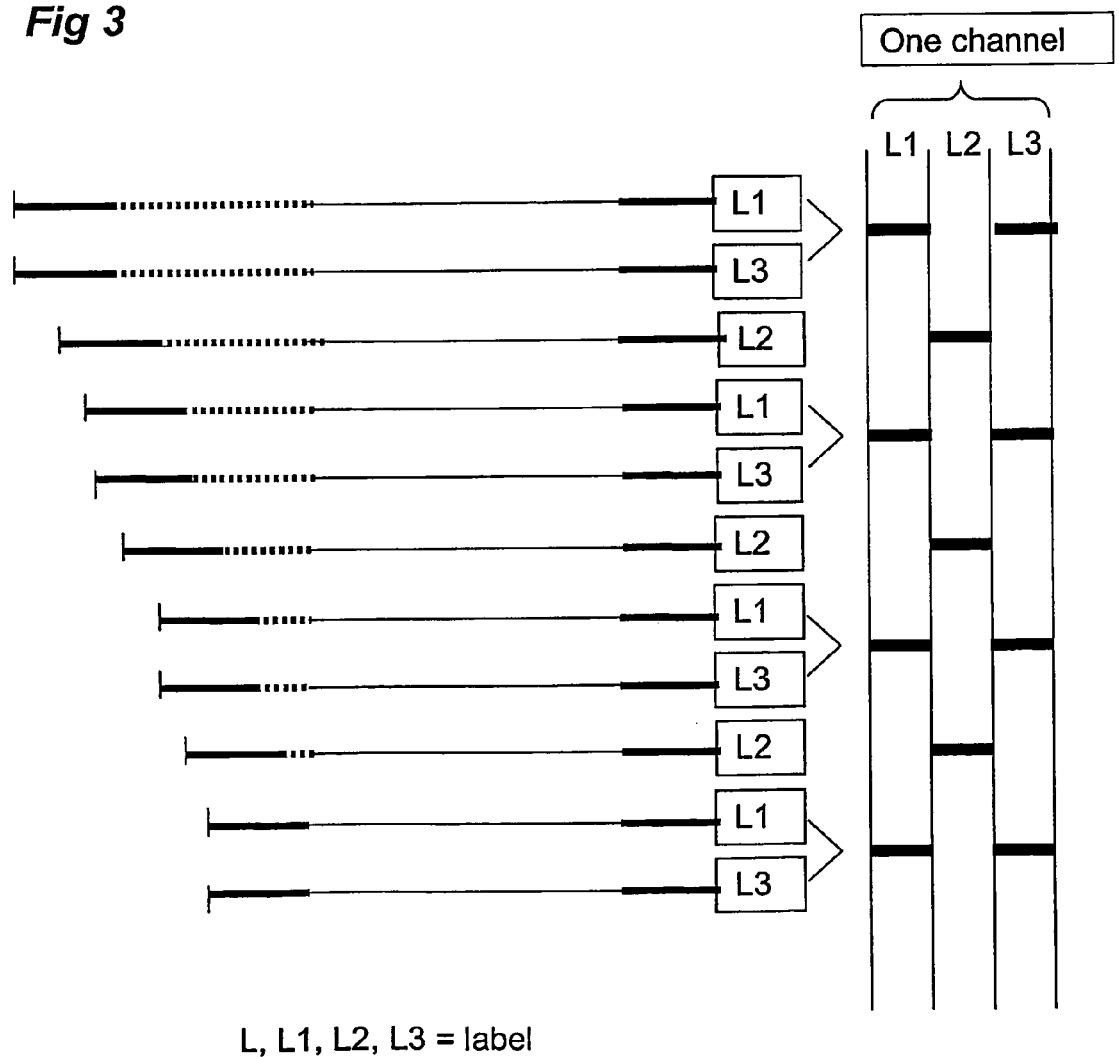

FIG. 3: Schematic representation of the unique combination of different lengths and labels with a schematic elution profile in one channel of a multichannel device.

FIG. 4: Schematic representation of the oligonucleotide ligation-ligation assay of the present invention. The principle is represented for two loci 1 and 2 and for each locus two alleles for reasons of simplicity only, but can easily be extended to at least 10 loci with 2 alleles each. The primer set consists of one first primer (solid bold line) and one second primer (dashed bold line). The theoretically possible connected probes are schematically outlined, together with the primers. The connected probes differ in length.

Figure 5:
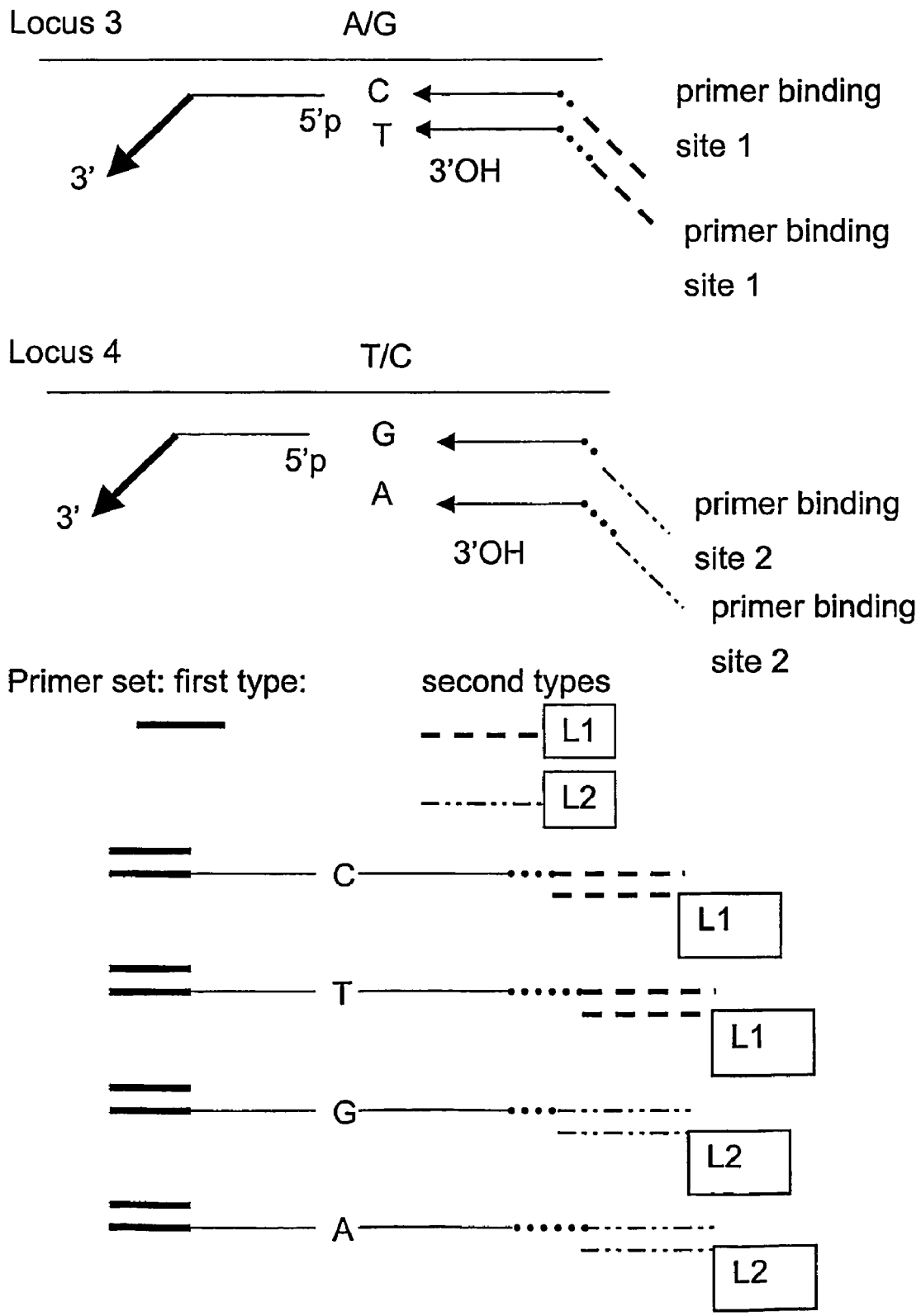

FIG. 5: Schematic representation of the oligonucleotide ligation-ligation assay of the present invention. The principle is represented for two loci 3 and 4 and for each locus two alleles. The primer set consists of one first primer and two second primers. The theoretically possible connected probes are schematically outlined, together with the primers. The connected probes differ in length and in label.

Figure 6:
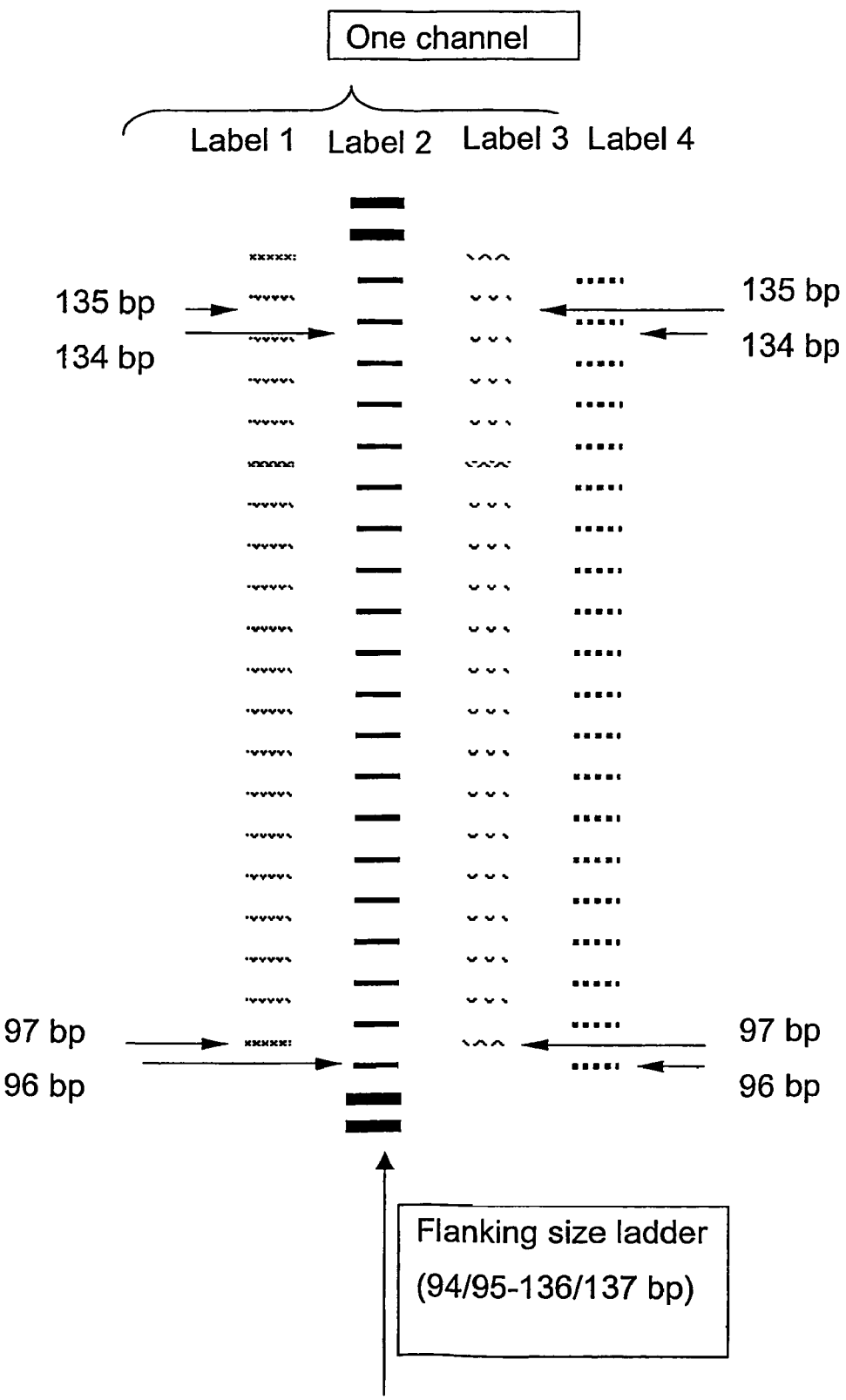

FIG. 6: Schematic representation of the results of a sample containing 80 amplified connected probes with:
  a length difference between 135 base pairs (bp) to 97 bp for the amplified connected probes with an odd length and labelled with Label 1 and Label 3; and
  a length difference between 134 bp to 96 bp for the amplified connected probes with an even length and labelled with Label 2 and Label 4; and
  a flanking size ladder with oligonucleotides of 94/95 and 136/137 (bp) carrying label 1, 2, 3 or 4

Figure 7:
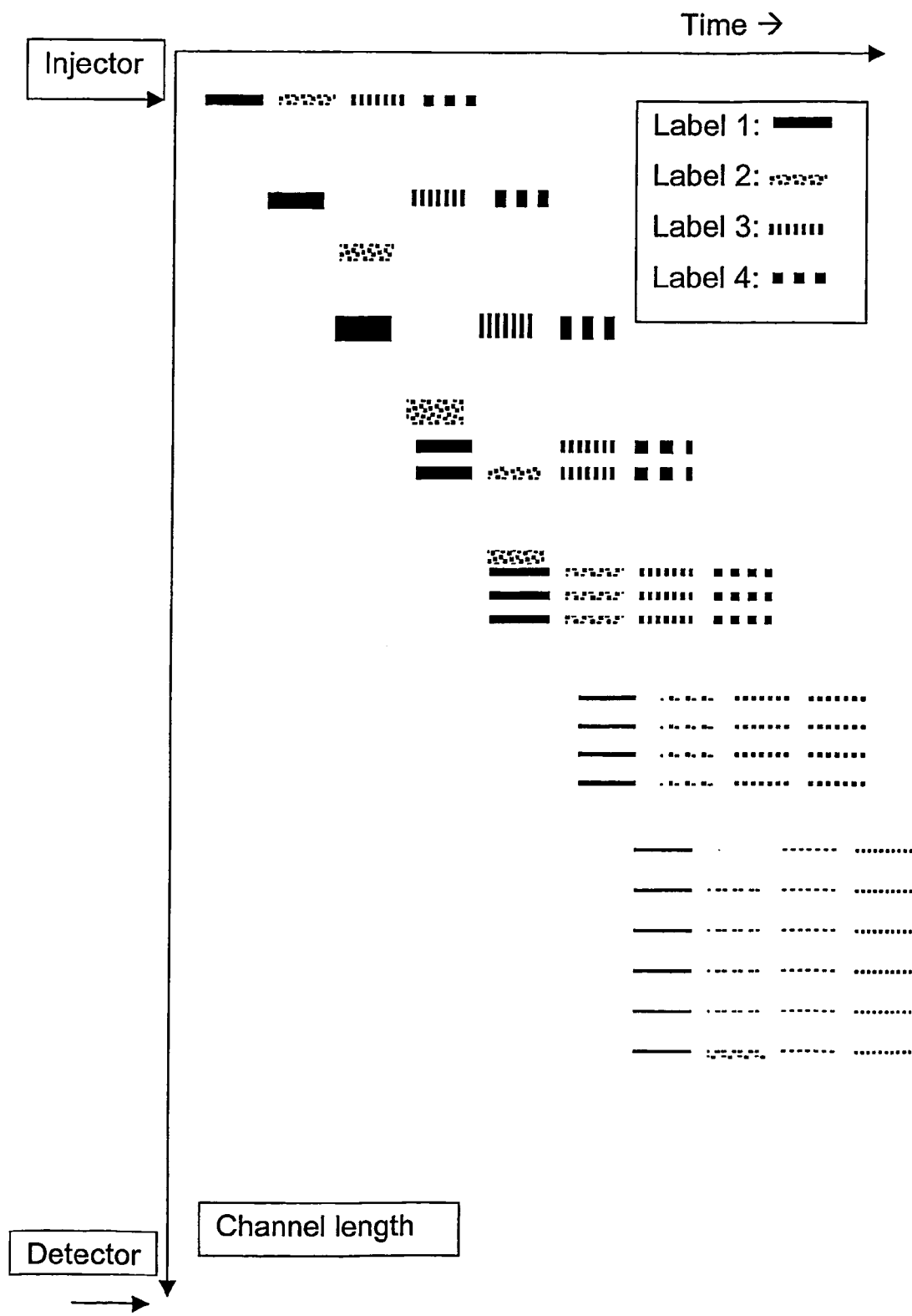

FIG. 7: Schematic representation of the separation profile in one channel, submitting one sample comprising multiple amplified connected probes labelled with Label 1, 2, 3, and 4. The multiple labelled amplified connected probes are detectably separated at the point of detection.

Figure 8:
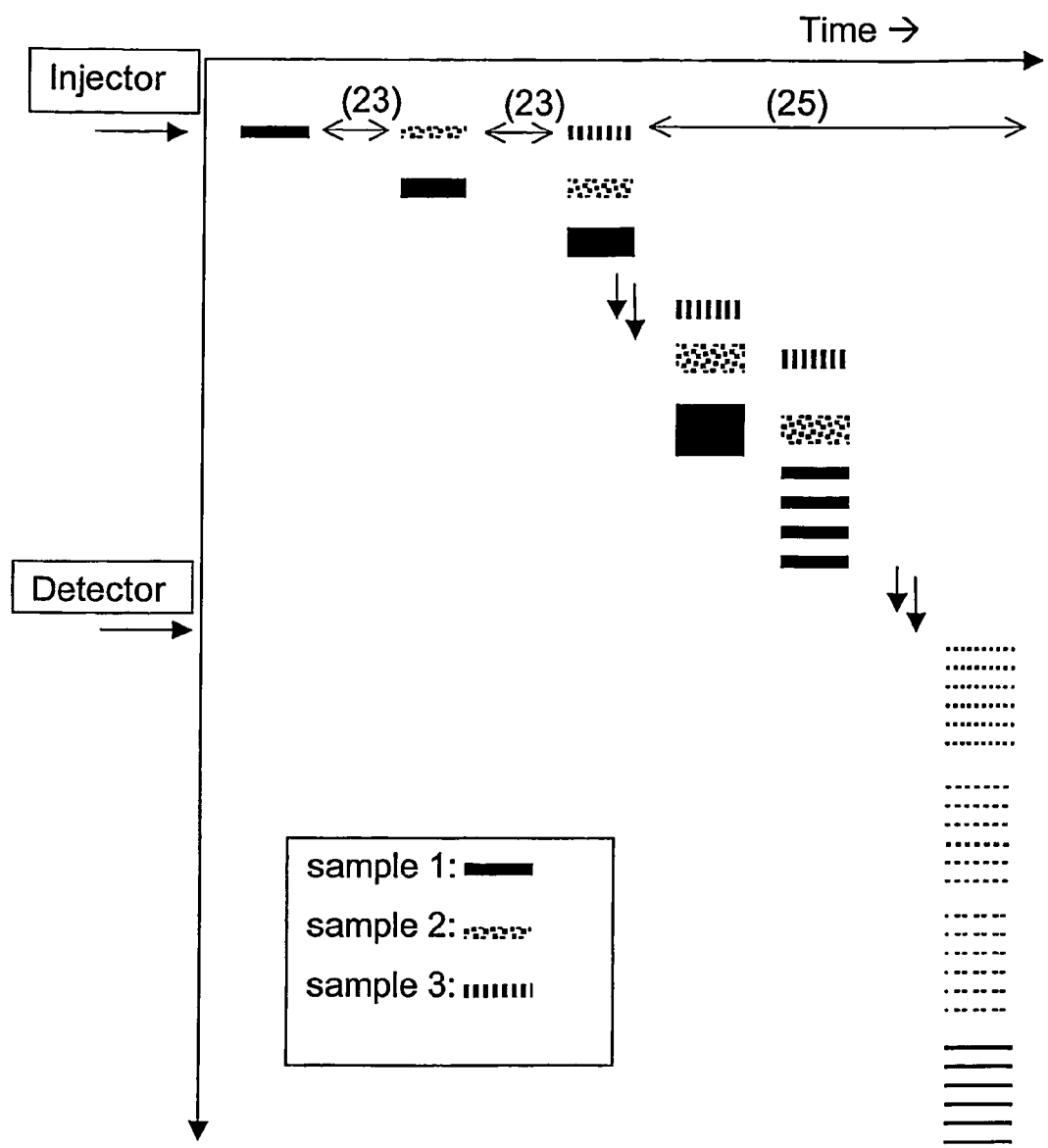

FIG. 8: Schematic representation of the multiple injection of samples in one channel, with a graphic illustration of the selected time period (23) between the injection of subsequent samples and the additional time period (25) after submitting the last sample.

Figure 9:
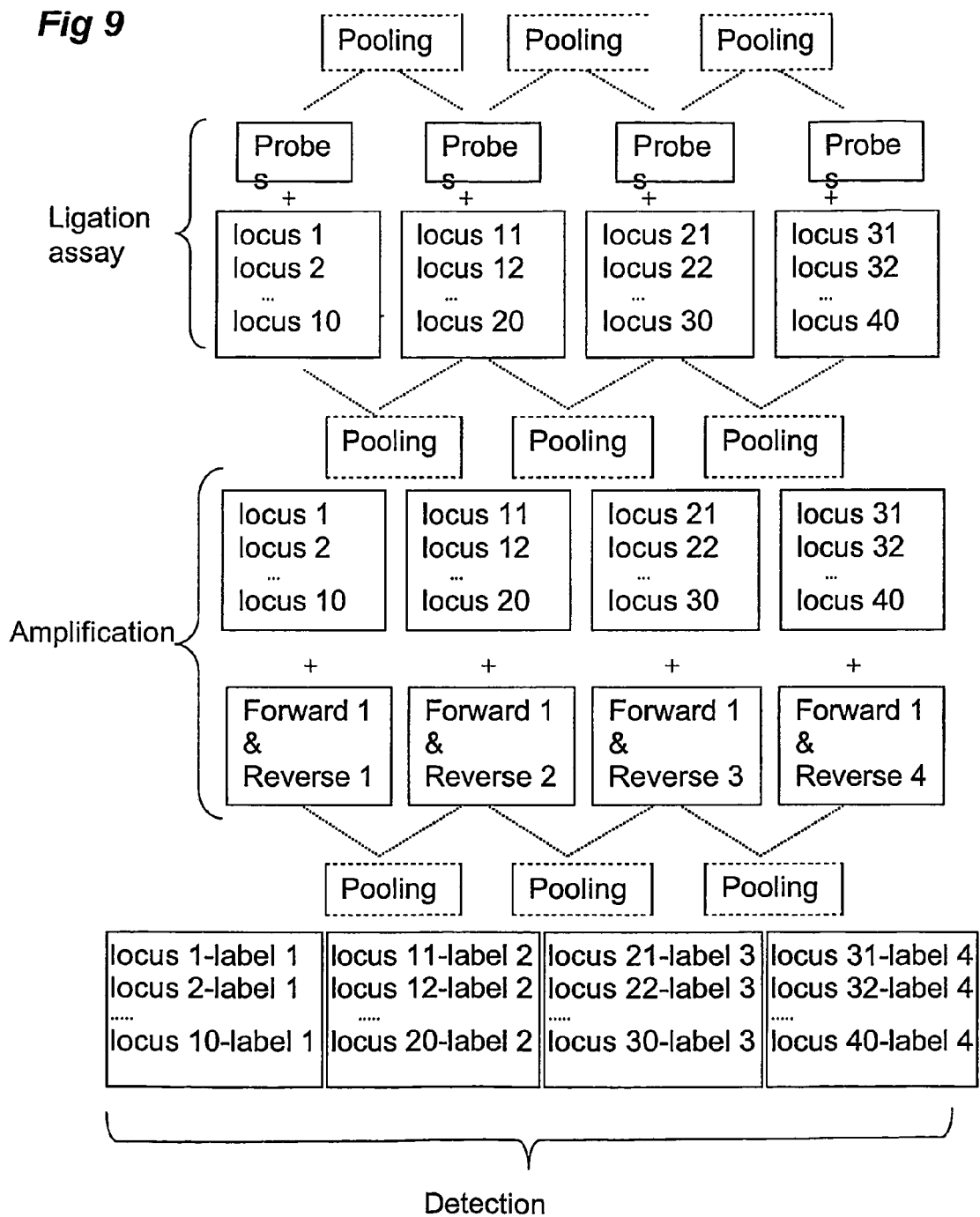

FIG. 9: Schematic representation of the ligation of up to 40 loci, and the subsequent amplification and detection phase of the method. Depending on the complexity and the number of loci to be analysed, the points in the procedure at which pooling can be contemplated is indicated as an optional (dotted) feature). Amplification is here carried out by using one forward primer (Forward) and for each label one (differently labelled) reverse primer (Reverse 1, 2, 3, 4). When the ligation (sub)samples are pooled, there are in principle two options for amplification. For instance if (sub)samples derived from Loci 1-10 are pooled with (sub)samples derived from Loci 11-20 prior or subsequent to ligation, the pooled (sub)sample can be amplified with the Forward primer and the Reverse primers 1 and 2 in one step or in two steps, first with Forward and Reverse 1, followed by Forward and Reverse 2 or vice versa. Detection can also be performed in a similar way, detecting both labels simultaneously or first label 1, followed by label 2, optionally by double injection.

Figure 10:
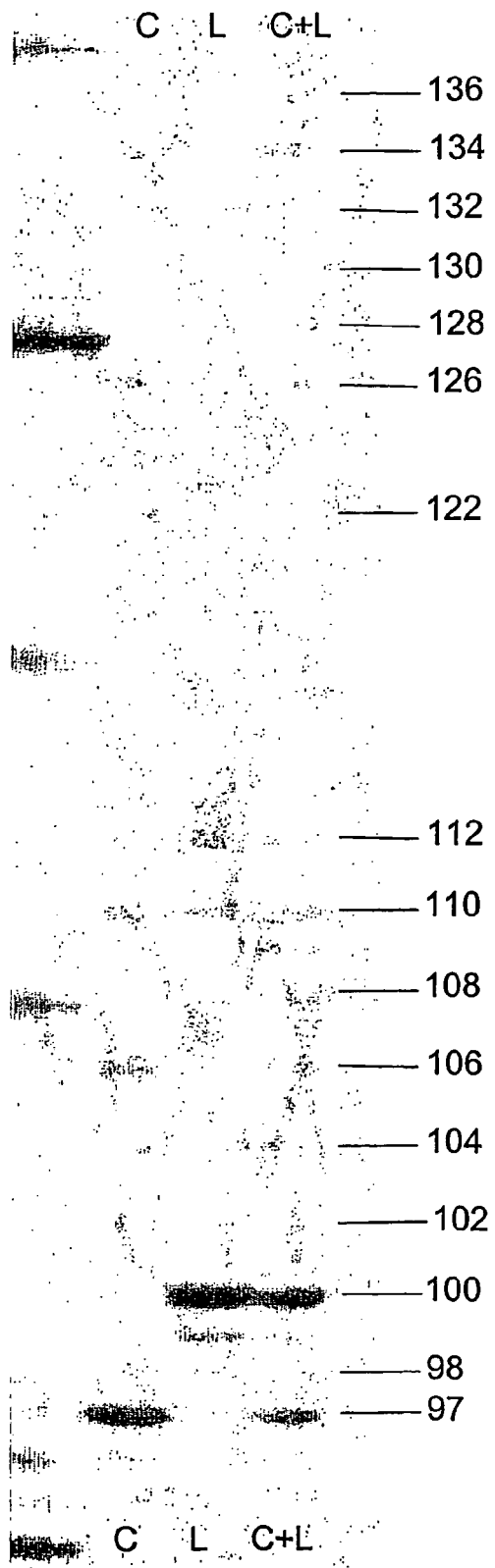

FIG. 10: A gel of a multiplex oligonucleotide ligation assay of 12 SNPs from the Colombia ecotype, the Landsberg erecta ecotype and a 50/50 mixture of the Colombia and the Landsberg erecta ecotypes.

FIG. 11: A. Partial electropherogram of FAM labelled detection of the Colombia sample on a capillary electrophoretic device (MEGABace). The same multiplex mixture was injected. Amplified connected probes in a size range 97-134 bp and flanking sizer fragments (designated S) are 94, 95 and 137 bp. Probes and sizers are all labelled with FAM.

B. Partial electropherogram of FAM labelled detection of the Landsberg erecta sample on a capillary electrophoretic device (MEGABace). The same multiplex mixture was injected. Amplified connected probes in a size range 97-134 bp and flanking sizer fragments (designated S) are 94, 95 and 137 bp. Probes and sizers are all labelled with FAM.

Figure 12:
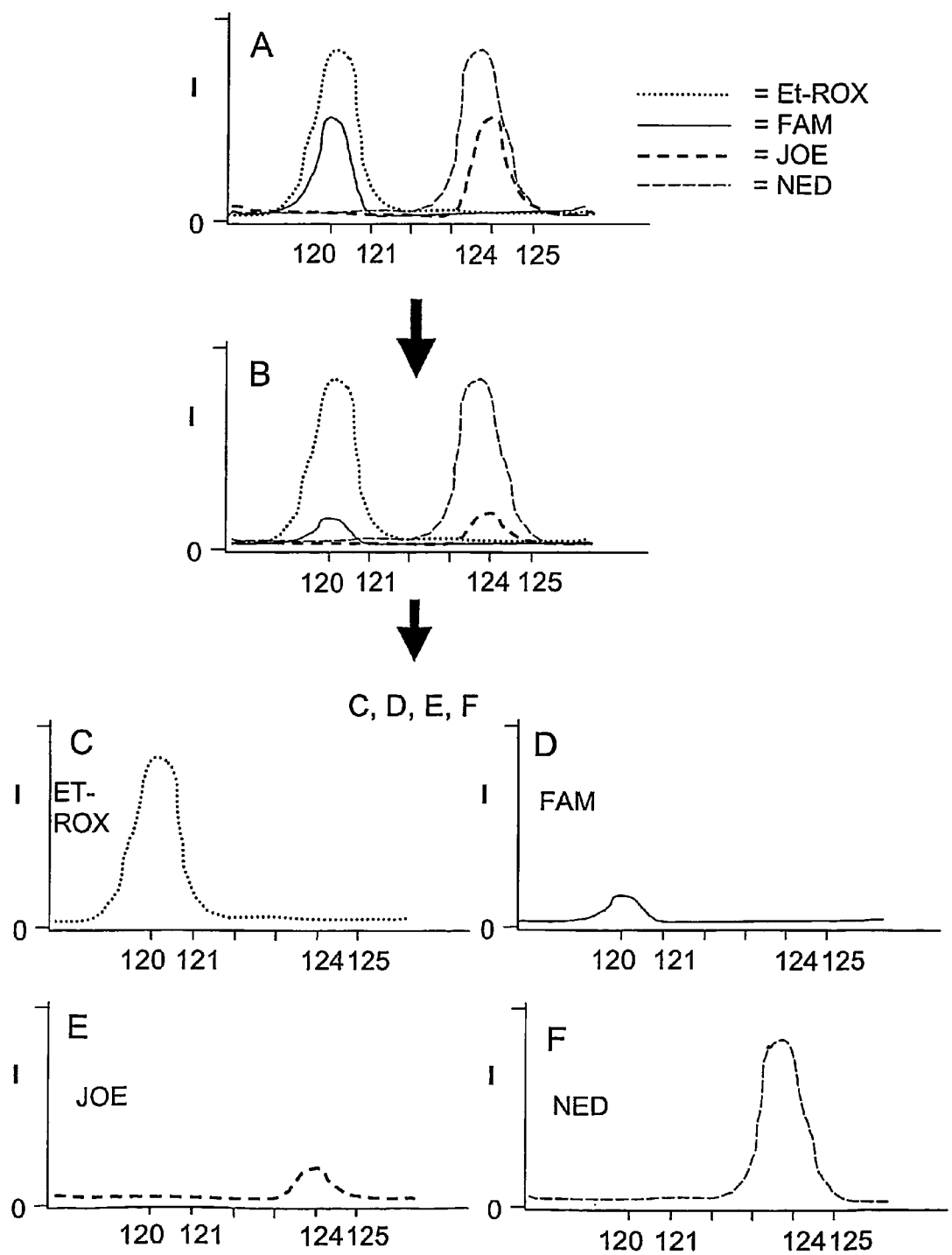

FIG. 12: A: Raw trace file of a sample containing a 120 bp ET-ROX labelled fragment and a 124 bp NED-labelled fragments. Note the FAM and JOE labels from other labelled fragments in the sample with the same length. FAM and JOE have overlapping fluorescence spectra (ET-ROX and FAM, JOE and NED), resulting in overlapping signals (cross-talk) with sequences of equal length.

B: Mathematical cross-talk correction resulting in a processed, cross-talk corrected trace file. Cross talk is reduced, but remains of the overlapping spectra (FAM, JOE) are present, resulting in false positive (or negative) signals.

C, D, E, F: single label plots illustrate the presence of remnants (D, E) of the mathematical correction, compared to the positive signals (C, F)

FIG. 13 A: Representation of the effect of incomplete removal of cross-talk of a 120 bp ET-ROC fragment and a 124 bp NED fragment, resulting in incorrect scored data, compared to theoretically expected data.

B: Representation of the effect of the use of cross-talk correction by length-label combinations. Scored data and expected data are correctly interpreted and false-positive or negative data are eliminated.

FIG. 14: Representation of a circular probe with primer binding sites, primers and an optional blocking section and their relative positioning in the circular probe. After amplification amplicons are formed that are representations of the circular probe.

FIG. 15: Representation of the design of the selective or nested primers used in the selective amplification of a sample of connected circular probes. The connected circular probe is schematically drawn with one primer binding site and adjacent nucleotides denoted as N. For a 24-plex ligation assay, the selective amplification with one selective nucleotide is used to visualise the reduction to 6-plex amplification and detection assays.

Figure 16:
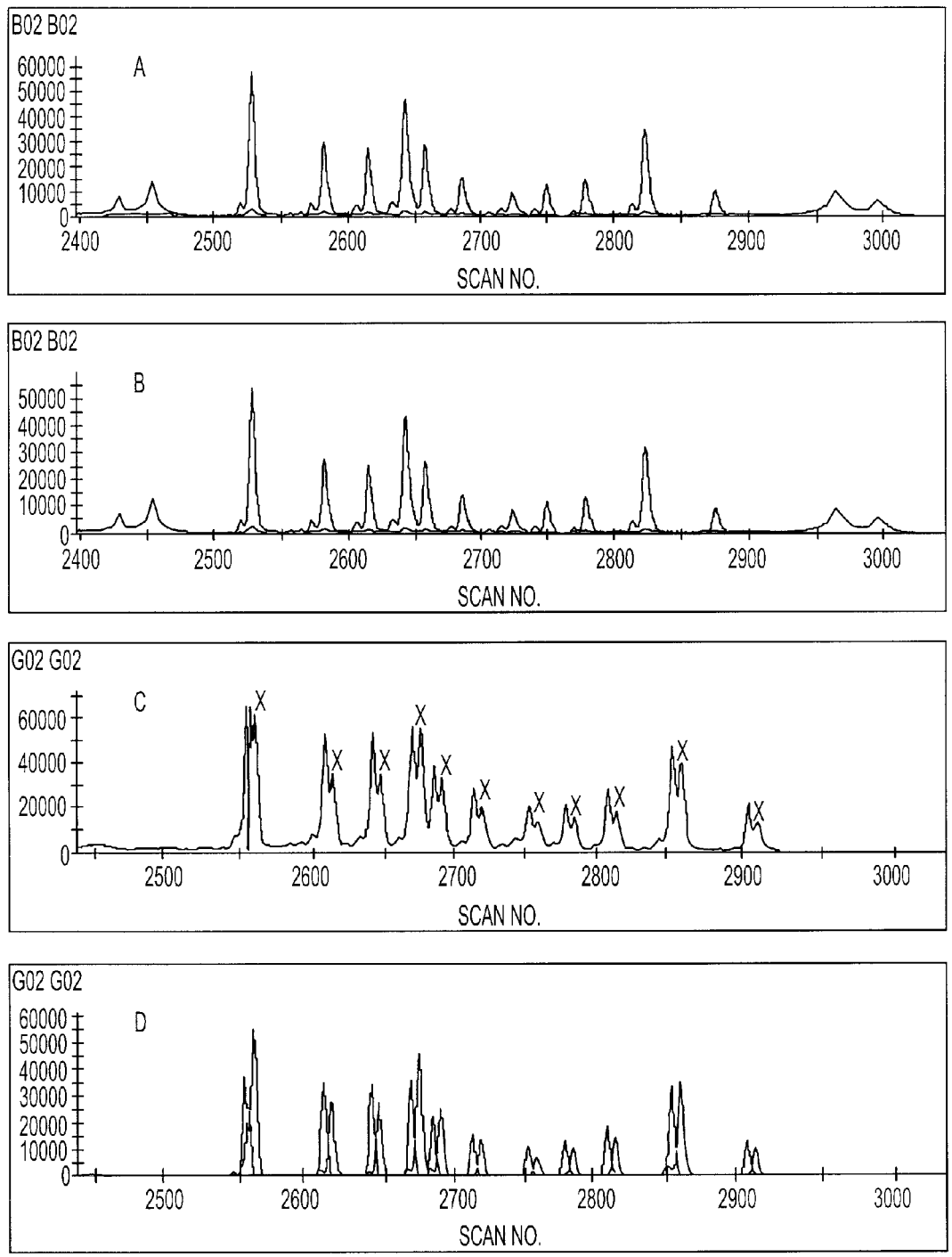

FIG. 16: Amplification with primer Eook+T5'-JOE of a 10 plex ligation product of set 4 on sample 2. Signal of Joe channel is shown.

A. Cross-talk in the NED channel caused by the amplification of the 10 plex ligation of set 4 on sample 2 with primer Eook+T5'-JOE (see A). NED signal has been omitted.

B. Signal in the NED channel caused by the amplification with primer Eook+T5'-JOE and a NED labelled E00k amplification of a 10 plex ligation of set 4 on sample 2 (see A). Because 5'+T E00k-Joe signal in NED differs 1 bp, this two peaks can be distinguished. X means cross-talk of the Joe fluorescent dye in Ned channel (corresponds to signal in B).

C. Amplification of a 10-plex ligation of set 4 on sample 2 was carried out using a NED labelled E00k amplification primer and a 5'+T E00k JOE labelled primer and the reaction products were combined for detection on the MegaBACE. Unprocessed signal in the NED channel is shown Because the JOE labelled products differ by one bp in length, the peaks from NED and JOE can be distinguished in the NED channel.

D. The same reaction products shown in C but after processing of the raw data, i.e. after cross talk removal. The 1 bp size difference of the 5'T E00k JOE products prevent miss-scoring caused by cross-talk of JOE signals into the NED channel as show in FIGS. 16 A, B and C.

All signals of A, B, C and D are obtained after processing by Genetic Profiler version 1 software from Molecular Dynamics. Signal shown in D is corrected for cross talk and hence shows processed signals. The signals in A, B, and C are raw data and are not corrected for cross talk.

FIG. 17:

A. Analysis of 5'+T Joe and FAM labelled E00k amplification of ligation products of set 4 for sample 5 (capillary G05) and 6 (capillary G06). Run time was 40 minutes.

B. Second analysis of 5'+T Joe and FAM labelled E00k amplification of ligation products of set 4 for sample 5 (capillary G05) and 6 (capillary G06). This run was performed directly after the one shown in A, on the same matrix. Run time was 40 minutes.

FIG. 18:

Selective amplification of 3 sets out of one 40-plex ligation for sets 1, 2, 4 and 5 from sample 3.

A. Selective amplification of set 1 with E01k-Ned and M01k.

B. Selective amplification of set 2 with E03k-5'+T-JOE and M04k.

C. Selective amplification of set 5 with E04k-Fam and M03k.

All channels are visible. It is clear that it is possible to amplify a specific set out of a multiplex ligation product for more sets.

EXAMPLES

I. Design of the Stuffer Sequences

In order to prevent cross-hybridisation between the amplification products, it is preferred that the sequences of the stuffer sequences are different and do not form hair-pins. In the tables 1-5, stuffer sequences are presented which can be used for the development of probes for each fluorescent dye, and have been verified for the absence of hairpins using Primer Designer version 2.0 (copyright 1990, 1991, Scientific and Educational software) The stuffer sequences are assembled from randomly chosen tetramer blocks containing one G, C, T and A, and have therefore by definition a 50% GC content. The stuffer sequence in the forward OLA probe for the two SNP alleles are kept identical to avoid preferential SNP allele amplification.

TABLE 1

Lengths of stuffer sequences

| ET-ROX and JOE probes. | | | FAM and NED probes. | | |
|---|---|---|---|---|---|
| Total stuffer length | Stuffer length 1st type probe | Stuffer length 2nd type probe | Total stuffer length | Stuffer length 1st type probe | Stuffer length 2nd type probe |
| 0 | 0 | 0 | 1 | 1 | 0 |
| 2 | 0 | 2 | 3 | 1 | 2 |
| 4 | 4 | 0 | 5 | 5 | 0 |
| 6 | 4 | 2 | 7 | 5 | 2 |
| 8 | 8 | 0 | 9 | 9 | 0 |
| 10 | 8 | 2 | 11 | 9 | 2 |
| 12 | 12 | 0 | 13 | 13 | 0 |
| 14 | 12 | 2 | 15 | 13 | 2 |
| 16 | 16 | 0 | 17 | 17 | 0 |
| 18 | 16 | 2 | 19 | 17 | 2 |
| 20 | 20 | 0 | 21 | 21 | 0 |
| 22 | 20 | 2 | 23 | 21 | 2 |
| 24 | 24 | 0 | 25 | 25 | 0 |
| 26 | 24 | 2 | 27 | 25 | 2 |
| 28 | 28 | 0 | 29 | 29 | 0 |
| 30 | 28 | 2 | 31 | 29 | 2 |
| 32 | 32 | 0 | 33 | 33 | 0 |
| 34 | 32 | 2 | 35 | 33 | 2 |
| 36 | 36 | 0 | 37 | 37 | 0 |
| 38 | 36 | 2 | 39 | 37 | 2 |

TABLE 2

Stuffer sequences for ET-ROX probes (5'-3'). Stuffer length

| 1st type probe | SEQ ID NO | 2nd type probe |
|---|---|---|
| 0 | | 0 |
| 0 | | 2 CA |
| 4 TGCA | | 0 |
| 4 TGCA | | 2 CA |
| 8 ACGT TACG | | 0 |
| 8 ACGT TACG | | 2 CA |
| 12 TAGC GTCA GCAT | 41 | 0 |
| 12 TAGC GTCA GCAT | 41 | 2 CA |
| 16 CATG GCAT ACGT TACG | 42 | 0 |
| 16 CATG GCAT ACGT TACG | 42 | 2 CA |
| 20 GATC GCTA ACGT TACG GCAT | 43 | 0 |
| 20 GATC GCTA ACGT TACG GCAT | 43 | 2 CA |
| 24 TCGA GATC ACGT CATG CTGA GCAT | 44 | 0 |

TABLE 2-continued

Stuffer sequences for ET-ROX probes (5'-3'). Stuffer length

| 1st type probe | SEQ ID NO | 2nd type probe |
|---|---|---|
| 24 TCGA GATC ACGT CATG CTGA GCAT | 44 | 2 CA |
| 28 CAGT TCAG GCAT TCGA CTAG CGTA TACG | 45 | 0 |
| 28 CAGT TCAG GCAT TCGA CTAG CGTA TACG | 45 | 2 CA |
| 32 GTCA ATCG GACT CTGA GACT CATG CGAT GACT | 0 | 46 |
| 32 GTCA ATCG GACT CTGA GACT CATG CGAT GACT | 46 | 2 CA |
| 36 GATC CGAT CGAT ATCG ACGT AGCT GCAT CGTA ATCG | 47 | 0 |
| 36 GATC CGAT CGAT ATCG ACGT AGCT GCAT CGTA ATCG | 47 | 2 CA |

TABLE 3

Stuffer sequences for JOE probes (5'-3'). Stuffer length

| First type probe | SEQ ID NO | 2nd type probe |
|---|---|---|
| 0 | | 0 |
| 0 | | 2 TG |
| 4 ACTG | | 0 |
| 4 ACTG | | 2 TG |
| 8 GCAT CAGT | | 0 |
| 8 GCAT CAGT | | 2 TG |
| 12 ATCG GCAT TACG | 50 | 0 |
| 12 ATCG GCAT TACG | 50 | 2 TG |
| 16 TACG GCAT AGTC ACGT | 51 | 0 |
| 16 TACG GCAT AGTC ACGT | 51 | 2 TG |
| 20 GATC GCTA ACGT TACG GCAT | 52 | 0 |
| 20 GATC GCTA ACGT TACG GCAT | 52 | 2 TG |
| 24 CTAG ATGC TCAG GCTA TCGA CATG | 53 | 0 |
| 24 CTAG ATGC TCAG GCTA TCGA CATG | 53 | 2 TG |
| 28 GTAC CGAT ACGT TAGC GACT TAGC CGTA | 54 | 0 |
| 28 GTAC CGAT ACGT TAGC GACT TAGC CGTA | 54 | 2 TG |
| 32 CGTA ATCG GATC CGTA ACGT GCAT ATGC CAGT | 55 | 0 |
| 32 CGTA ATCG GATC CGTA ACGT GCAT ATGC CAGT | 55 | 2 TG |

TABLE 3-continued

Stuffer sequences for JOE probes (5'-3').

| First type probe | SEQ ID NO | Stuffer length 2nd type probe |
|---|---|---|
| 36 GACT TCGA GATC TGCA ACGT ACGT CGTA AGCT GCTA | 56 | 0 |
| 36 GACT TCGA GATC TGCA ACGT ACGT CGTA AGCT GCTA | 56 | 2 TG |

TABLE 4

Stuffer sequences for FAM probes (5'-3').

| First type probe | SEQ ID NO | Stuffer length 2nd type probe |
|---|---|---|
| 1 C | | 0 |
| 1 C | | 2 GA |
| 5 C GACT | | 0 |
| 5 C GACT | | 2 GA |
| 9 C CGAT TAGC | | 0 |
| 9 C CGAT TAGC | | 2 GA |
| 13 C ATCG GATC AGCT | 59 | 0 |
| 13 C ATCG GATC AGCT | 59 | 2 GA |
| 17 C ATGC TAGC ACGT ACTG | 60 | 0 |
| 17 C ATGC TAGC ACGT ACTG | 60 | 2 GA |
| 21 C GTAC CAGT CATG GATC CGAT | 61 | 0 |
| 21 C GTAC CAGT CATG GATC CGAT | 61 | 2 GA |
| 25 C GATC ATCG ACTG GTAC TACG GACT | 62 | 0 |
| 25 C GATC ATCG ACTG GTAC TACG GACT | 62 | 2 GA |
| 29 C GTAC GCAT GCTA ACGT TACG GACT ATCG | 63 | 0 |
| 29 C GTAC GCAT GCTA ACGT TACG GACT ATCG | 63 | 2 GA |
| 33 C CGTA GCAT CGAT ATCG GTCA ACTG GATC AGCT | 64 | 0 |
| 33 C CGTA GCAT CGAT ATCG GTCA ACTG GATC AGCT | 64 | 2 GA |
| 37 C GTAC CATG TCGA CGTA GATC CGTA TAGC ACTG AGTC | 65 | 0 |
| 37 C GTAC CATG TCGA CGTA GATC CGTA TAGC ACTG AGTC | 65 | 2 GA |

TABLE 5

Stuffer sequences for NED probes (5'-3').

| First type probe | SEQ ID NO | Stuffer length 2nd type probe |
|---|---|---|
| 1 C | | 0 |
| 1 C | | 2 TC |
| 5 C GTAC | | 0 |
| 5 C GTAC | | 2 TC |
| 9 C GCAT TCGA | | 0 |
| 9 C GCAT TCGA | | 2 TC |
| 13 C ATCG GCAT GACT | 68 | 0 |
| 13 C ATCG GCAT GACT | 68 | 2 TC |
| 17 C GTCA ATGC ACGT TACG | 69 | 0 |
| 17 C GTCA ATGC ACGT TACG | 69 | 2 TC |
| 21 C GCAT CGAT AGCT CTGA ACGT | 70 | 0 |
| 21 C GCAT CGAT AGCT CTGA ACGT | 70 | 2 TC |
| 25 C GCAT ATCG GATC GATC GCAT ACGT | 71 | 0 |
| 25 C GCAT ATCG GATC GATC GCTA ACGT | 71 | 2 TC |
| 29 C ATCG GATC CATG CGTA GCAT ATCG ACGT | 72 | 0 |
| 29 C ATCG GATC CATG CGTA GCAT ATCG ACGT | 72 | 2 TC |
| 33 C TGCA AGTC CGAT TACG ATCG ACGT GCTA TGCA | 73 | 0 |
| 33 C TGCA AGTC CGAT TACG ATCG ACGT GCTA TGCA | 73 | 2 TC |
| 37 C AGCT CAGT ATCG AGTC GACT ACGT TGCA TACG GATC | 74 | 0 |
| 37 C AGCT CAGT ATCG AGTC GACT ACGT TGCA TACG GATC | 74 | 2 TC |

II. Examples Multiplex Ligation Assay and Detection

Example 1

Description of Biological Materials and DNA Isolation

Recombinant Inbred (RI) lines generated from a cross between the *Arabidopsis* ecotypes Colombia and Landsberg erecta (Lister and Dean, Plant Journal, 4, pp 745-750, (1993) were used. Seeds from the parental and RI lines were obtained from the Nottingham Arabidopsis Stock Centre.

DNA was isolated from leaf material of individual seedlings using methods known per se, for instance essentially as described in EP-0534858, and stored in 1×TE (10 mM Tris-HCl pH 8.0 containing 1 mM EDTA) solution. Concentrations were determined by UV measurements in a spectrophotometer (MERK) using standard procedures, and adjusted to 100 ng/μl using 1×TE.

Example 2

Selection of *Arabidopsis* SNP's

The *Arabidopsis* SNP's that were selected from *The Arabidopsis Information Resource* (TAIR) website: http://www.arabidopsis.org/SNPs.html:, are summarised in Table 6 in

TABLE 6

Selected SNPs from *Arabidopsis thaliana*.

|    | SNP       | SNP alleles* | RI Map position |
|----|-----------|--------------|-----------------|
| 1  | SGCSNP1   | G/A          | chr. 2; 72, 81  |
| 2  | SGCSNP20  | A/C          | chr. 4; 15, 69  |
| 3  | SGCSNP27  | T/G          | chr. 3; 74, 81  |
| 4  | SGCSNP37  | C/G          | chr 2; 72, 45   |
| 5  | SGCSNP39  | T/C          | chr. 5; 39, 64  |
| 6  | SGCSNP44  | A/T          | not mapped      |
| 7  | SGCSNP55  | C/A          | chr. 5; 27, 68  |
| 8  | SGCSNP69  | G/A          | chr. 1; 81, 84  |
| 9  | SGCSNP119 | A/T          | chr. 4; 62, 06  |
| 10 | SGCSNP164 | T/C          | chr. 5; 83, 73  |

TABLE 6-continued

Selected SNPs from *Arabidopsis thaliana*.

|    | SNP       | SNP alleles* | RI Map position |
|----|-----------|--------------|-----------------|
| 11 | SGCSNP209 | C/G          | chr. 1; 70, 31  |
| 12 | SGCSNP312 | G/T          | chr. 4; 55, 95  |

*For all SNP's the allele preceding the backslash is the Colombia allele.

Example 3

Oligonucleotide Probe Design for Oligonucleotide Ligation Reaction

The oligonucleotide probes (5'-3' orientation) were selected to discriminate the SNP alleles for each of the twelve SNP loci described in Example 2. PCR binding regions are underlined, stuffer sequences are double underlined. Reverse primers are phosphorylated at the 5' end:. p indicates phosphorylated. The sequences are summarised in Table 7.

TABLE 7

Oligonucleotide probes for detection of Colombia and Landsberg SNPs

| SEQ. ID | Code | Nucleotide sequence |
|---|---|---|
|  | SCGSNP1 |  |
| 1 | SNPfwd001 (G allele) | CGCCAGGGTTTTCCCAGTCACGACTTCAGGACTAGTCTATACCTTGAG |
| 2 | SNPfwd002 (A allele) | CGCCAGGGTTTTCCCAGTCACGACGACTTCAGGACTAGTCTATACCTTGAA |
| 3 | SNPrev001 (Common reverse SNP001) | pCTATGTGAACCAAATTAAAGTTTACTCCTGTGTGAAATTGTTATCCGCT |
|  | SGCSNP20 |  |
| 4 | SNPfWd003 (A-allele) | CGCCAGGGTTTTCCCAGTCACGACCTGCTCTTTCCTCGCTAGCTTCAGA |
| 5 | SNPfWd004 (C-allele) | CGCCAGGGTTTTCCCAGTCACGACGACTGCTCTTTCCTCGCTAGCTTCAGC |
| 6 | SNPrev002 (common reverse SNP20): | pAGATTCGGACCTTCTCTCATAATCCGACTTCCTGTGTGAAATTGTTATCCGCT |
|  | SGCSNP27 |  |
| 7 | SNPfwd005 (T-allele) | CGCCAGGGTTTTCCCAGTCACGACGAAGAGGAGAGTGGCTACGAACTCT |
| 8 | SNPfwd006 (G-allele) | CGCCAGGGTTTTCCCAGTCACGACGAGAAGAGGAGAGTGGCTACGAACTCG |
| 9 | SNPrev003 (common reverse SNP27) | pGCGATAACTGCTCTGTAGAAAGACCCGATTAGCTCCTGTGTGAAATTGTTATCCGCT |
|  | SGCSNP37 |  |
| 10 | SNPfwd007 (C-allele) | CGCCAGGGTTTTCCCAGTCACGACAATCGGCCTAAGCAAGCTTGTTTTC |
| 11 | SNPfwd008 (G-allele) | CGCCAGGGTTTTCCCAGTCACGACGAAATCGGCCTAAGCAAGCTTGTTTTG |
| 12 | SNPrev004 (common reverse SNP37) | PTGCTATTGATATCTCTGTGCAACTCATCGGATCAGCTTCCTGTGTGAAATTGTTATCCGCT |

TABLE 7-continued

Oligonucleotide probes for detection of
Colombia and Landsberg SNPs

| SEQ. ID | Code | Nucleotide sequence |
|---|---|---|
|  | SGCSNP39 |  |
| 13 | SNPfwd009 (T-allele) | CGCCAGGGTTTTCCCAGTCACGACGATCGGAAAGATATCGGAGCTCCTT |
| 14 | SNpfwd010 (C-allele) | CGCCAGGGTTTTCCCAGTCACGACGAGATCGGAAAGATATCGGAGCTCCTC |
| 15 | SNPrev005 (common reverse SNP39) | pGTCGGTGTCAACCGATCCACGGCGCATGCTAGCACGTACTGTCCTGTGTGAAATTGTTATCCGCT |
|  | SGCSNP44 |  |
| 16 | SNPfwd001 (A-allele) | CGCCAGGGTTTTCCCAGTCACGACGAACTGGCATCAATCAGGCCTCCAA |
| 17 | SNPfwd012 (T-allele) | CGCCAGGGTTTTCCCAGTCACGACGAGAACTGGCATCAATCAGGCCTCCAT |
| 18 | SNPrev006 (common reverse SNP44) | pCCTTAATGCAAGGGCTTATTACGTCGTACCAGTCATGGATCCGATTCCTGTGTGAAATTGTTATCCGCT |
|  | SGCSNP55: |  |
| 19 | SNPfwd013 (C-allele) | CGCCAGGGTTTTCCCAGTCACGACGGACTCCAAGGTATTGTTAGGCGCC |
| 20 | SNPfwd014 (A-allele) | CGCCAGGGTTTTCCCAGTCACGACGAGGACTCCAAGGTATTGTTAGGCGCA |
| 21 | SNPrev007 (common reverse SNP55) | pAACCACCAAGATCAGTCTCATCTTCGATCATCGACTGGTACTACGGACTTCCTGTGTGAAATTGTTATCCGCT |
|  | SGCSNP69 |  |
| 22 | SNPfwd015 (G-allele) | CGCCAGGGTTTTCCCAGTCACGACCATCTCTTGCGCCTTCTCAGTGTTG |
| 23 | SNPfwd016 (A-allele) | CGCCAGGGTTTTCCCAGTCACGACGACATCTCTTGCGCCTTCTCAGTGTTA |
| 24 | SNPrev008 (common reverse SNP69) | pTGACGTCCGTCGAAGAATAGGTAACGTACGCATGCTAACGTTACGGACTATCGTCCTGTGTGAAATTGTTATCCGCT |
|  | SGCSNP119 |  |
| 25 | SNPfwd017 (A-allele) | CGCCAGGGTTTTCCCAGTCACGACAGTTTCAAAACCCATGACGCTTCTA |
| 26 | SNPfwd018 (T-allele) | CGCCAGGGTTTTCCCAGTCACGACGAAGTTTCAAAACCCATGACGCTTCTT |
| 27 | SNPrev009 (common reverse SNP119) | pGTGATAGCTGAAAAGACCCATTCTCCGTAGCATCGATATCGGTCAACTGGATCAGCTTCCTGTGTGAAATTGTTATCCGCT |
|  | SGCSNP164 |  |
| 28 | SNPfWd019 (T-allele) | CGCCAGGGTTTTCCCAGTCACGACATACTCCAATTGCTCAGGCACAGTT |
| 29 | SNPfwd020 (C-allele) | CGCCAGGGTTTTCCCAGTCACGACGAATACTCCAATTGCTCAGGCACAGTC |
| 30 | SNPrev010 (common reverse SNP164) | pCTCCTTGTCCCACGAAGATAGTTCCGTACCATGTCGACGTAGATCCGTATAGCACTGAGTCTCCTGTGTGAAATTGTTATCCGCT |
|  | SGCSNP209 |  |
| 31 | SNPfwd021 (C-allele) | CGCCAGGGTTTTCCCAGTCACGACGTAGAGGCTCTAAACAGCTGCTTCC |
| 32 | SNPfwd022 (G-allele), | CGCCAGGGTTTTCCCAGTCACGACGAGTAGAGGCTCTAAACAGCTGCTTCG |
| 33 | SNPrev011 (common reverse SNP209) | pCTTGTTTATGCTAAGGGCCGGCTCCTCCTGTGTGAAATTGTTATCCGCT |

TABLE 7-continued

Oligonucleotide probes for detection of
Colombia and Landsberg SNPs

| SEQ. ID | Code | Nucleotide sequence |
|---|---|---|
| | SGCSNP312 | |
| 34 | SNPfwd023 (G-allele) | CGCCAGGGTTTTCCCAGTCACGACTAAGTCAGCTCCTAAGCTTCCATCG |
| 35 | SNPfwd024 (T-allele) | CGCCAGGGTTTTCCCAGTCACGACGATAAGTCAGCTCCTAAGCTTCCATCT |
| 36 | SNPrev012 (common reverse SNP312) | pAAGCCACTTCCTCCTGCTCAAGCGCGACTTCCTGTGTGAAATTGTTATCCGCT |

All oligonucleotides were purchased from MWG, Ebersberg, Germany. The concentration of the oligonucleotides was adjusted to 1 μM

Example 4

Design of the PCR Amplification Primers

The sequences of the primer used for PCR amplification were complementary to the PCR primer binding regions incorporated in the ligation probes described in Example 3. The sequences represent the so called M13 forward and M13 reverse primers. Usually the forward primer is labelled with FAM or □$^{33}$P-dATP depending on the detection platform. The sequence of the primers in 5'-3' orientation are:

[SEQ ID No.37]
M13 forward: CGCCAGGGTTTTCCCAGTCACGAC

[SEQ ID No.38]
M13 reverse: AGCGGATAACAATTTCACACAGGA

The concentration of these oligo's was adjusted to 50 ng/μl.

Example 5

Buffers and Reagents

The composition of the buffers was: Hybridisation buffer (1×), 20 mM Tris-HCl pH 8.5, 5 mM $MgCl_2$, 100 mM K.Cl, 10 mM DTT, 1 mM $NAD^+$.Ligation buffer (1×) 20 mM Tris-HCl pH 7.6, 25 mM Kac, 10 mM $MgAc_2$, 10 mM DTT, 1 mM $NAD^+$, 0.1% Triton-X100.PCR buffer (10×):10×PCR buffer (contains 15 mM $MgCl_2$). (Qiagen, Valencia, United States of America).No additions were used in the PCR

Example 6

Ligation and Amplification

Ligation Reactions:
Ligation reactions were carried out as follows: 100 ng genomic DNA (1 μl of 100 ng/μl) in 5 μl total volume was heat denatured by incubation for 5 minutes at 94° C. and cooled on ice. Next 4 fmol of each OLA forward and reverse probes described in Example 3 (36 oligonucleotides in total) were added, and the mixture was incubated for 16 hours at 60° C. Next, 1 unit of Taq Ligase (NEB) was added and the mixture was incubated for 15 minutes at 60° C.

Next, the ligase was heat-inactivated by incubation for 5× minutes at 94° C. and stored at −20° C. until further use.

PCR Amplification:
PCR reactions mixture contained 10 μl ligation mixture, 1 μl of 50 ng/μl (FAM or $^{33}$P) labelled M13 forward and reverse primer (as described in Example 4), 200 μM of each dNTP, 2.5 Units HotStarTaq Polymerase Qiagen, 5 μl 10×PCR buffer in a total volume of 50 μl.

Amplifications were carried out by thermal cycling in a Perkin Elmer 9700 thermo cycler (Perkin Elmer Cetus, Foster City, United States of America), according to the following thermal cycling profile:

Profile 1: Initial denaturation/enzyme activation 15 min at 94° C., followed by 35 cycles of: 30 sec at 94° C., 30 sec at 55° C., 1 min at 72° C., and a final extension of 2 min at 72° C., 4° C., forever.

Profile 2: Initial denaturation/enzyme activation 15 min at 94° C., followed by 35 cycles of: 5 se In case a $^{33}$P end-labelled M13 forward PCR primers was used, the labelling was carried out by kination as described in Vos et al., 1995 (Nucleic Acids Research, vol. 23: no. 21, pp. 4407-4414, 1995 and patent EP0534858).

Example 7

Radioactive Detection of 12-Plex SNPWave Products

FIG. 10 shows an electrophoretic gel from a multiplex oligonucleotide ligation assay of the 12 *Arabidopsis* SNPs listed in Example 2. Following the procedures described here-in before, using DNA of the Colombia ecotype (C), Landsberg erecta ecotype (L) or a mixture of equal amount of both ecotype (C+L) as the starting material.

FIG. 10 shows that the appropriate alleles of SNP's SNP SGCSNP164, SGCSNP119, SGCSNP69, SGCSNP29, SGC-SNP27 and SGCSNP1 are clearly observed in the Colombia sample, and the appropriate SNP alleles of SNP loci SGC-SNP164, SGCSNP119, SGCSNP69, SGCSNP29, SGC-SNP27 and SGCSNP1 are clearly observed in the Landsberg sample and that all these SNP alleles together are observed in the mixture of both samples.

This Example illustrates that at least six SNP's can be simultaneously ligated and amplified using the multiplex ligation/amplification procedure. This example further illustrates that at least 12 SNPs can be detected in one sample. The results are represented in Table 8

TABLE 8

| | SNP Name | Length | Allele | Result |
|---|---|---|---|---|
| Lan | SGCSNP164 | 136 | C | Yes |
| Col | SGCSNP164 | 134 | T | Yes |
| Lan | SGCSNP119 | 132 | T | Yes |
| Col | SGCSNP119 | 130 | A | Yes |
| Lan | SGCSNP69 | 128 | A | Yes |
| Col | SGCSNP69 | 126 | G | Yes |
| Lan | SGCSNP55 | 124 | A | No |
| Col | SGCSNP55 | 122 | C | Yes |
| Lan | SGCSNP44 | 120 | T | No |
| Col | SGCSNP44 | 118 | A | No |
| Lan | SGCSNP39 | 116 | C | No |
| Col | SGCSNP39 | 114 | T | Yes |
| Lan | SGCSNP37 | 112 | G | Yes |
| Col | SGCSNP37 | 110 | C | No |
| Lan | SGCSNP27 | 108 | G | Yes |
| Col | SGCSNP27 | 106 | T | Yes |
| Lan | SGCSNP20 | 104 | C | Ns* |
| Col | SGCSNP20 | 102 | A | Ns |
| Lan | SGCSNP312 | 104 | T | Ns |
| Col | SGCSNP312 | 102 | G | Ns |
| Lan | SGCSNP209 | 100 | G | Yes |
| Col | SGCSNP209 | 98 | C | Yes |
| Lan | SGCSNP1 | 100 | A | Yes |
| Col | SGCSNP1 | 97 | G | Yes |

*not scored;
Col: Colombia allele,
Lan: Landsberg allele

Example 8

Gel Electrophoresis

Gel electrophoresis was performed as described in Vos et al., Nucleic Acids research 23(21), (1995), 4407-4414. After exposure of the dried gel to phospho-imaging screens (Fuji Photo Film Co., LTD, Type BAS III) for 16 hours, an image was obtained by scanning using the Fuji scanner (Fuji Photo Film Co., LTD, Fujix BAS 2000) and stored in digital form.

Example 9

Oligonucleotide Sizers for Capillary Electrophoresis

```
sizer 94 bp:                          [SEQ ID No.39]
5'fam-ACCTACTACTGGGCTGCTTCCTAATGCAGGAGTCGCATAAGGGA
GAGCGTCGACCGATGCCCTTGAGAGCCTTCAACCCAGTCAGCTCCTTCCG sizer 95 bp: [SEQ ID No.40]
5'fam-ACCTACTACTGGGCTGCTTCCTAATGCAGGAGTCGCATAAGGGA
GAGCGTCGACCGATGCCCTTGAGAGCCTTCAACCCAGTCAGCTCCTTC
CGG sizer 137 bp:                         [SEQ ID No.41]
5'fam-ACCTACTACTGGGCTGCTTCCTAATGCAGGAGTCGCATAAGGGA
GAGCGTCGACCGATGCCCTTGAGAGCCTTCAACCCAGTCAGCTCCTTCCG
GTGGGCGCGGGGCATGACTATCGTCGCCGCACTTATGACTGTC
```

Example 10

Purification and Dilution of Amplified Connected Probes

In case of detection using the MegaBACE 1000 capillary sequencing instrument, desalting and purification of the PCR reactions mixtures was carried in 96-well format, using the following procedure:

A. Preparation of the 96-Well Sephadex Purification Plates

Dry Sephadex™ G-50 superfine (Amersham Pharmacia Biotech, Uppsala, Sweden) was loaded into the wells of a 96-well plate MultiScreen®-HV, Millipore Corporation, Bedford, Mass., USA), using the 45 microliter column loader (Millipore Corporation) as follows:

1. Sephadex G-50 superfine was added to the column loader.
2. Excess Sephadex was removed from the top of the column loader with a scraper.
3. The Multiscreen-HV plate was placed upside-down on top of the Column Loader.
4. The Multiscreen-HV plate and the Column Loader were both inverted.
5. The Sephadex G-50 was released by tapping on top or at the side of the Column Loader.

Next, the Sephadex G-50 was swollen en rinsed as follows:

6. 200 µl Milli-Q water was added per well using a multichannel pipettor.
7. A centrifuge alignment frame was placed on top of a standard 96-well microplate, the Multiscreen-HV plate was place on top and the minicolumns were packed by centrifugation for 5 min at 900 g.
8. The 96-well plate was emptied and placed back.
9. Steps 5-7 were repeated once.
10. 200 µl Milli-Q water was added to each well to swell the Sephadex G-50 and incubated for 2-3 hours. Occasionaly, at this stage the Multiscreen-HV plates with swollen mini-columns of Sephadex G-50 superfine were tightly sealed with parafilm and stored a refrigerator at 4° C. until further use.
11. A centrifuge alignment frame was placed on top of a standard 96-well microplate, the Multiscreen-HV plate was placed on top of the assembly and the minicolumns were packed by centrifugation for 5 min at 900 g.
12. The 96-well microplate was removed.
13. The mixtures containing the amplified connected probes were carefully added to the centre of each well.
14. Using the centrifuge alignment frame, the Multiscreen-HV plate was placed on top of a new standard U-bottom microtitre plate and centrifugation was carried out for 5 min at 900 g.
15. The eluate in the standard 96-well plate (approximately 25 µl per well) contains the purified product.

B. Dilution of the Purified Products

Purified samples were diluted 25-75 fold in Milli-Q water before injection.

Example 11

Capillary Electrophoresis on the MegaBACE

Preparation of the Samples:

A 800-fold dilution of ET-900 Rox size standard (Amersham Pharmacia Biotech) was made in water. 8 µl diluted ET-900 Rox was added to 2 µl purified sample. Prior to running, the sample containing the sizing standard was heat denatured by incubation for 1 min at 94° C. and subsequently put on ice.

Detection on the MegaBACE:

MegaBACE capillaries were filled with 1×LPA matrix (Amersham Pharmacia Biotech, Piscataway, N.J., USA) according to the manufacturer's instructions. Parameters for electrokinetic injection of the samples were as follows: 45 sec at 3 kV. The run parameters were 110 min at 10 kV. Post-running, the cross-talk correction, smoothing of the peaks and cross-talk correction was carried out using Genetic Profiler software, version 1.0 build 20001017 (Molecular Dynamics, Sunnyvale, Calif., USA), and electropherograms generated.

Example 12

Repeated Injection on the MegaBACE

The minimum time interval for adequate separation between two consecutively injected samples was determined by injecting the sizer sample as described in Example 8. The resulting time interval was used, with a small additional margin, when injecting the purified amplified connected probes from the oligonucleotide assay. The results are presented in FIG. 11.

A. Partial electropherogram of FAM labelled detection of the Colombia sample on a capillary electrophoretic device (MegaBACE). The same multiplex mixture was injected twice. Amplified connected probes (size range 97-134 bp) and flanking sizer fragments (94, 95 and 137 bp) are all labelled with FAM B. Partial electropherogram of FAM labelled detection of the Landsberg erecta sample on a capillary electrophoretic device (MegaBACE). The same multiplex mixture was injected twice. Amplified connected probes (size range 97-134 bp) and flanking sizer fragments (94, 95 and 137 bp) are all labelled with FAM.

Example 13

Cross-Talk Reduction Using Stuffer Sequences of Different Lengths

In this experiment the use of different length-label combinations to avoid the negative influence of incomplete cross-talk removal on the quality of a dominantly scored (presence/absence) dataset of SNP markers is demonstrated. Stuffer lengths were chosen such that ET-ROX and JOE-labelled fragments have identical sizes, and that FAM and NED fragments have identical sizes, but differing by 1 basepair from those of ET-ROX and JOE-labelled fragments. The result is that even in case of incomplete cross-talk removal between dyes with overlapping emission spectra, the observed signal will not result in incorrect scoring because the expected sizes of the amplification products are known for every label. Hence length-label combinations define the expectance patterns for genuine signals are signals originating from incomplete cross-talk correction. The results are presented in FIGS. 12 and 13.

The example shows in FIG. 13:

A). The effect of incomplete cross talk removal on the data quality in case of a sample that contains a ET-ROX labelled fragment of 120 basepair and a NED labelled fragment of 124 basepairs in a situation where fragments of a particular size can be observed in combination with all labels. In this case, incomplete cross-talk of ET-ROX signal into the FAM Channel at 120 bp removal leads to the incorrect scoring of a FAM fragment of 120 basepairs (in reality an ET-ROX labelled fragment of 120 basepairs). Similarly, incomplete cross-talk correction removal of NED signal into JOE at 124 bp leads to incorrect scoring of a JOE fragment of 124 basepairs (in reality a NED labelled fragment of 124 basepairs), in addition to the correct fragments.

B). The effect of the use of cross-talk-optimised length-label combinations such that ET-ROX- and FAM-labelled fragments of the same length are not avoided by choosing different stuffer lengths, because their emission spectra overlap. Similarly, same-size amplified connected probe fragments labelled with JOE and NED are avoided. In case of a hypothetical sample containing a 120 bp ET-ROX-labelled fragment and a 124 bp NED labelled fragment (identical to the that described above in A), the small but detectable signals (peaks) of FAM at 120 bp and of JOE at 124 bp that remain after incomplete (mathematical) cross-talk correction will not be scored because they are known to originate from cross talk of ET-ROX and NED signals, respectively. Hence, they have no impact on the data quality and both fragments are scored correctly.

Example 14

Identification of SNPs

The selected SNPs are identified and summarized in Table 9.

TABLE 9

Selected SNP sequences and position of the SNP.

| SEQ ID # | | W = A or T; M = A or C; R = A or G; Y = C or T; K = G or T; D = A, G or T; N = A, C, G or T | S = G or C; H = A, C or T; B = C, G or T; V = A, C or G; | | | |
|---|---|---|---|---|---|---|
| Set 1 | Fragment code | Locus nr. | Length | SNP position | SEQUENCE | |
| 75 | 9651-f06 | 1 | 735 | 174 | CCKCGGAGAAWTGAAGAAGTATGCTGTGTCATCCGGTGTTGGCTCACACTCAGGTACTGTTAGACCCATCT CATGCTTAACAATKKGATTCTTTGAGCGTTACCTAKTGAACTAGTATATTTTKGGTGTGCTCACTTACTGC CTCAAGTTATGTGATGGTTTCTAATTKTGACTTTAATTATAAATCATGCACATCTTATATAAATCAGATTT | |

TABLE 9-continued

Selected SNP sequences and position of the SNP.

| SEQ ID # | | | | W = A or T; M = A or C; R = A or G; Y = C or T; K = G or T; S = G or C; H = A, C or T; B = C, G or T; V = A, C or G; D = A, G or T; N = A, C, G or T |
|---|---|---|---|---|
| | | | | CCAAAGCTGCTGTATATTGGTTCAGTAGATAATATGGTTTTATCTCTTAACTGGTTATATCTGCAGTCATT TTTTGGTTATACCTCTTTCATAGTCCTGATTAAAGGATTTTGAGTTATTTTCAATGTCTCTTTGTAAACAA AGATTATACTAGAATCAATCTAATGTTTTCTTTCCTTTAAATAAATTACAGATAAGGAAGATGAAGGGTTT GAAACAGAAGAAAGCCCATTTGATGGAGATCCAGGTTAATGGAGGATCAATTGCTCAGAAGGTTGACTTCG CATATGGTTTCTTTGAGAAGCAGGTTCCAGTTGATGCTGTTTTCCAGAAGGATGAGATGATTGACATCATT GGTGTCACCAAGGGTAAGGGTTATGAAGGTGTYGTAACTCGTTGGGGTGTGACACGTCTTCTCGCAAAACC CACGGGGTCTACGTAAGGTGCTGTTGGGGC |
| 76 9372-d11 | 2 | 561 | 475 | GCYTGGGGACTAGTTCTTTTTCAGAATCATATCATCTGTAGAGAAATCAGCTGCTTTCCTGAATGTTCCTCG TCCGAAATCTAGGTTGTAAGAGTCTGTAAGACCTTCCACCAGATCAAAATCAGGTTTCCATCCTAGCTCAG CCTTTTGACTTCTCGATGGATGTAAAGAAATGCTGTAGAAATTCGATGTTAAAACCAACGAGAAGACATAGA TAGACTAGTGTTGGACAAGAATCCGATATTAAACAGACAAGCTAACAACTTCAACAGAGGGAAATAAACCAT ATTTCTTGTAGTATTTCGTTTGGACTACGATTGATTGTACAAAAATGTGTGTTAATTTTAGTGAGCATACT GATGTGTGTTTAGGAAGGGACTAGGATAAGAGGCGGTGAACATGTTGTGAATCTTCACTGATGATTCATT TAGTTTGATCATATCATTTGATTCTTTGATAAAGAATGTCTCGAATTTCAATATGAATGGTAAACAACTGA AATCAACACACTAATATTTACCTGGTCACGGAATGGGAATGCTTTCTTCTTGCCAAAAT |
| 77 9371-d06 | 6 | 827 | 164 | AGNAHKYYCVAGGCTCACDASCAGGTTGGAAAAATCATTTTGATACARAARTTGCATTTTCTGGTTATTCA GGTGATTTCCCTTCTATATGTCAAACTTATTGAAACGAGTCTTCTGAAAAATAAATGGAAAGTTATATGGA AAAASATTTCCAGGATATTGCTTAGTTTCTCATAAGTATAAAGCTTTATATGTGAACCAATTCAACAGGTA CATATATCAGAGGCCCGGGTTTCTGCTGCTTTAGATAAGCTAGCTTACATGGAAGAATTGGTTAACGATAG GCTTCTGCAAGAGAAGCACAGTAGAATCAGAATGCACGTCTTCCTCTGCAAGCACGTCAACAGGATTAT TAGACACTCCAAAAAGCAAGCAACCACGAAGAACGCTGAATGTCTCAGGTCCTGTCCAAGATTACAGTTCC CGTTTGAAGAACTTTTGGTACCCTGTTGCATTCTCCGCAGATCTTAAGAATGACACCATGGTGAGTCAATT ATCSTCATATCTGCCAGTCTCTTTAACCTAAAAGAAAGAAAACATTTGATCTAAAACACAGAAAACCATGT AGATGCAAAATTATGATGCCAAAACAAATTAACAAGCTATATGATCTACGCTCCTACTTTATGGTCTTCCA TGTATATTCTTKGGGATCTTCTAATTGATGACTGTTAACTGTATCTTTGTAGTTACCGATTGATTGCTTGC AGACACACCGGGGGTRA |
| 78 9651-b06 | 3 | 363 | 187 | AGGGAGAHTAGAMCCAGAAGTGTCACCAAGAACCTATCTTCAAGAACTACAGCTTGCCTCCTAATAAATGT GGATACCCTGGTGGTATTTTCAACCCACTCAACTTTGCACCAACTGAAGAGGCCAAGGAGAAGGAACTTGC TAATGGTAAGTGGATGTTCACTTTCTCTAAATGAYTTTATATACCTGAACCAGGCTAATTATTTTAGGTGG ATAATTTGCAGGGAGATTGGCTATGTTGGCATTTTTGGGATTTATAGTGCAGCACAATGTGACTGGGAAGG GACCTTTTGACAACCTTCTGCAGCACCTCTCTGACCCATGGCACAACACCATCATCCAAACACTCA |
| 79 9651-d02 | 5 | 247 | 125 | GACTMCTGGCTKTAATGTTGCATTGGTAGCCAAGTGACACCCCTGTTGCTCATTGCTTGAAGGTTTGGCTG ATTTGGAAGTTGCAGCTTGTCTTTGCACTGCCATTAAGGCTAATGTACTTGGGATTGTCAAATTAGATATT CCTGTTGCTCTTAGTGCTTTGGTTAGTGCTTGTGCTAAGAAAGTTCCCACAGGTTTCAAGTGTGGTTAATT AGAGTATTAATTAGCCAAGGGTGGGA |
| 80 9861-c03 | 4 | 390 | 90 | MAAAKCTAAAYYAAGGCTTKATTTKGACCAACCCTKGTAATCCATTAGGTACCATTTTAGATAGGGACACA CTTAAAAAAATCTCCACYTTCACTAACGAACATAATATCCATCTTGTTTGCGACGAAATATATGCTGCTAC CGTRTTCAATYCTCCAAAATTCGTTAGCATCGCTGAAATTATCAACGAAGATAATTGTATCAATAAAGATT TAGTACACATTGTGTCTAGTCTTTCCAAGGACTTAGGTTTTCCAGGATTTCGAGTGGGAATTGTGTACTCR TTCAACGATGATGTTGTTAACTGTGCTAGAAAAATGTCGAGTTTKGGGTCTTGTTTCGACTCAGACACAAC ATTTGCTAGCTTTCATGTTGTCTGACGATGAATT |
| 81 9861-c03 | 7 | 390 | 285 | MAAAKCTAAAYYAAGGCTTKATTTKGACCAACCCTKGTAATCCATTAGGTACCATTTTAGATAGGGACACA CTTAAAAAAATCTCCACYTTCACTAACGAACATAATATCCATCTTGTTTGCGACGAAATATATGCTGCTAC CGTRTTCAATYCTCCAAAATTCGTTAGCATCGCTGAAATTATCAACGAAGATAATTGTATCAATAAAGATT TAGTACACATTGTGTCTAGTCTTTCCAAGGACTTAGGTTTTCCAGGATTTCGAGTGGGAATTGTGTACTCR TTCAACGATGATGTTGTTAACTGTGCTAGAAAAATGTCGAGTTTKGGGTCTTGTTTCGACTCAGACACAAC ATTTGCTAGCTTTCATGTTGTCTGACGATGAATT |
| 82 9703-a03 | 10 | 491 | 267 | AGACGACMCCAMGCTAAAGGAGAAACACAAGAAGCATTTAAAAAGAACATTGAAGCAGCAACTAAGTTTCT TTTGCAAAAGATCAAGGACTTGCAATTGTATGTCCATTTTAAATTGTTTTATGACATTGTCTAAGCTATTT CTTACTGAAGTTGAATGTGTTTTGTTTTCCTTCTACTTCATACCTGGCACCTTTAATAGAAACTGATACTA TTTGTGTGTGTGCTGGCAGCTTTGTTGGTGAGAGCATGCATGATGATGGCGCCCTGGTGTTTGCGTACTAC |

TABLE 9-continued

Selected SNP sequences and position of the SNP.

| SEQ ID # | | | | W = A or T; M = A or C; R = A or G; Y = C or T; K = G or T; S = G or C; H = A, C or T; B = C, G or T; V = A, C or G; D = A, G or T; N = A, C, G or T |
|---|---|---|---|---|
| | | | | AAGGAGGGTTCAGCTGATCCTACCTTTTTGTACATTGCACCTGGTTTGAAGGAGATCAAGTGCTAGATGTC TGGTGGAGTGCTTCTGCTAGAAGTTTTGCATTCGAGATTATGTTTCATGTAGTTTTTAATATTTGGTCTTT TTTGCTTATTTATGTCTGGTGTTTCTTCTAAACCTTGGGTACTTGCTGTGACCAGTACCGGAA |
| 83 | 9651-f04 | 9 | 842 | 182 | TGGGGGYYCATTACACAAAACAAGAACTTCAGCCATTGTGTGTTGTTCAAACCAAACCCCGTGGTTTCTAA TTCAACAGAGGAAAGTTCTTCTTCATTAAAGGCATTCTCTGCAGCACTTGCGTTTGTCTTCTATTCTTTTG TCAGCACCAGTTCTTCCAGCTTCTGCTGACATCTCTGGCTTACACCTTGCAAGGACTCAAAACAGTTTGCT AAAAGGGAGAAGCAACAGATCAAGAAGCTTCAAAATTCTTTGAAACTTTATGCACCTGATAGCGCCCCTGC ACTTGCTATCAATGCCACTATTGAGAAAACTAAACGCAGGTTTGCCTTCAGTATCTTTCTTCACAATTTTC AAAAAGTTTTACTTCTTATTTGCCTATTTTKKCCCCTAGTTGATCATTTTTTTATTGTGTACTAGATAGAGAG TACTTATAGTTAAGATTTGCGGGATTCTAATCAATTTTGTTAGGGGTTTACAAATTAAAATACATAGTACA AATATAGGGTCTATGGAAAAGCTACTGAATTCGTTCGAACCCATGTTAGGAGTAGGAGTAGAAGAAGAGCT AAAAGTATTCTTKTACGAATGAAAGCATACTGTACATTAMCATTTGCTTATCAGAGAAAAGCAGATTGTTC AACTTTTCCTKGGCATATGCCGTTGAGATTAGACTAGGAAACTCCACATWGAACATACATATACCSKTTGA TACTCGAGTAAGTAAAAGTTTAATYCMTCAGACGTCCCNCACTA |
| 84 | 9371-f08 | 8 | 257 | 179 | ACACCGWGAGARGAAGATAGCTTTTACAATTCTTCGCCATGACAGGAATCTTCTTCTGAGTATGAGATCGC TTGGGCAAAAGTACCGCATAAACGACCTCGAGGAGGATAACGCCGCGCTCAAGGAAGAACAAGAAGGGCTC GTTCACCGAATGAACCATATCAAGCAAAGTCTACTTGCTGAAGCTGCTAGTGAGCCCACTGGTGCCTTTGC TTCCCGTCTTCGCCGCCTCTTTGGTGATGAAAGCTGAA |

| Set 2 | Fragment code | Locus nr. | Length | SNP position | SEQUENCE |
|---|---|---|---|---|---|
| 85 | 9861-e05 | 11 | 544 | 342 | AAYGGSTGTGGAYCTGGCTGCAGTGCGGCAGTGGCTGTGGAGGGTAAGTTCTTCCTAAAATATTTATATGT TACATAAATATATAACGACTTTCATTAAAAAAAAATCATAGAATCGAGATGATCTAGTTTACAGTTTAAT TTATTCCTTTCACTAAATTTAATTATCTAAATTCTTGATTTTGTATAATTAATTGCAGATGTGGGATGTAC CCCGACTTGGAGAGCACCACTACCTTTACCATCATTGAGGGTGTTGCCACCTATGAAGAAGTTAGTCTAATT TTAACATAAAAGACTTTTTCTACATTTGTTATATATGATCGGAATGATTACGAAGTAATTTTAGAATTCAT TAACAAAATTAAGAAGTTTCACTCTCGAAATTTGAATTATAACACATAAATTGAAACAGGTCACCTAAAAG ATAACTATAATGTTAGAATTAATAATATTGAAACACATAACACGTTCTATTAATATGAATTTTGTTTACCA TATTAAAGTGTATATATATATAATTTACATGAATTAATTGCG |
| 86 | 3348.2 | 12 | 596 | 126 | TGGTAAGATGTGCTTATGAGGTCTGTCGATATTCCCTTCTGAAAAGATCTTCAATCCCACTTGAAATCATA CCCATTAAACAATCAGAGTTAAGAGAAAAAGGGTTATACTGGCGTGRAAGAGGGAAATTAGAAAGCACTGA GTTTTCATTTACTCGTTTTTGACACCCCATTTGGCTAATTTTGAAGGATGGGCTATGTATTGTTGATTGT GATTTCTTGTATTTAGGGGATATTAAGGAATTGAGGGATATGGTGGATGATAAATATGCTTTAATGTGTGT ACAACATAATTATGCTCCTAAAGAAACTACTAAAATGGATGGGGCAGTACAAACTGTGTATCCTAGGAAGA ATTGGTCATCCATGGTTCTTCTATAATTGTGCGCATCCAAAGAATAAGGTCTTGACACCTGAKAKTTGTCA ATACTGAAACTGGGGCATTTTCTCCATAAGCTTTACTATGGTTGGAAKATGAGGAGATTGGGGAAGTTCCG TTCGTTKGGAACTTCCGTCGATCG |
| 87 | 9572-f05 | 13 | 660 | 177 | AARGGAGYAAGTGKGATYCTCGAATMCATTGACGAGACATTTGAAGGCCCTTCCATCTTACCTAAAGACCC TTATGATCGAGCTTTAGCTCGTTTCTGGGCTAAATTCTTCGAAGATAAGGTATATCGACTCCTTAACTTGT CTCTACTCTGTTAATTGAATATTCTAACTTAWAAATGATCAACTATACATCTCCAAAATTTATGTGGCATG TCATGAGGTGTCTACGAGACATGTTAAAGAGTTGGAGTGCTTAATTGTTAATTGAGACCAAATATTTAGAT ATGCACATTCAAAGTTAGAGTACTTATTATCGGATACAACCAAGTCAGAATGTCATTTTATATATATTATA TGTCTTGTGTAAAATTGGACTAAAGTAATAAAAATATCACATTGCCAACAATAACTTATTTGTGACTGACTA ATGTACTTCTTATTGTTGTAGAATTTATATCTTTAAAATTTTGTTGAATTYAAGTTCCAATTGTTATGTAGTG GCCATCAATGATGAAAAGTCTATTTTTCAAAGGAGAGGAGCAAGAGAAAGGTACMGAGGAAGTTAATAGAA TGTTGAAAATTCTTGATAATGAGCTCAGGGACGRAMAGTTTTTTGTTGGTAACAACTTTGGATTGKTGATG TTGTGCAATGCTGTA |
| 88 | 9682-a05 | 14 | 370 | 201 | AAAGKGGCAGAATTAGAACCAGGAAGTGTCACCAAGACCTATCTTCAAGAACTACAGCTTGCCTCCTAATA AATGTGGATACCCTGGTGGTATTTTCAACCCACTCAACTTTGGCACCAAMCTGAAGAGGCCAAGGAGAAGG AACTTGCTAATGGTAAGTGGATGTTCACTTTCTCTAAATGAYTTTATATACCTGAACCAGGCTAATTATTT TAGGTGGATAATTTGCAGGGAGATTGGCTATGTTGGCATTTTTGGGATTTATAGTGCAGCACAATGTGACT GGGAAGGGACCTTTTGACAACCTCTGCAGCACCTCTCTGACCCATGGCACAACACCATCATCCAAACACA A |

TABLE 9-continued

Selected SNP sequences and position of the SNP.

| SEQ ID # | Fragment code | Locus nr. | Length | SNP position | SEQUENCE W = A or T; M = A or C; R = A or G; Y = C or T; K = G or T; S = G or C; H = A, C or T; B = C, G or T; V = A, C or G; D = A, G or T; N = A, C, G or T |
|---|---|---|---|---|---|
| 89 | 9651-b05 | 15 | 879 | 387 | GRAAGGAGGATCTGATGCTTCTGGCACAATGGGTTTAGTTTTSGCAAATTTTTGTATATCAAAAATTTACT AAATTTTTATACRCACTCTTTTCTTTTTAATCTGTTATAAAAATAATTACTTATACAATTTTATCAYTAAT CATGACATGCTCTTAATGTCACGTGTCATATTTAAGACCATGATTTTTATTAGATATACTTTTGATATATC GTAAAACTCTTTATATTGTCTAATTTCATGTTCATTCAAATATTCTACGAAATTAGAATTTGAAACTTTTG ATTTTTTTGTAGTTTTAGTCTTTTTGAGTCATCAGATTCTAAATTGATGGTATATATTAAATAAATTTGGT TGAGTCGAATATAAARTATTAGTCAAATTAGTGAATTCTGTCAAACTCGCTTCTTATCTTTTAGCTTTATC TATCCCTTCGTAAAATAATAGTGAAACATATATGAATTTTTTTTAATAGTCTAAATTTTATTTTCACGAAA ATTTTTATGCTCAATCAAATACTGTTTTACGAAATAAGATAGAAGGATAGTTATAATGACATGAATTCTGA TTATTAACAATGATTGTCTGGAACAGGGCGGTGCTTGTGGCTATGGGAACTTGTACTCAAACAGGTTATGG TACAAACACTGCTGCATTAAGTACTGCCTTTGTTCAATGATGGAGCATCATGTGGTCATGTTCCCMTTTGT GTGATTMTCATCCGATCMAWKKGTSYMTRGGRACTCYTTACATTTMCGCCTATTTGYCCCCAWKYKHYCHC KGCMCCCCBSBSSBBMHHMAHHWMHAACAACAACAAAACAATA |
| 90 | 9572-g11 | 16 | 400 | 361 | AAAGCACAGAAACAGAGATTATGAACAACATACAACCCAATTAGCCAAAAGTTCTTAGTTCTGGTTGACAT GTCAAATAAGATCCTAGGGACATAATAAATTCCAGAACACTGGTCAAATCACATCAGAATCAAACCCCAAC TACAAATAATGGATAATAAAGAAGGGAAACACAATTAATGATGTAAATTGAGTTAGACCTAACAAGTTACA CCAATGCAATGCTGCTCTCACCACCTGGAGGCTTGCGAACCCCGCCATAGAAGTCTCGAGATTCTACTTTC CCATCTGCAAATATATTGCTTCCACTCATTTCTCGCAACTTTGCTGAACTCAGGTGCTTCTCAGCTGATGT TGGAGGATTATCGCCCTTGAATATGTCATTTCCTGTGGAA |
| 91 | 9703-f12 | 17 | 310 | 145 | TTTGAACCGTTTGTRCCACYGACTTACWTTTKKGAMAAGASMCMACCAAGAGTTGAGGCTTTCTTGCRGCC ATTGCCAGTAAGGTYCTCAAAGACTACTTCAGCATCAAAACCACCAAAGTTTCAAGTGAAGGCTTCGCTTA AGSAGAAAGCTTTGACAGGACTGACAGCAGCTGCACTCACTGCTTCCATGGTCATGCCTGATGTAGCCGAA GCAGCAGAGAGTGTTTCACCATCCCTAAAGAACTTTTTGCTCAGCATTTCTGCAGGTGGAGTTGTGCTTGC TGCAATTCTTGGCGCTATAATTGGTGTTTANNAN |
| 92 | 9782-c03 | 18 | 610 | 161 | CACGASAGAGGGTTGACAGTACGGATGATTTTTTTCAAAAACAGGATATTTTTTCGATTCACTAAAGAAA ATAAAAGTGCTTTTAACCAAGTGGTTCCTGATTTTGGAGCCGTAACGAGAATGATATCATTATCTTGAGCT TGATATTGTCGTTGACATGCAATCACCCCTTGGATAAGTCTTGGTAATGCCCAAAAGCTTGATAATTATA CACATAAGATCCAACCCATCCTCTTTCTTTTGGTAGGGTAGAAAGCAATTTCTTACAATCTTCACTTACAT CATCTTCTTGTAAATATTTRTGAGGAGTTGGTGAAGAGGTTTGAGAAAGGGCTCGCAACAGAAACCAGCCG CGATGCGGCGTCGGACCAGGGGCAAGAGCACCCCAGCGAACGCATCACAACGGCCCCCTCGCNCACAATAA CAACAGNACAACACTCACACGCGGCGWAGATCCCGCCATCCCAACAACGCCCACCAANAATACAACCCCCC CCAGACCACCTTCACTACCCCACTCCACSCTTCACGGCCAACCACACACAANCAATCGAAACCACCCGGTC CACAAACGCACAAACACAACGACACCA |
| 93 | 9782-b11 | 19 | 340 | 245 | CAGAGAAGAYTTTGCACATTCAGCTCCCKGGTGAGGKGCACAGTAGAAAGTGTAAGTTCCTTTCTCACTCA AAGTGACACTGTATGTCTCCTGCTGCATTCAGAAGATCCTCTTCAGAACATGGAAATCTTACTAGCATC CACACCAGCTGGGATTTCATCTTCATCAAATACGACGTTGTGTGGGAACCCTGCATTGTTCTTGAATGTAA TTTTCTCACCAGCACTAACGCTGAAGTTCCCAGGAATAAAAGCTAGACTCCCATCATCACCACCAAGCAAC ACTTCAAGTGCCATGGCATTGCTAGCAAGCATCGCGCTAACAGCGGTGGCASMAAAAA |
| 94 | 9652-f04 | 20 | 443 | 370 | GAGAATGWWCTAATCATCCCATTCCAATGGTTTATAACAACTGGCCATAAAATAAAAACTAAAATATACG AAGGAGCATATTCCCAGAGAGTATGACATGCTCTGATCCAAGAACAAGATAAAGACATTCTAAAACTTACA ACCATCATCACTCAGAACGATTGGCATACTCTCTCCACCTTTTCATCAAGATTGATTCCAACCATAGCCTCA CCAAGCCCACAGCTAATTTCAGCCAGCAATTGTGGGTCACTGTAATGAGTCACTGCTTGCACGATGGCACG TCCCCTCTTTGCAGGGTCACCACTCTTGAAGATACCAGAACCCACGAACACGCCGTCACATCCCAACTGCA TCATAAGCGCTGCATCTGCTGGTGTCGCCACCCCACCTGCTGCAAAGTGAACCACAGGGAGCCTACCAAGT TGCTTTGT |

| Set 4 | Fragment code | Locus nr. | Length | SNP position | SEQUENCE |
|---|---|---|---|---|---|
| 95 | 43F | 31 | 472 | 246 | TATCCACTCAGGTCTCCGCAAGCCAGAAATGGGATATACACCTTGTTACGACCYTCAAGCCATCCACTACT GCAATCTGTCATGTCACAGATGTTCGGAAGATAATGTATAAGTACAACTATATAGTCGGAWTTGCATCTAG TCTAGCATTCGGAAAATGGAAGCCATGCTACTTCTAGCATAAAAAACAGCAGCTAGAAATCGTAACTCCAA TGATACGAGGAAGTATTCAGAGTTTAGAGTGAWGTACAATGCAATTTAGAGAACAAGCATCTGCACATCRA AGTTACCTAGGTCCTCAGCGCCTGATGGACTTCCAACTTGTTCAAGAAGGCGATAAAGGTCTTTCTCATTG |

TABLE 9-continued

Selected SNP sequences and position of the SNP.

| SEQ ID # | | | | W = A or T; M = A or C; R = A or G; Y = C or T; K = G or T; S = G or C; H = A, C or T; B = C, G or T; V = A, C or G; D = A, G or T; N = A, C, G or T |
|---|---|---|---|---|
| | | | | AATCCTTCAGGTGGAGAGTAGTTTTCACAAACTGCAAATGCCTCTGCACAGCGGAAAGATTGAATTAGATTTATGTTATATAGCCATTCTAGTCTTGCTTTAATGGATCTTTCTCGA |
| 9661F | 32 | 222 | 175 | CCACAGTTTCATGCTGCACCTACATGTGTAAGCAACTATCATAGCAAGTCTCGGAACAATTGGTAGGAAAAAATCMYKTAAGGATATGAAACATACTGTYCTTCTTCATCTGAGTCTGYAGAGTTAATTTTTAACTCTTGGGATAAATGCAAAGAWTTAGACATGGAKGAGTYCTTAACACGTCCAGACAAGAGGCGTAACACAGGTACACCTTTTCTCGA |
| 9764F | 33 | 133 | 121 | TTGTGCTTGATGAATTGTAGGTCCAGTGCAGGTTTGCTTCTAAAACAGGGAGCACTTTGCAAGTGGTGAAAGTTCTATTAGCTGGGAAAGTGTAGTTTGAGCAGTTTTGAGCTGARTTAACAAGAAAAATCGA |
| 9875F | 34 | 250 | 47 | CCGCCACTGGGTAATTGAGTTTCATATTGATGGTTTTGTTTTGTTRACGCTTCTTCCTTGTTGAGAGGGTTCAATGGAGAGATTCTATCTCGTCCTCCATTAGTTGAAGCTATTGCCTTTGATCCTATCCTTTCAAAGGYCAAGATGATTGCAGATAATTGGAATCCATTAACCAATGATTCTACGAAAATTTATTCCCTCACTGGAGGAGATGGGCAGAGATAAATATGAGATTTTGTGATGACAT |
| 9992R | 35 | 284 | 84 | TCGAGTAAGGCGGATGGATATGGAACAAGCCATTTCAAGGAGCAATTTCCCAGGATTTTCAGCTTTGCAACAGCAGAAGTGTAYCTCTGCAGAGATAGATCATAACCTTTGGAAAGGTGTAGTAATTGTCAAAGGGAGGAATGAGCCAGGAAACTGATAGACTATGTTGCGAAAATAAGCTATACTTCACTAAAAAAGGCTAGACGTTTGAGAAATGAAGCAAGAACTAACACCTCTCACCAATTGCATCATTTTCTTAGTTCAGTTGATGTGATGAGCTTGT |
| 10028R | 36 | 320 | 31 | TCGATATCCWCTCTTGTTTGTTGCAGGAGCWGAACTATAAATTGCTTGCAGGAACCTTGACATATGCTTTCTGTTGAGACTTGAATCACCAGCATGGATTTGAATGCCTTGCCACAGCCAGAGGATGACGAYGAGATTTTTGGACAACAATTAGAAGATGAACCACAAGAACCTATTTTACGTAGTGATGAGCSTGCAGATTATGTCACGAGTGCTGTAGAGATTTCACGTCGCGTATGTTTCTGCTTATACTGCTCGCTGTATCAACTATTGAACYGTACTACTACTTGARCTTGCTCGTTTATTGGATATTTCTTTTT |
| 10114446E10 | 40 | 193 | 159 | GAATTCACACTASGTTCGATGAAATTGAAACGTTCTCTTTCTGAAGAAKATACACAAGAAAAAATCTTATAGTCCTCAACAATATTCTTCTTCGTAACAGAAAACACGGAAGAAATCTCTTCTGAAAATCCCTATAATCACTGGCTGGAACTTCTCCSAACTCTCAATTTTTCAACCTTCTCTATGTTAA |
| 10214447C06 | 38 | 291 | 89 | CTGCAGAADTACTGTTTGTTCAGGACTTACTAAATATCCTAAACAAAATTGATGATAGAGCCAATAATGTATGCATGATTGGCGGTCCRTTCTTTTGTTATAGCAAGAGCTTGAAGCTAATTTTGTTTGTCATAATGGCCGCACTAATTGTTTATTATCTCAGAATGAACAAAAAGAAGCAAGTCAGAAGCTTTSTACTCTATACTGAACAACTTTTGGATTGGAACTATGTACTTATCTAGCCACGCCTCATAGATCTTTGTGGTTTAGGAGTGTTAA |
| 10314446E01 | 39 | 337 | 122 | GAATTCACAATGAAAAAKGKDGTAAAAACACGAAATCAATCAAGCATGCAAGAGATAATGTTGTCCATCCAGTTGTTGTTGATGTTTCGGTATTGTATGTGTGTTGGGAGGAGTTATCTGGRCAGCAAGTCGAGGTTTGAACGTCAAAAAGGTATGGGTTGTCTTCTCTCTTTGTCCCTTTTCGAAGAGACCCCTAAGGTTCAGACGAATCTATTCCAAAAACTAGGGTTGTTCCTTGTTGCATCTCCTTKTCACAAGCTCCCATCGCATCATAAGTAGGGTATGTTTGATGGTAGAATTTACGGATGTAATTTACTTTTGAAATGATTATGTTAA |
| 10414157A04 | 37 | 373 | 63 | AGAGAGACGAGAGCTCGACTAGTGATAGTGTTATGTGCAACAGTTGAATAGAAAGATGYACACGAGCCTCGGATCAATGGCAGGGAAAGAGGCGTGGTGCTACGAACCATAAAGGCAAGGTTGAGCTTTCCTTTACAGAGTACATCGCCTATTCCATACTCCGCTGATACTCTTTGATAAATCAAAATCTGTGGTGATCTCGTAGTTCTTGGGGATCCCAGCCAAAACCACCTTCGAGGTTCAACACAACATAGACAGTATGGCAGAATATCAAGACAATGACTGCTCGAAACTGCTGATGGCATTATGTGCAACCGTTGAATAGAGAGATGTACACGAGTCTCGGATCAATGGCAGGAAAAGAGAGTGCTTG |

| Set 5 | Fragment code | Locus nr. | Length | SNP position | SEQUENCE |
|---|---|---|---|---|---|
| 105 | 14446E01 | 41 | 337 | 252 | GAATTCACAATGAAAAAKGKDGTAAAAACACGAAATCAATCAAGCATGCAAGAGATAATGTTGTCCATCCAGTTGTTGTTGATGTTTCGGTATTGTATGTGTGTTGGGAGGAGTTATCTGGRCAGCAAGTCGAGGTTTGAACGTCAAAAAGGTATGGGTTGTCTTCTCTCTTTGTCCCTTTTCGAAGAGACCCCTAAGGTTCAGACGAATCTATTCCAAAAACTAGGGTTGTTCCTTGTTGCATCTCCTTKTCACAAGCTCCCATCGCATCATAAGTAGGGTATGTTTGATGGTAGAATTTACGGATGTAATTTACTTTTGAAATGATTATGTTAA |

TABLE 9-continued

Selected SNP sequences and position of the SNP.

| SEQ ID # | | | W = A or T; M = A or C; R = A or G; Y = C or T; K = G or T; S = G or C; H = A, C or T; B = C, G or T; V = A, C or G; D = A, G or T; N = A, C, G or T |
|---|---|---|---|
| 10615091F12 | 42 | 264 | 215 CTGCAGAATTTGACTTACATTTTCCTAATGAATCTGATGATAAGGTGCTAGATGATCYTASTKTGTATCAG AAGCTAGTAGGAAGGTTGCTTTATCTGACAATAACAAGACCAGACATAGYTTTYGYAGTGYAGCTCTTGAG TCAGTTCATGCATAGTCCTAAAGCATCTTACATGSAAGCTGMAATGRRGGTGGTAAGATATGTCAAGCAGG CACCAGGACTGGGTATACTTATGGCAGCCAATACAACTGATCAGTTAA |
| 10715089D06 | 43 | 451 | 393 CTGCAGATGGTGGTGACATTACAGGAGGTGGTGCAACCAGCCCAAAAGGCGGGATCGTAATGTTATGATCA CAAGGTGGAGGCACAGGAAGACTGGTATTATTATGTTCAGATGGCAAAGTGGCACCTTCCAGGACTTGATC AATGCCATGGCATCTGATGGAAGCACTTTTAGTGCAGATATTTGGACTAACGACTCGAGCATHGTTGAGAA ACAAATGCATGTATCCAGAATTGTTGACTCTGAGGAAAAGGTCAGGTTTTGAAGTTGGTATCATGGATCCT GTTGGGAAGTGTTGGAGGTGGTCAAAAAGCAACGGTGATGGTAAGGAATGTCGTTGCAAGAAATCTACCAC GTTGTTTTCTTGTATTAGTGTTTGGGACAGTGTCTTRTCTCTTGGCATCAAGAAAGTGATGTTTCCTTTTA CAAGGTCATCAGGGGCCATGTTAA |
| 10814447D01 | 44 | 124 | 98 CTGCAGAASCAGTACATAGGTTGTATTGAACCTGTATTTACAATAAGGAGACTCTARTGATACCGACCTA TCCCTATAATGAGTCTAAGACATCAAYGATAGAGAYGRTACCATTAGAGTTAA |
| 109257F | 45 | 149 | 50 GACAAGTAATGGTTCTAAGTTGAGGGTGTTGATGTGCTAYGAAATATTGRGACATTTGATGTTTGATAAGT ATAAGTATGAACTAATACTAAATTAAGTGAAGTTTTTATGATTTGRTATTTTGTTGAATGTGTAAGCAAA ATCTCGA |
| 11015090H06 | 46 | 267 | 90 CTGCAGAAAGTGATTCGGTTGGAGATGCAGTTACACGAAGCACTCTTACATCGGCTTCTGCTGGGGTAGAC AAATATGCTTCGACTAACTGTCCACATTCTGCTTCTTCATTTGATTATGTTGTCAGTACATTTGATGAGGG ACATCATCAGACAAAAGTCTTCAGCTCTTTGGATTGTCACAAGGAGTCAAAAATATCTAATACTAACAAGA AAAGGAGACGGTCTGGTGATAGTCATAAGCCCAGACCACGAGATAGGCAGTTAA |
| 11115091H02 | 47 | 211 | 168 CTGCAGAAGTCACACTGAASTCATACCAAAGACCATTTCAACTGCTAACATTAGACTAGAAGAGAACCTTC CATGACTGCCACAGCTTTCCCTCTCAGAMATACCCTCTGCTTCTCATCGTCTAGATGCAGTTTCACGACGC CACCTCTAGGTGAGGCCTGGACCAYAATACAATAAAATCAATAGGGCAAAAGAGAACTATGAGGTTAA |
| 11215091A10 | 48 | 165 | 113 CTGCAGAAAGATATAGCCAGAGGAAGGTGGAGCAATTTCATGTGGATAGGWTGCATAATGCATGTTCTTWC TTTATTTCGTATCTTGGTGAAGCATAGATATAGACAGATCAMAGAAGCACATYGGGATCTACCACCTACCA AGATGCTCTCATTTTACAGTTAA |
| 11314157A04 | 49 | 373 | 63 AGAGAGACGAGAGCTCGACTAGTGATAGTGTTATGTGCAACAGTTGAATAGAAAGATGYACACGAGCCTCG GATCAATGGCAGGGAAAGAGGCGTGGTGCTACGAACCATAAAGGCAAGGTTGAGCTTTCCTTTACAGAGTA CATCGCCTATTCCATACTCCGCTGATACTCTTTGATAAATCAAAATCTGTGGTGATCTCGTAGTTCTTGGG GATCCCAGCCAAAACACCTTCGAGGTTCAACACAACATAGACAGTATGCAGAATATCAAGACAATGACT GCTCGAAACTGCTGATGGCATTATGTGCAACCGTTGAATAGAGAGATGTACACGAGTCTCGGATCAATGGC AGGAAAAGAGAGTGCTTG |
| 11415091F09 | 50 | 312 | 47 CTGCAGAATGGATATTTCAATCTTTGCCATCAAATACTGGCTAGATCGTTGCAATCGCTCCTTGAATTGAA CAAACTCAATAACCTAAAAAAGTTCACAGATGAAGATTTTGTTACCATTGGGCTAGCTCATTGTATGATTA CTAATTTATCTTTTCGTTCACAAAKGGAACCATTAGTATTTGAAATGATCCTAAGAGAGAATCGTCATGAT AAGCAAYGTAAGTTTCTACACCAGAAAATAAATAATTGCTCCAACAAATACCCACTCAAGACTCACTTCGC AAGAACTAAGTTGTCCAGAAACAGTTAA |

Example 15

Oligonucleotide Probe Design for Oligonucleotide Ligation Reaction

The circular oligonucleotide probes (5'-3' orientation) were selected to discriminate the SNP alleles for each of the SNP loci described in Example 14. PCR binding regions are underlined, stuffer sequences are double underlined. Reverse primers are phosphorylated at the 5' end:. p indicates phosphorylated. The sequences are summarised in Table 10.

TABLE 10

Oligonucleotide probes for detection of SNPs from Table 9.

| SEQ ID # Set 1 AFLP + 1nr. | Padlock nr. | Fragment code | Locus nr. | Length (bp) | 5'-PH-3' |
|---|---|---|---|---|---|
| 115 | 02W561 | 9651-f06 | 1 | 124 | CACATACTTGAGGCAGTAAGTGAGTGAATTGGTACGCAGTCGATGAGTCCTGAGTAAAGTCAGGC ATTCGACTAGCGTATACGCAGATCCGATCGATTTATAATTAAAGTCAAATTAGAAACCA |
| 116 | 02W562 | 9651-f06 | 1 | 122 | CACATACTTGAGGCAGTAAGTGAGTGAATTGGTACGCAGTCGATGAGTCCTGAGTAAAGTCAGGC ATTCGACTAGCGTATACGGATCCGATCGATTTATAATTAAAGTCAAATTAGAAACCT |
| 117 | 02W563 | 9372-d11 | 2 | 119 | AAATTCGAGACATTCTTTATCAAAGGTGAATTGGTACGCAGTCGATGAGTCCTGAGTAAAGCATC GACTGGTACTACGGACTCAGATCCGATGATTTCAGTTGTTTACCATTCATATTG |
| 118 | 02W564 | 9372-d11 | 2 | 117 | AATATGAATGGTAAACAACTGAAATCGTGAATTGGTACGCAGTCGATGAGTCCTGAGTAAAGCAT CGACTGGTACTACGGACTGATCCGATCTTTGATAAAGAATGTCTCGAATTTT |
| 119 | 02W565 | 9371-d06 | 6 | 114 | ATTTCCAGGATATTGCTTAGTTTCTGTGAATTGGTACGCAGTCGATGAGTCCTGAGTAAAGTCAG TCATGGATCCGATCAGATCCGAAATAAATGGAAAGTTATATGGAAAAAC |
| 120 | 02W566 | 9371-d06 | 6 | 112 | ATTTCCAGGATATTGCTTAGTTTCTGTGAATTGGTACGCAGTCGATGAGTCCTGAGTAAAGTCAG TCATGGATCCGATGATCCGAAATAAATGGAAAGTTATATGGAAAAAG |
| 121 | 02W567 | 9651-b06 | 3 | 109 | TTTATATACCTGAACCAGGCTAATTAGTGAATTGGTACGCAGTCGATGAGTCCTGAGTAAAGTCT AACGTTACGGCATGATCCGTGGATGTTCACTTTCTCTAAATGAC |
| 122 | 02W568 | 9651-b06 | 3 | 107 | TTTATATACCTGAACCAGGCTAATTAGTGAATTGGTACGCAGTCGATGAGTCCTGAGTAAAGTCT AACGTTACGGCATGATCTGGATGTTCACTTTCTCTAAATGAT |
| 123 | 02W569 | 9651-d02 | 5 | 104 | CTTGGGATTGTCAAATTAGATATTCCGTGAATTGGTACGCAGTCGATGAGTCCTGAGTAAAGTGA TCAGCTGATCCGATCTGCACTGCCATTAAGGCTAATGTA |
| 124 | 02W570 | 9651-d02 | 5 | 102 | CTTGGGATTGTCAAATTAGATATTCCGTGAATTGGTACGCAGTCGATGAGTCCTGAGTAAAGTGA TCAGCTGATCCGATGCACTGCCATTAAGGCTAATGTG |
| 125 | 02W571 | 9861-c03 | 4 | 99 | TTCACTAACGAACATAATATCCATCTGTGAATTGGTACGCAGTCGATGAGTCCTGAGTAAAGTCA TACGTTACGGGACACACTTAAAAAAATCTCCACC |
| 126 | 02W572 | 9861-c03 | 4 | 97 | TTCACTAACGAACATAATATCCATCTGTGAATTGGTACGCAGTCGATGAGTCCTGAGTAAAGTCA TACGTTAGGACACACTTAAAAAAATCTCCACT |
| 127 | 02W573 | 9861-c03 | 7 | 94 | TTCAACGATGATGTTGTTAACTGTGGTGAATTGGTACGCAGTCGATGAGTCCTGAGTAAAGTAGT CAGATTTTCGAGTGGGAATTGTGTACTCG |
| 128 | 02W574 | 9861-c03 | 7 | 92 | TTCAACGATGATGTTGTTAACTGTGGTGAATTGGTACGCAGTCGATGAGTCCTGAGTAAAGTAGT GATTTTCGAGTGGGAATTGTGTACTCA |
| 129 | 02W575 | 9703-a03 | 10 | 89 | GCCCTGGTGTTTGCGTACTACAGTGAATTGGTACGCAGTCGATGAGTCCTGAGTAAAGTTCAGCA TGTGAGAGCATGCATGATGATGGC |
| 130 | 02W576 | 9703-a03 | 10 | 87 | CCATCATCATGCATGCTCTCACGTGAATTGGTACGCAGTCGATGAGTCCTGAGTAAAGTTCAGCT GTAGTACGCAAACACCAGGGCA |
| 131 | 02W577 | 9651-f04 | 9 | 84 | AAGCTGGAAGAACTGGTGCTGGTGAATTGGTACGCAGTCGATGAGTCCTGAGTAAAGTAGGTGTA AGCCCAGAGATGTCAGCAG |
| 132 | 02W578 | 9651-f04 | 9 | 82 | TGCTGACATCTCTGGGCTTACACGTGAATTGGTACGCAGTCGATGAGTCCTGAGTAAAGGCAGCA CCAGTTCTTCCAGCTTG |
| 133 | 02W579 | 9371-f08 | 8 | 79 | CTACTTGCTGAAGCTGCTAGTGAATTGGTACGCAGTCGATGAGTCCTGAGTAAAGCGAATGAACC ATATCAAGCAAAGT |

TABLE 10-continued

Oligonucleotide probes for detection of SNPs from Table 9.

| SEQ ID # | | | | | |
|---|---|---|---|---|---|
| 134 | 02W580 | 9371-f08 | 8 | 77 | CTACTTGCTGAAGCTGCTAGTGAATTGGTACGCAGTCGATGAGTCCTGAGTAAAGAATGAACCAT ATCAAGCAAAGC |

| Set 2 AFLP + 1nr. | Padlock nr. | Fragment code | Locus nr. | Length (bp) | 5'-PH-3' |
|---|---|---|---|---|---|
| 135 | 02W581 | 9861-e05 | 11 | 124 | AGTAATTTTAGAATTCATTAACAAAATTACCGAATTGGTACGCAGTCGATGAGTCCTGAGTAATG CGATTAGCGATACGTTAGCGACTTAGCCGTACTGTTATATATGATCGGAATGATTACGA |
| 136 | 02W582 | 9861-e05 | 11 | 122 | AGTAATTTTAGAATTCATTAACAAAATTACCGAATTGGTACGCAGTCGATGAGTCCTGAGTAATG ATTAGCGATACGTTAGCGACTTAGCCGTACTGTTATATATGATCGGAATGATTACGT |
| 137 | 02W583 | 3348.2 | 12 | 119 | AAGAGGGAAATTAGAAAGCACTGACCGAATTGGTACGCAGTCGATGAGTCCTGAGTAATGCATTC GAAATCGGACTCTGAGACTCATGCGATGACTGAAAAAGGGTTATACTGGCGTGA |
| 138 | 02W584 | 3348.2 | 12 | 117 | AAGAGGGAAATTAGAAAGCACTGACCGAATTGGTACGCAGTCGATGAGTCCTGAGTAATGTTCGA ATCGGACTCTGAGACTCATGCGATGACTGAAAAAGGGTTATACTGGCGTGG |
| 139 | 02W585 | 9572f05 | 13 | 114 | AAATGATCAACTATACATCTCCAAAACCGAATTGGTACGCAGTCGATGAGTCCTGAGTAATGATC AGTCCAGTCATGGATCCGATCACTCTGTTAATTGAATATTCTAACTTAT |
| 140 | 02W586 | 9572f05 | 13 | 112 | AAATGATCAACTATACATCTCCAAAACCGAATTGGTACGCAGTCGATGAGTCCTGAGTAATGCAG TCCAGTCATGGATCCGATCACTCTGTTAATTGAATATTCTAACTTAA |
| 141 | 02W587 | 9682a05 | 14 | 109 | TTTATATACCTGAACCAGGCTAATTACCGAATTGGTACGCAGTCGATGAGTCCTGAGTAATGCGA CTTCGCTAACGTTACGGCATGGATGTTCACTTTCTCTAAATGAC |
| 142 | 02W588 | 9682a05 | 14 | 107 | TTTATATACCTGAACCAGGCTAATTACCGAATTGGTACGCAGTCGATGAGTCCTGAGTAATGACT TCGCTAACGTTACGGCATGGATGTTCACTTTCTCTAAATGAT |
| 143 | 02W589 | 9651-b05 | 15 | 104 | TATTAGTCAAATTAGTGAATTCCGTCCCGAATTGGTACGCAGTCGATGAGTCCTGAGTAATGACT GCGGATCAGCTAAATAAATTTGTTGAGTCGAATATAAAG |
| 144 | 02W590 | 9651-b05 | 15 | 102 | TATTAGTCAAATTAGTGAATTCCGTCCCGAATTGGTACGCAGTCGATGAGTCCTGAGTAATGTGC GGATCAGCTAAATAAATTGGTTGAGTCGAATATAAAA |
| 145 | 02W591 | 9572g11 | 16 | 99 | TGGAGGATTATCGCCCTTGAATATCCGAATTGGTACGCAGTCGATGAGTCCTGAGTAATGTACTG GCATACGTTACGTCAGGTGCTTCTCAGCTGATGC |
| 146 | 02W592 | 9572g11 | 16 | 97 | TGGAGGATTATCGCCCTTGAATATCCGAATTGGTACGCAGTCGATGAGTCCTGAGTAATGCTGGC ATACGTTACGTCAGGTGCTTCTCAGCTGATGT |
| 147 | 02W593 | 9703f12 | 17 | 94 | AGAAAGCTTTGACAGGACTGACAGCCGAATTGGTACGCAGTCGATGAGTCCTGAGTAATGGTGGA TCAGCTTCAAGTGAAGGCTTCGCTTAAGC |
| 148 | 02W594 | 9703f12 | 17 | 92 | AGAAAGCTTTGACAGGACTGACAGCCGAATTGGTACGCAGTCGATGAGTCCTGAGTAATGGGATC AGCTTCAAGTGAAGGCTTCGCTTAAGG |
| 149 | 02W595 | 9782c03 | 18 | 89 | ATTGTCGTTGACATGCAATCACCCCGAATTGGTACGCAGTCGATGAGTCCTGAGTAATGCTCAAA TGATATCATTATCTTGAGCTTGAA |
| 150 | 02W596 | 9782c03 | 18 | 87 | ATTGTCGTTGACATGCAATCACCCCGAATTGGTACGCAGTCGATGAGTCCTGAGTAATGCCAATG ATATCATTATCTTGAGCTTGAT |
| 151 | 02W597 | 9782b11 | 19 | 84 | CCAGGAATAAAAGCTAGACTCCCCCGAATTGGTACGCAGTCGATGAGTCCTGAGTAATGCACACC AGCACTAACGCTGAAGTTC |
| 152 | 02W598 | 9782b11 | 19 | 82 | CCAGGAATAAAAGCTAGACTCCCCCGAATTGGTACGCAGTCGATGAGTCCTGAGTAATGCACCAG CACTAACGCTGAAGTTT |
| 153 | 02W599 | 9652-f04 | 20 | 79 | CGCTGCATCTGCTGGTGTCCCGAATTGGTACGCAGTCGATGAGTCCTGAGTAATGGTCACATCCC AACTGCATCATAAG |
| 154 | 02W600 | 9652-f04 | 20 | 77 | CGCTGCATCTGCTGGTGTCCGAATTGGTACGCAGTCGATGAGTCCTGAGTAATGTCACATCCCAA CTGCATCATAAA |

| Set 4 AFLP + 1nr. | Padlock nr. | Fragment code | Locus nr. | Length (bp) | 5'-PH-3' |
|---|---|---|---|---|---|
| 155 | 02W601 | 43F | 31 | 124 | GTACAATGCAATTTAGAGAACAAGCGGGAATTGGTACGCAGTCGATGAGTCCTGAGTAACGCTGA TCCGATCGATATCGACGTAGCTGCATCGTAATCGGGAAGTATTCAGAGTTTAGAGTGAA |
| 156 | 02W602 | 43F | 31 | 122 | GTACAATGCAATTTAGAGAACAAGCGGGAATTGGTACGCAGTCGATGAGTCCTGAGTAACGCATC CGATCGATATCGACGTAGCTGCATCGTAATCGGGAAGTATTCAGAGTTTAGAGTGAT |

TABLE 10-continued

Oligonucleotide probes for detection of SNPs from Table 9.

| SEQ ID # | | | | | |
|---|---|---|---|---|---|
| 157 | 02W603 | 61F | 32 | 119 | CTTAACACGTCCAGACAAGAGGCGGGAATTGGTACGCAGTCGATGAGTCCTGAGTAACGCACCAT GTCGACGTAGATCCGTATAGCACTGAGTCGCAAAGAATTAGACATGGATGAGTT |
| 158 | 02W604 | 61F | 32 | 117 | CTTAACACGTCCAGACAAGAGGCGGGAATTGGTACGCAGTCGATGAGTCCTGAGTAACGCCCATG TCGACGTAGATCCGTATAGCACTGAGTCCAAAGATTTAGACATGGAGGAGTC |
| 159 | 02W605 | 64F | 33 | 114 | TTAACAAGAAAAATCGGTCAGGACTGGGAATTGGTACGCAGTCGATGAGTCCTGAGTAACGCCGT ACGCATGCTAACGTTACGGACTATCTAGTTTGAGCAGTTTTGAGCTGAA |
| 160 | 02W606 | 64F | 33 | 112 | TTAACAAGAAAAATCGGTCAGGACTGGGAATTGGTACGCAGTCGATGAGTCCTGAGTAACGCTAC GCATGCTAACGTTACGGACTATCTAGTTTGAGCAGTTTTGAGCTGAG |
| 161 | 02W607 | 75F | 34 | 109 | ACGCTTCTTCCTTGTTGAGAGGGGGGAATTGGTACGCAGTCGATGAGTCCTGAGTAACGCCGATG CTCAGGCTATCGACATGTTCATATTGATGGTTTTGTTTTTGTTA |
| 162 | 02W608 | 75F | 34 | 107 | ACGCTTCTTCCTTGTTGAGAGGGGGGATTGGTACGCAGTCGATGAGTCCTGAGTAACGCATGCT CAGGCTATCGACATGTTCATATTGATGGTTTTGTTTTTGTTG |
| 163 | 02W609 | 92R | 35 | 104 | CTCTGCAGAGATAGATCATAACCTGGGAATTGGTACGCAGTCGATGAGTCCTGAGTAACGCATCA CGTCATGCTGAGCATAGCTTTGCAACAGCAGAAGTGTAT |
| 164 | 02W610 | 92R | 35 | 102 | CTCTGCAGAGATAGATCATAACCTGGGAATTGGTACGCAGTCGATGAGTCCTGAGTAACGCCACG TCATGCTGAGCATAGCTTTGCAACAGCAGAAGTGTAC |
| 165 | 02W611 | 28R | 36 | 99 | GAACTATAAATTGCTTGCAGGAACCGGGAATTGGTACGCAGTCGATGAGTCCTGAGTAACGCTCG CTAACGTTACGCTCTCTTGTTTGTTGCAGGAGCA |
| 166 | 02W612 | 28R | 36 | 97 | GAACTATAAATTGCTTGCAGGAACCGGGAATTGGTACGCAGTCGATGAGTCCTGAGTAACGCGCT AACGTTACGCACTCTTGTTTGTTGCAGGAGCT |
| 167 | 02W613 | 14446E10 | 40 | 94 | AACTCTCAATTTTTCAACCTTCTCTAGGGAATTGGTACGCAGTCGATGAGTCCTGAGTAACGCGT CATTCGAATCACTGGCTGGAACTTCTCCC |
| 168 | 02W614 | 14446E10 | 40 | 92 | AACTCTCAATTTTTCAACCTTCTCTAGGGAATTGGTACGCAGTCGATGAGTCCTGAGTAACGCCA TTCGAATCACTGGCTGGAACTTCTCCG |
| 169 | 02W615 | 14447C06 | 38 | 89 | TTCTTTTGTTATAGCAAGAGCTTGAAGGGAATTGGTACGCAGTCGATGAGTCCTGAGTAACGCCC GATGTATGCATGATTGGCGGTCCA |
| 170 | 02W616 | 14447C06 | 38 | 87 | TTCTTTTGTTATAGCAAGAGCTTGAAGGGAATTGGTACGCAGTCGATGAGTCCTGAGTAACGCCA TGTATGCATGATTGGCGGTCCG |
| 171 | 02W617 | 14446E01 | 39 | 84 | TCACAAGCTCCCATCGCATCATGGGAATTGGTACGCAGTCGATGAGTCCTGAGTAACGCTGTTGT TCCTTGTTGCATCTCCTTT |
| 172 | 02W618 | 14446E01 | 39 | 82 | TCACAAGCTCCCATCGCATCATGGGAATTGGTACGCAGTCGATGAGTCCTGAGTAACGGTTGTTC CTTGTTGCATCTCCTTG |
| 173 | 02W619 | 14157A04 | 37 | 79 | ACACGAGCCTCGGATCAATGGGAATTGGTACGCAGTCGATGAGTCCTGAGTAACGTGCAACAGTT GAATAGAAAGATGT |
| 174 | 02W620 | 14157A04 | 37 | 77 | ACACGAGCCTCGGATCAATGGGAATTGGTACGCAGTCGATGAGTCCTGAGTAACGCAACAGTTGA ATAGAAAGATGC |

| Set 5 AFLP + 1nr. | Padlock nr. | Fragment code | Locus nr. | Length (bp) | 5'-PH-3' |
|---|---|---|---|---|---|
| 175 | 02W621 | 14446E01 | 41 | 124 | TCACAAGCTCCCATCGCATCATAGAGAATTGGTACGCAGTCGATGAGTCCTGAGTAAGCGACTCG TACCATGTCGACGTAGATCCGTATAGCACTGAGTCGTTGTTCCTTGTTGCATCTCCTTG |
| 176 | 02W622 | 14446E01 | 41 | 122 | TCACAAGCTCCCATCGCATCATAGAGAATTGGTACGCAGTCGATGAGTCCTGAGTAAGCCTCGTA CCATGTCGACGTAGATCCGTATAGCACTGAGTCGTTGTTCCTTGTTGCATCTCCTTT |
| 177 | 02W623 | 15091F12 | 42 | 119 | GCACCAGGACTGGGTATACTTATGAGAATTGGTACGCAGTCGATGAGTCCTGAGTAAGCGATCCG ATCGATATCGACGTAGCTGCATCGTAATCGGAGGTGGTAAGATATGTCAAGCAG |
| 178 | 02W624 | 15091F12 | 42 | 117 | GCACCAGGACTGGGTATACTTATGAGAATTGGTACGCAGTCGATGAGTCCTGAGTAAGCTCCGAT CGATATCGACGTAGCTGCATCGTAATCGAGGGTGGTAAGATATGTCAAGCAA |
| 179 | 02W625 | 15089D06 | 43 | 114 | TCTCTTGGCATCAAGAAAGTGATGGAGAATTGGTACGCAGTCGATGAGTCCTGAGTAAGCTATCG AGTCGACTACGTTGCATACGGATCTATTAGTGTTTGGGACAGTGTCTTA |
| 180 | 02W626 | 15089D06 | 43 | 112 | TCTCTTGGCATCAAGAAAGTGATGGAGAATTGGTACGCAGTCGATGAGTCCTGAGTAAGCTCGAG TCGACTACGTTGCATACGGATCTATTAGTGTTTGGGACAGTGTCTTG |

TABLE 10-continued

Oligonucleotide probes for detection of SNPs from Table 9.

| SEQ ID # | | | | | |
|---|---|---|---|---|---|
| 181 | 02W627 | 14447D01 | 44 | 109 | GATAGAGATGGTACCATTAGAGTTAGAGAATTGGTACGCAGTCGATGAGTCCTGAGTAAGCGTAG ATCCGTATAGCACTGAGTCCCTATAATGAGTCTAAGACATCAAC |
| 182 | 02W628 | 14447D01 | 44 | 107 | GATAGAGACGATACCATTAGAGTTAGAGAATTGGTACGCAGTCGATGAGTCCTGAGTAAGCGTAG ATCCGTATAGCACTGAGCCTATAATGAGTCTAAGCATCAAT |
| 183 | 02W629 | 257F | 45 | 104 | GACATTTGATGTTTGAAGTATAAGTATGAGAATTGGTACGCAGTCGATGAGTCCTGAGTAAGCTC GACGTGCTATGCAGGTGTTGATGTGCTATGAAATATTGA |
| 184 | 02W630 | 257F | 45 | 102 | GACATTTGATGTTTGAAGTATAAGTATGAGAATTGGTACGCAGTCGATGAGTCCTGAGTAAGCCG ACGTGCTATGCAGTGTTGATGTGCTACGAAATATTGG |
| 185 | 02W631 | 15090H06 | 46 | 99 | GTCCACATTCTGCTTCTTCATTTGGAGAATTGGTACGCAGTCGATGAGTCCTGAGTAAGCGTGCA TATGCCAGTGTAGACAAATATGCTTCGACTAACT |
| 186 | 02W632 | 15090H06 | 46 | 97 | GTCCACATTCTGCTTCTTCATTTGGAGAATTGGTACGCAGTCGATGAGTCCTGAGTAAGCGCATA TGCCAGTGTAGACAAATATGCTTCGACTAACC |
| 187 | 02W633 | 15091H02 | 47 | 94 | AATACAATAAAATCAATAGGGCAAAGGAGAATTGGTACGCAGTCGATGAGTCCTGAGTAAGCCT ACGGACTCTCTAGGTGAGGCCTGGACCAT |
| 188 | 02W634 | 15091H02 | 47 | 92 | AATACAATAAAATCAATAGGGCAAAGAGAGAATTGGTACGCAGTCGATGAGTCCTGAGTAAGCAC GGACTCTCTAGGTGAGGCCTGGACCAC |
| 189 | 02W635 | 15091A10 | 48 | 89 | AGAAGCACATCGGGATCTACCACGAGAATTGGTACGCAGTCGATGAGTCCTGAGTAAGCCCGATT GAAGCATAGATATAGACAGATCAC |
| 190 | 02W636 | 15091A10 | 48 | 87 | AGAAGCACATTGGGATCTACCACGAGAATTGGTACGCAGTCGATGAGTCCTGAGTAAGCGATTGA AGCATAGATATAGACAGATCAA |
| 191 | 02W637 | 14157A04 | 49 | 84 | ACACGAGCCTCGGATCAATGGCGAGAATTGGTACGCAGTCGATGAGTCCTGAGTAAGCGGTGCAA CAGTTGAATAGAAAGATGT |
| 192 | 02W638 | 14157A04 | 49 | 82 | ACACGAGCCTCGGATCAATGGCGAGAATTGGTACGCAGTCGATGAGTCCTGAGTAAGCTGCAACA GTTGAATAGAAAGATGC |
| 193 | 02W639 | 15091F09 | 50 | 79 | GTTGCAATCGCTCCTTGAATTGAGAATTGGTACGCAGTCGATGAGTCCTGAGTAAGCGCCATCAA ATACTGGCTAGATC |
| 194 | 02W640 | 15091F09 | 50 | 77 | GTTGCAATCGCTCCTTGAATTGAGAATTGGTACGCAGTCGATGAGTCCTGAGTAAGCCATCAAAT ACTGGCTAGATT |

| Set 4 AFLP + 0 | Padlock nr. | Fragment code | Locus nr. | Length (bp) | 5'-PH-3' |
|---|---|---|---|---|---|
| 195 | 02R123 | 43F | 31 | 120 | GTACAATGCAATTTAGAGAACAAGCGGAATTGGTACGCAGTCGATGAGTCCTGAGTAAGGATCCG ATCGATATCGACGTAGCTGCATCGTAATCGGGAAGTATTCAGAGTTTAGAGTGAA |
| 196 | 02R124 | 43F | 31 | 118 | GTACAATGCAATTTAGAGAACAAGCGGAATTGGTACGCAGTCGATGAGTCCTGAGTAAGTCCGAT CGATATCGACGTAGCTGCATCGTAATCGGGAAGTATTCAGAGTTTAGAGTGAT |
| 197 | 02R125 | 61F | 32 | 116 | CTTAACACGTCCAGACAAGAGGCGGAATTGGTACGCAGTCGATGAGTCCTGAGTAAGACCATGTC GACGTAGATCCGTATAGCACTGAGTCGCAAAGAATTAGACATGGATGAGTT |
| 198 | 02R126 | 61F | 32 | 114 | CTTAACACGTCCAGACAAGAGGCGGAATTGGTACGCAGTCGATGAGTCCTGAGTAAGCCATGTCG ACGTAGATCCGTATAGCACTGAGTCCAAAGATTTAGACATGGAGGAGTC |
| 199 | 02R127 | 64F | 33 | 112 | TTAACAAGAAAAATCGGTCAGGACTGGAATTGGTACGCAGTCGATGAGTCCTGAGTAAGCGTACG CATGCTAACGTTACGGACTATCGTAGTTTGAGCAGTTTTGAGCTGAA |
| 200 | 02R128 | 64F | 33 | 110 | TTAACAAGAAAAATCGGTCAGGACTGGAATTGGTACGCAGTCGATGAGTCCTGAGTAAGTACGCA TGCTAACGTTACGGACTATCGTAGTTTGAGCAGTTTTGAGCTGAG |
| 201 | 02R129 | 75F | 34 | 108 | ACGCTTCTTCCTTGTTGAGAGGGGAATTGGTACGCAGTCGATGAGTCCTGAGTAAGCTAGATGC TCAGGCTATCGACATGTTCATATTGATGGTTTTGTTTTTGTTA |
| 202 | 02R130 | 75F | 34 | 106 | ACGCTTCTTCCTTGTTGAGAGGGGAATTGGTACGCAGTCGATGAGTCCTGAGTAAGAGATGCTC AGGCTATCGACATGTTCATATTGATGGTTTTGTTTTTGTTG |
| 203 | 02R131 | 92R | 35 | 104 | CTCTGCAGAGATAGATCATAACCTGGAATTGGTACGCAGTCGATGAGTCCTGAGTAAGGAGATCA CGTCATGCTGAGCATAGCTTTGCAACAGCAGAAGTGTAT |
| 204 | 02R132 | 92R | 35 | 102 | CTCTGCAGAGATAGATCATAACCTGGAATTGGTACGCAGTCGATGAGTCCTGAGTAAGGATCACG TCATGCTGAGCATAGCTTTGCAACAGCAGAAGTGTAC |

TABLE 10-continued

Oligonucleotide probes for detection of SNPs from Table 9.

| SEQ ID # | | | | | |
|---|---|---|---|---|---|
| 205 | 02R133 | 28R | 36 | 100 | GAACTATAAATTGCTTGCAGGAACCGGAATTGGTACGCAGTCGATGAGTCCTGAGTAAGTCGCTAACGTTACGGCATCTCTCTTGTTTGTTGCAGGAGCA |
| 206 | 02R134 | 28R | 36 | 98 | GAACTATAAATTGCTTGCAGGAACCGGAATTGGTACGCAGTCGATGAGTCCTGAGTAAGGCTAACGTTACGGCATCACTCTTGTTTGTTGCAGGAGCT |
| 207 | 02R135 | 14157A04 | 37 | 96 | ACACGAGCCTCGGATCAATGGCGGAATTGGTACGCAGTCGATGAGTCCTGAGTAAGTGCTAGCACGTACTGGTGCAACAGTTGAATAGAAAGATGT |
| 208 | 02R136 | 14157A04 | 37 | 94 | ACACGAGCCTCGGATCAATGGCGGAATTGGTACGCAGTCGATGAGTCCTGAGTAAGCTAGCACGTACTGGTGCAACAGTTGAATAGAAAGATGC |
| 209 | 02R137 | 14447C06 | 38 | 92 | TTCTTTTGTTATAGCAAGAGCTTGAAGGAATTGGTACGCAGTCGATGAGTCCTGAGTAAGCCGATTAGCATGTATGCATGATTGGCGGTCCA |
| 210 | 02R138 | 14447C06 | 38 | 90 | TTCTTTTGTTATAGCAAGAGCTTGAAGGAATTGGTACGCAGTCGATGAGTCCTGAGTAAGCCGTAGCATGTATGCATGATTGGCGGTCCG |
| 211 | 02R139 | 14446E01 | 39 | 88 | TCACAAGCTCCCATCGCATCATAGGAATTGGTACGCAGTCGATGAGTCCTGAGTAAGCGTTACGGTTGTTCCTTGTTGCATCTCCTTT |
| 212 | 02R140 | 14446E01 | 39 | 86 | TCACAAGCTCCCATCGCATCATAGGAATTGGTACGCAGTCGATGAGTCCTGAGTAAGCTACGGTTGTTCCTTGTTGCATCTCCTTG |
| 213 | 02R141 | 14446E10 | 40 | 84 | AACTCTCAATTTTTCAACCTTCTCTAGGAATTGGTACGCAGTCGATGAGTCCTGAGTAAGGTATCACTGGCTGGAACTTCTCCC |
| 214 | 02R142 | 14446E10 | 40 | 82 | AACTCTCAATTTTTCAACCTTCTCTAGGAATTGGTACGCAGTCGATGAGTCCTGAGTAAGATCACTGGCTGGAACTTCTCCG |

Example 16

Design of the PCR Amplification Primers

The sequence of one of the primers used for PCR amplification was complementary to the PCR primer binding regions incorporated in the ligation probes described in Example 15. The sequence of the second PCR primer matched the PCR primer binding region of the probe. Usually the forward primer is labelled. The concentration of the oligonucleotides was adjusted to 50 ng/μl. The sequence of the primers in 5'-3' orientation are depicted in Table 11.

TABLE 11

PCR amplification primers

| SEQ ID # | Primer nr | 5'-3' | |
|---|---|---|---|
| 215 | MseI + 0: 93E40 | GATGAGTCCTGAGTAA* | M00k |
| 216 | EcoRI + 0 93L01 | GACTGCGTACCAATTC* | E00k |
| 217 | EcoRI + 1 93L02 | GACTGCGTACCAATTCA | E01K NED |
| 218 | EcoRI + 1 93L04 | GACTGCGTACCAATTCG | E03K 5' + T Joe |
| 219 | EcoRI + 1 93L05 | GACTGCGTACCAATTCT | E04K FAM |

*Multiple labels possible

Example 17

Ligation and Amplification 9 samples (samples 1-9) of homozygous tomato lines (Example 14) were subjected to a multiplex oligonucleotide ligation reaction using a mixture of 20 padlock probes (set 4). Conditions used were 1× Taq DNA ligase buffer (NEB), 0.2 U/μl Taq DNA ligase, and 0.05 fmol/μl of each probe in a volume of 10 μl. Ligation was performed in a thermocycler (Perkin Elmer) with the following cycling conditions: 2 minutes at 94° C.+10*(15 seconds at 94° C.+60 minutes at 60° C.)+4° C. continuously. Following ligation, the 10 μl ligation product was diluted with 30 μl 1× Taq DNA ligase buffer. The 40 μl of each reaction was used to perform 4 amplification reactions using 4 different labelled E00k primers each combined with M00k. The E00k primer labelled with ET-ROX and JOE were designed with an extra 1 bp in comparison with E00k labelled with FAM and NED length, to prevent possible crosstalk between fluorescent labels when analysing these products on the MegaBACE. Conditions used were 30 ng labelled E00k primer and 30 ng M00k primer, 1× Accuprime buffer I, 0.4 ul Accuprime polymerase nitrogen) on 10 μl diluted ligation product in a 20 μl PCR reaction. PCR was performed in a thermocycler with the following cycling conditions: 2 minutes at 94° C.+35*(15 seconds at 94° C.+30 seconds at 56° C.+60 seconds at 68° C.)+4° C. continuously. PCR product was purified using Sephadex 50 and diluted 80 times with MQ. Diluted PCR product was analysed on the MegaBACE. The different fluorescent-labelled products were run separately and in different combinations (2, 3 and 4 fluorescent dyes). The results are presented in FIG. 16.

Example 18

Figure 17:
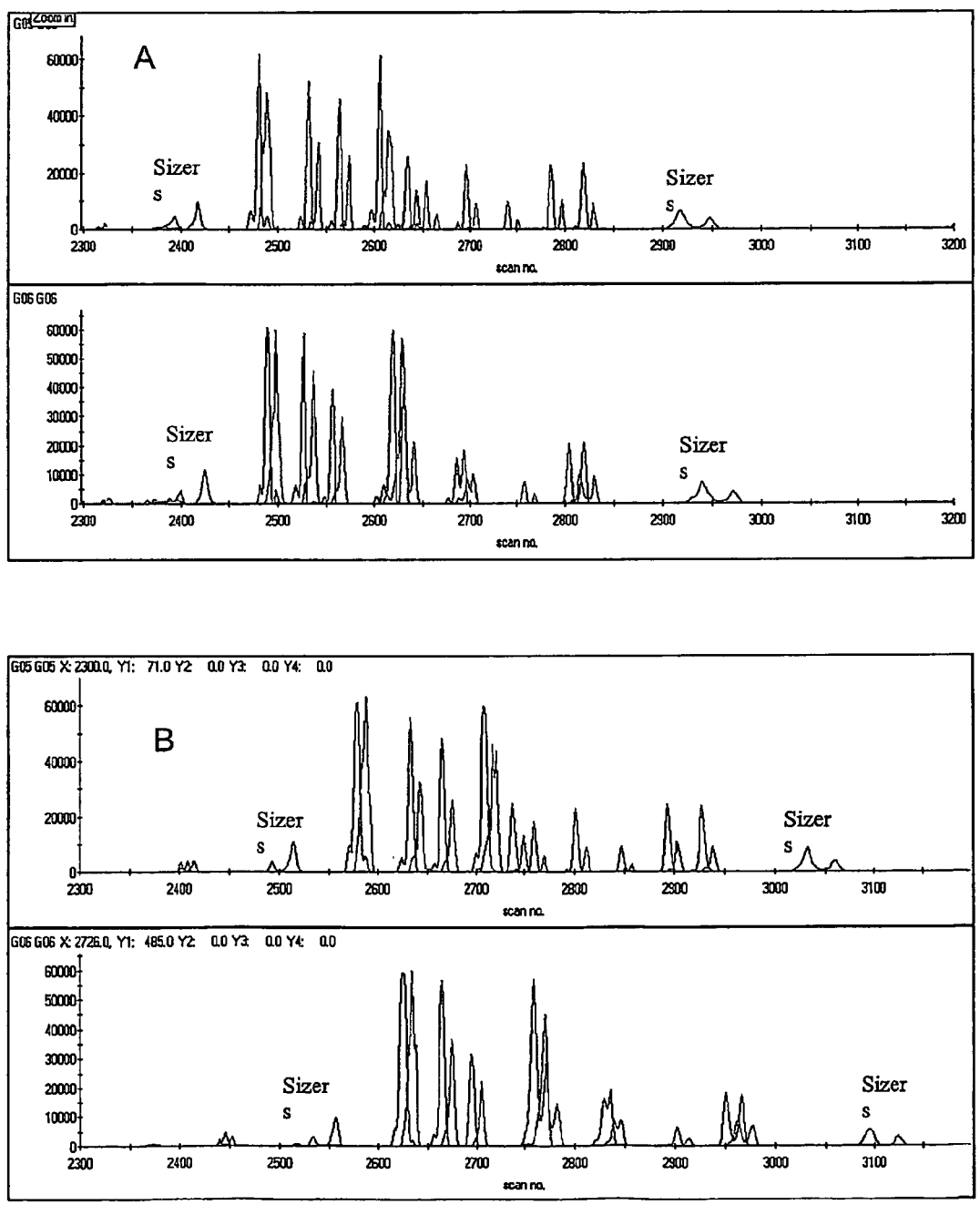

Use of Length/Dye Combinations and the Principle of Repeated Injection in Combination with Reuse of the LPA Matrix The amplification products of set 4 were analysed using consecutive runs without replacement of the LPA matrix between runs. Samples of the amplification products were injected after a run period of 40 minutes without changing the matrix. Results are presented in FIG. 17. Consecutive runs can be performed without changing the matrix and without significant loss of data quality.

Example 19

Selective Amplification of a Multiplex Ligation Sample

This experiment demonstrates the possibility of a higher multiplex of oligonucleotide ligation, in combination with the selective amplification of a subset of the formed ligation products using (AFLP) amplification primers with selective nucleotides.

Using the 4 designed probe sets, primers are based on set 1, 2, 4 and 5 but with additional selective nucleotides located immediately 3' of the primer binding sites in the probes.

Each set was ligated separately, and in combination with other sets, up to a multiplex of 40 based on the 4 sets together. AFLP+1/+1 amplifications using different labelled E00k primers were performed using the scheme depicted below.

| Ligation set | Amplification | | | |
|---|---|---|---|---|
| | Label | Primers | Selective bases | Set |
| 1 | NED | E01k/M01k | +A/+A | 1 |
| 2 | JOE | E03k/M04k | +G/+T | 2 |
| 5 | FAM | E04k/M03k | +T/+G | 5 |
| 1 + 4 | NED | E01k/M01k | +A/+A | 1 |
| 2 + 4 | JOE | E03k/M04k | +G/+T | 2 |
| 4 + 5 | FAM | E04k/M03k | +T/+G | 5 |

-continued

| Ligation set | Amplification | | | |
|---|---|---|---|---|
| | Label | Primers | Selective bases | Set |
| 1 + 2 + 4 + 5 | JOE | E03k/M04k | +G/+T | 2 |
| 1 + 2 + 4 + 5 | NED | E01k/M01k | +A/+A | 1 |
| 1 + 2 + 4 + 5 | FAM | E04k/M03k | +T/+G | 5 |

Figure 18:
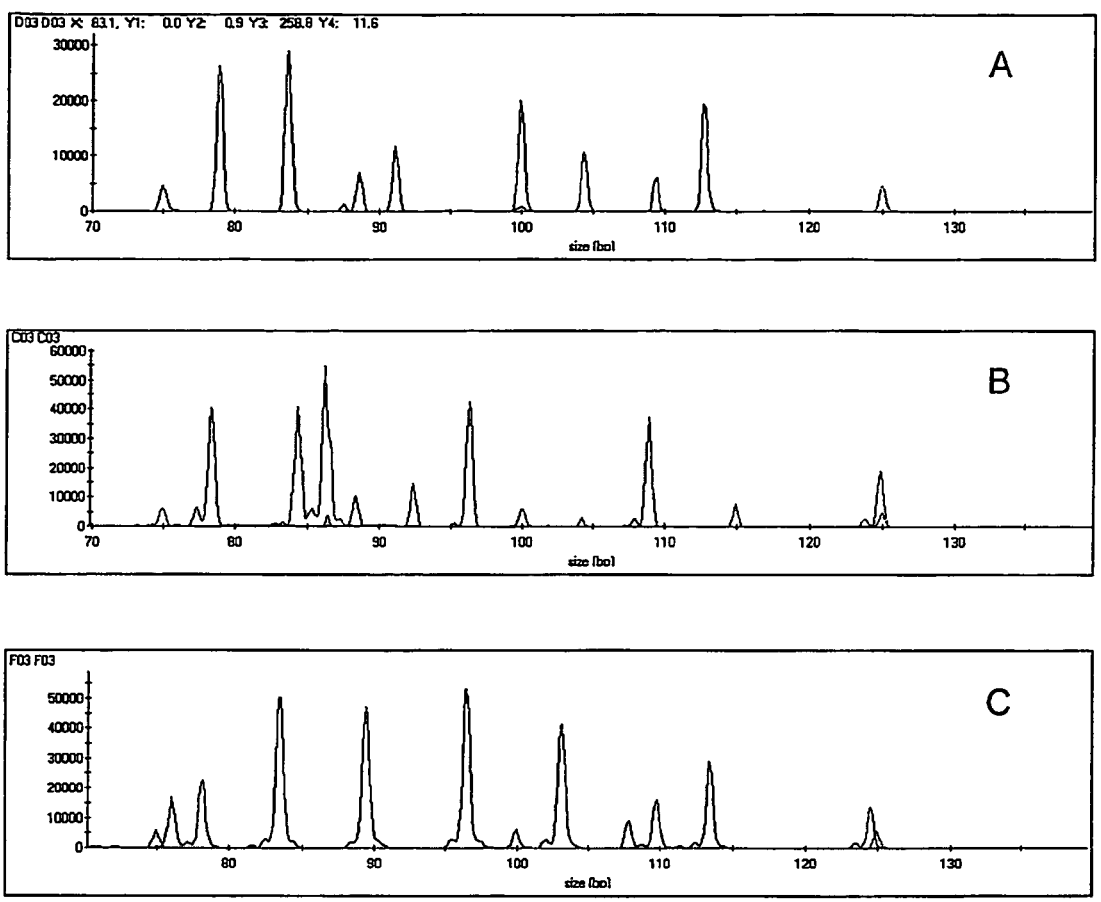

Conditions used were 1× Taq DNA ligase buffer (NEB), 0.2 U/μl Taq DNA ligase, and 0.05 fmol/μl of each probe in a volume of 10 μl. Ligation was performed in a thermocycler (Perkin Elmer) with the following cycling conditions: 2 minutes at 94° C.+10*(15 seconds at 94° C.; 60 minutes at 60° C.)+4° C. continuously. Following ligation, the 10 μl ligation product was diluted with 30 μl 1×Taq DNA ligase buffer. Conditions used were 30 ng labelled E00k primer and 30 ng M00k primer, 1× Accuprime buffer (Invitrogen) I, 0.4 ul Accuprime polymerase (Invitrogen) on 10 μl diluted ligation product in a 20 μl PCR reaction. PCR was performed in a thermocycler with the following cycling conditions: 2 minutes at 94° C.+35*(15 seconds at 94° C.+30 seconds at 56° C.+6 minutes at 68° C.)+4° C. continuously. PCR product was purified using Sephadex 50 and diluted 80 times with MQ. Diluted PCR product was analysed on the Megabace. The different fluorescent-labelled products were run in separate capillaries. The results are presented in FIG. 18.

Buffer Compositions:

1×Taq DNA ligase buffer
20 mM Tris-HCl
25 mM potassium acetate
10 mM Magnesium acetate
10 mM DTT
1 mM NAD
0.1% Triton X-100
(pH 7.6@ 25° C.)

1×AccuPrime Taq DNA polymerase buffer
20 mM Tris-HCl (pH8.4)
50 mM KCl
1.5 mM MgCl$_2$
0.2 mM dGTP, dATP, dTTP and dCTP
thermostable AccuPrime™ protein
10% glycerol

---

SEQUENCE LISTING

<160> NUMBER OF SEQ ID NOS: 219

<210> SEQ ID NO 1
<211> LENGTH: 48
<212> TYPE: DNA
<213> ORGANISM: Artificial Sequence
<220> FEATURE:
<223> OTHER INFORMATION: Oligonucleotide

<400> SEQUENCE: 1
cgccagggtt ttcccagtca cgacttcagg actagtctat accttgag        48

<210> SEQ ID NO 2
<211> LENGTH: 51
<212> TYPE: DNA
<213> ORGANISM: Artificial Sequence

```
<220> FEATURE:
<223> OTHER INFORMATION: Oligonucleotide

<400> SEQUENCE: 2
cgccagggtt ttcccagtca cgacgacttc aggactagtc tataccttga a        51

<210> SEQ ID NO 3
<211> LENGTH: 49
<212> TYPE: DNA
<213> ORGANISM: Artificial Sequence
<220> FEATURE:
<223> OTHER INFORMATION: Oligonucleotide

<400> SEQUENCE: 3
ctatgtgaac caaattaaag tttactcctg tgtgaaattg ttatccgct            49

<210> SEQ ID NO 4
<211> LENGTH: 49
<212> TYPE: DNA
<213> ORGANISM: Artificial Sequence
<220> FEATURE:
<223> OTHER INFORMATION: Oligonucleotide

<400> SEQUENCE: 4
cgccagggtt ttcccagtca cgacctgctc tttcctcgct agcttcaga            49

<210> SEQ ID NO 5
<211> LENGTH: 51
<212> TYPE: DNA
<213> ORGANISM: Artificial Sequence
<220> FEATURE:
<223> OTHER INFORMATION: Oligonucleotide

<400> SEQUENCE: 5
cgccagggtt ttcccagtca cgacgactgc tctttcctcg ctagcttcag c        51

<210> SEQ ID NO 6
<211> LENGTH: 53
<212> TYPE: DNA
<213> ORGANISM: Artificial Sequence
<220> FEATURE:
<223> OTHER INFORMATION: Oligonucleotide

<400> SEQUENCE: 6 agat tcggac cttctctcat aatccgactt cctgtgtgaa attgttatcc gct      53

<210> SEQ ID NO 7
<211> LENGTH: 49
<212> TYPE: DNA
<213> ORGANISM: Artificial Sequence
<220> FEATURE:
<223> OTHER INFORMATION: Oligonucleotide

<400> SEQUENCE: 7
cgccagggtt ttcccagtca cgacgaagag gagagtggct acgaactct            49

<210> SEQ ID NO 8
<211> LENGTH: 51
<212> TYPE: DNA
<213> ORGANISM: Artificial Sequence
<220> FEATURE:
<223> OTHER INFORMATION: Oligonucleotide

<400> SEQUENCE: 8
cgccagggtt ttcccagtca cgacgagaag aggagagtgg ctacgaactc g        51
```

<210> SEQ ID NO 9
<211> LENGTH: 57
<212> TYPE: DNA
<213> ORGANISM: Artificial Sequence
<220> FEATURE:
<223> OTHER INFORMATION: Oligonucleotide

<400> SEQUENCE: 9
gcgataactg ctctgtagaa agacccgatt agctcctgtg tgaaattgtt atccgct        57

<210> SEQ ID NO 10
<211> LENGTH: 49
<212> TYPE: DNA
<213> ORGANISM: Artificial Sequence
<220> FEATURE:
<223> OTHER INFORMATION: Oligonucleotide

<400> SEQUENCE: 10
cgccagggtt ttcccagtca cgacaatcgg cctaagcaag cttgttttc                49

<210> SEQ ID NO 11
<211> LENGTH: 51
<212> TYPE: DNA
<213> ORGANISM: Artificial Sequence
<220> FEATURE:
<223> OTHER INFORMATION: Oligonucleotide

<400> SEQUENCE: 11
cgccagggtt ttcccagtca cgacgaaatc ggcctaagca agcttgtttt g              51

<210> SEQ ID NO 12
<211> LENGTH: 61
<212> TYPE: DNA
<213> ORGANISM: Artificial Sequence
<220> FEATURE:
<223> OTHER INFORMATION: Oligonucleotide

<400> SEQUENCE: 12
tgctattgat atctctgtgc aactcatcgg atcagcttcc tgtgtgaaat tgttatccgc    60
t                                                                    61

<210> SEQ ID NO 13
<211> LENGTH: 49
<212> TYPE: DNA
<213> ORGANISM: Artificial Sequence
<220> FEATURE:
<223> OTHER INFORMATION: Oligonucleotide

<400> SEQUENCE: 13
cgccagggtt ttcccagtca cgacgatcgg aaagatatcg gagctcctt                49

<210> SEQ ID NO 14
<211> LENGTH: 51
<212> TYPE: DNA
<213> ORGANISM: Artificial Sequence
<220> FEATURE:
<223> OTHER INFORMATION: Oligonucleotide

<400> SEQUENCE: 14
cgccagggtt ttcccagtca cgacgagatc ggaaagatat cggagctcct c              51

<210> SEQ ID NO 15
<211> LENGTH: 65
<212> TYPE: DNA
<213> ORGANISM: Artificial Sequence

```
<220> FEATURE:
<223> OTHER INFORMATION: Oligonucleotide

<400> SEQUENCE: 15
gtcggtgtca accgatccac ggcgcatgct agcacgtact gtcctgtgtg aaattgttat    60
ccgct                                                               65

<210> SEQ ID NO 16
<211> LENGTH: 49
<212> TYPE: DNA
<213> ORGANISM: Artificial Sequence
<220> FEATURE:
<223> OTHER INFORMATION: Oligonucleotide

<400> SEQUENCE: 16
cgccagggtt ttcccagtca cgacgaactg gcatcaatca ggcctccaa               49

<210> SEQ ID NO 17
<211> LENGTH: 51
<212> TYPE: DNA
<213> ORGANISM: Artificial Sequence
<220> FEATURE:
<223> OTHER INFORMATION: Oligonucleotide

<400> SEQUENCE: 17
cgccagggtt ttcccagtca cgacgagaac tggcatcaat caggcctcca t            51

<210> SEQ ID NO 18
<211> LENGTH: 69
<212> TYPE: DNA
<213> ORGANISM: Artificial Sequence
<220> FEATURE:
<223> OTHER INFORMATION: Oligonucleotide

<400> SEQUENCE: 18
ccttaatgca agggcttatt acgtcgtacc agtcatggat ccgattcctg tgtgaaattg    60
ttatccgct                                                           69

<210> SEQ ID NO 19
<211> LENGTH: 49
<212> TYPE: DNA
<213> ORGANISM: Artificial Sequence
<220> FEATURE:
<223> OTHER INFORMATION: Oligonucleotide

<400> SEQUENCE: 19
cgccagggtt ttcccagtca cgacggactc caaggtattg ttaggcgcc               49

<210> SEQ ID NO 20
<211> LENGTH: 51
<212> TYPE: DNA
<213> ORGANISM: Artificial Sequence
<220> FEATURE:
<223> OTHER INFORMATION: Oligonucleotide

<400> SEQUENCE: 20
cgccagggtt ttcccagtca cgacgaggac tccaaggtat tgttaggcgc a            51

<210> SEQ ID NO 21
<211> LENGTH: 73
<212> TYPE: DNA
<213> ORGANISM: Artificial Sequence
<220> FEATURE:
<223> OTHER INFORMATION: Oligonucleotide
```

```
<400> SEQUENCE: 21
aaccaccaag atcagtctca tcttcgatca tcgactggta ctacggactt cctgtgtgaa        60
attgttatcc gct                                                          73

<210> SEQ ID NO 22
<211> LENGTH: 49
<212> TYPE: DNA
<213> ORGANISM: Artificial Sequence
<220> FEATURE:
<223> OTHER INFORMATION: Oligonucleotide

<400> SEQUENCE: 22
cgccagggtt ttcccagtca cgaccatctc ttgcgccttc tcagtgttg                    49

<210> SEQ ID NO 23
<211> LENGTH: 51
<212> TYPE: DNA
<213> ORGANISM: Artificial Sequence
<220> FEATURE:
<223> OTHER INFORMATION: Oligonucleotide

<400> SEQUENCE: 23
cgccagggtt ttcccagtca cgacgacatc tcttgcgcct tctcagtgtt a                 51

<210> SEQ ID NO 24
<211> LENGTH: 77
<212> TYPE: DNA
<213> ORGANISM: Artificial Sequence
<220> FEATURE:
<223> OTHER INFORMATION: Oligonucleotide

<400> SEQUENCE: 24
tgacgtccgt cgaagaatag gtaacgtacg catgctaacg ttacggacta tcgtcctgtg        60
tgaaattgtt atccgct                                                      77

<210> SEQ ID NO 25
<211> LENGTH: 49
<212> TYPE: DNA
<213> ORGANISM: Artificial Sequence
<220> FEATURE:
<223> OTHER INFORMATION: Oligonucleotide

<400> SEQUENCE: 25
cgccagggtt ttcccagtca cgacagtttc aaaacccatg acgcttcta                    49

<210> SEQ ID NO 26
<211> LENGTH: 51
<212> TYPE: DNA
<213> ORGANISM: Artificial Sequence
<220> FEATURE:
<223> OTHER INFORMATION: Oligonucleotide

<400> SEQUENCE: 26
cgccagggtt ttcccagtca cgacgaagtt tcaaaaccca tgacgcttct t                 51

<210> SEQ ID NO 27
<211> LENGTH: 81
<212> TYPE: DNA
<213> ORGANISM: Artificial Sequence
<220> FEATURE:
<223> OTHER INFORMATION: Oligonucleotide

<400> SEQUENCE: 27
gtgatagctg aaaagaccca ttctccgtag catcgatatc ggtcaactgg atcagcttcc        60
```
tgtgtgaaat tgttatccgc t                                        81

<210> SEQ ID NO 28
<211> LENGTH: 49
<212> TYPE: DNA
<213> ORGANISM: Artificial Sequence
<220> FEATURE:
<223> OTHER INFORMATION: Oligonucleotide

<400> SEQUENCE: 28
cgccagggtt ttcccagtca cgacatactc caattgctca ggcacagtt          49

<210> SEQ ID NO 29
<211> LENGTH: 51
<212> TYPE: DNA
<213> ORGANISM: Artificial Sequence
<220> FEATURE:
<223> OTHER INFORMATION: Oligonucleotide

<400> SEQUENCE: 29
cgccagggtt ttcccagtca cgacgaatac tccaattgct caggcacagt c       51

<210> SEQ ID NO 30
<211> LENGTH: 85
<212> TYPE: DNA
<213> ORGANISM: Artificial Sequence
<220> FEATURE:
<223> OTHER INFORMATION: Oligonucleotide

<400> SEQUENCE: 30
ctccttgtcc cacgaagata gttccgtacc atgtcgacgt agatccgtat agcactgagt    60
ctcctgtgtg aaattgttat ccgct                                    85

<210> SEQ ID NO 31
<211> LENGTH: 49
<212> TYPE: DNA
<213> ORGANISM: Artificial Sequence
<220> FEATURE:
<223> OTHER INFORMATION: Oligonucleotide

<400> SEQUENCE: 31
cgccagggtt ttcccagtca cgacgtagag gctctaaaca gctgcttcc          49

<210> SEQ ID NO 32
<211> LENGTH: 51
<212> TYPE: DNA
<213> ORGANISM: Artificial Sequence
<220> FEATURE:
<223> OTHER INFORMATION: Oligonucleotide

<400> SEQUENCE: 32
cgccagggtt ttcccagtca cgacgagtag aggctctaaa cagctgcttc g       51

<210> SEQ ID NO 33
<211> LENGTH: 49
<212> TYPE: DNA
<213> ORGANISM: Artificial Sequence
<220> FEATURE:
<223> OTHER INFORMATION: Oligonucleotide

<400> SEQUENCE: 33
cttgtttatg ctaagggccg gctcctcctg tgtgaaattg ttatccgct          49

<210> SEQ ID NO 34

<210> SEQ ID NO 34
<211> LENGTH: 49
<212> TYPE: DNA
<213> ORGANISM: Artificial Sequence
<220> FEATURE:
<223> OTHER INFORMATION: Oligonucleotide

<400> SEQUENCE: 34
cgccagggtt ttcccagtca cgactaagtc agctcctaag cttccatcg          49

<210> SEQ ID NO 35
<211> LENGTH: 51
<212> TYPE: DNA
<213> ORGANISM: Artificial Sequence
<220> FEATURE:
<223> OTHER INFORMATION: Oligonucleotide

<400> SEQUENCE: 35
cgccagggtt ttcccagtca cgacgataag tcagctccta agcttccatc t        51

<210> SEQ ID NO 36
<211> LENGTH: 53
<212> TYPE: DNA
<213> ORGANISM: Artificial Sequence
<220> FEATURE:
<223> OTHER INFORMATION: Oligonucleotide

<400> SEQUENCE: 36
aagccacttc ctcctgctca agcgcgactt cctgtgtgaa attgttatcc gct      53

<210> SEQ ID NO 37
<211> LENGTH: 24
<212> TYPE: DNA
<213> ORGANISM: Artificial Sequence
<220> FEATURE:
<223> OTHER INFORMATION: M13 forward primer

<400> SEQUENCE: 37
cgccagggtt ttcccagtca cgac                                     24

<210> SEQ ID NO 38
<211> LENGTH: 24
<212> TYPE: DNA
<213> ORGANISM: Artificial Sequence
<220> FEATURE:
<223> OTHER INFORMATION: M13 reverse primer

<400> SEQUENCE: 38
agcggataac aatttcacac agga                                     24

<210> SEQ ID NO 39
<211> LENGTH: 4
<212> TYPE: DNA
<213> ORGANISM: Artificial Sequence
<220> FEATURE:
<223> OTHER INFORMATION: Oligonucleotide sizer

<400> SEQUENCE: 39 tgca                                                            4

<210> SEQ ID NO 40
<211> LENGTH: 8
<212> TYPE: DNA
<213> ORGANISM: Artificial Sequence
<220> FEATURE:
<223> OTHER INFORMATION: Oligonucleotide sizer

<400> SEQUENCE: 40 acgttacg                                                               8

<210> SEQ ID NO 41
<211> LENGTH: 12
<212> TYPE: DNA
<213> ORGANISM: Artificial Sequence
<220> FEATURE:
<223> OTHER INFORMATION: Oligonucleotide sizer

<400> SEQUENCE: 41
tagcgtcagc at                                                          12

<210> SEQ ID NO 42
<211> LENGTH: 16
<212> TYPE: DNA
<213> ORGANISM: Artificial Sequence
<220> FEATURE:
<223> OTHER INFORMATION: Oligonucleotide

<400> SEQUENCE: 42
catggcatac gttacg                                                      16

<210> SEQ ID NO 43
<211> LENGTH: 20
<212> TYPE: DNA
<213> ORGANISM: Artificial Sequence
<220> FEATURE:
<223> OTHER INFORMATION: Oligonucleotide

<400> SEQUENCE: 43
gatcgctaac gttacggcat                                                  20

<210> SEQ ID NO 44
<211> LENGTH: 24
<212> TYPE: DNA
<213> ORGANISM: Artificial Sequence
<220> FEATURE:
<223> OTHER INFORMATION: Oligonucleotide

<400> SEQUENCE: 44
tcgagatcac gtcatgctga gcat                                             24

<210> SEQ ID NO 45
<211> LENGTH: 28
<212> TYPE: DNA
<213> ORGANISM: Artificial Sequence
<220> FEATURE:
<223> OTHER INFORMATION: Oligonucleotide

<400> SEQUENCE: 45
cagttcaggc attcgactag cgtatacg                                         28

<210> SEQ ID NO 46
<211> LENGTH: 32
<212> TYPE: DNA
<213> ORGANISM: Artificial Sequence
<220> FEATURE:
<223> OTHER INFORMATION: Oligonucleotide

<400> SEQUENCE: 46
gtcaatcgga ctctgagact catgcgatga ct                                    32

<210> SEQ ID NO 47
<211> LENGTH: 36
<212> TYPE: DNA

```
<213> ORGANISM: Artificial Sequence
<220> FEATURE:
<223> OTHER INFORMATION: Oligonucleotide

<400> SEQUENCE: 47
gatccgatcg atatcgacgt agctgcatcg taatcg                              36

<210> SEQ ID NO 48
<211> LENGTH: 4
<212> TYPE: DNA
<213> ORGANISM: Artificial Sequence
<220> FEATURE:
<223> OTHER INFORMATION: Oligonucleotide

<400> SEQUENCE: 48 actg                                                                  4

<210> SEQ ID NO 49
<211> LENGTH: 8
<212> TYPE: DNA
<213> ORGANISM: Artificial Sequence
<220> FEATURE:
<223> OTHER INFORMATION: Oligonucleotide

<400> SEQUENCE: 49 gcatcagt                                                              8

<210> SEQ ID NO 50
<211> LENGTH: 12
<212> TYPE: DNA
<213> ORGANISM: Artificial Sequence
<220> FEATURE:
<223> OTHER INFORMATION: Oligonucleotide

<400> SEQUENCE: 50
atcggcatta cg                                                        12

<210> SEQ ID NO 51
<211> LENGTH: 16
<212> TYPE: DNA
<213> ORGANISM: Artificial Sequence
<220> FEATURE:
<223> OTHER INFORMATION: Oligonucleotide

<400> SEQUENCE: 51
tacggcatag tcacgt                                                    16

<210> SEQ ID NO 52
<211> LENGTH: 20
<212> TYPE: DNA
<213> ORGANISM: Artificial Sequence
<220> FEATURE:
<223> OTHER INFORMATION: Oligonucleotide

<400> SEQUENCE: 52
gatcgctaac gttacggcat                                                20

<210> SEQ ID NO 53
<211> LENGTH: 24
<212> TYPE: DNA
<213> ORGANISM: Artificial Sequence
<220> FEATURE:
<223> OTHER INFORMATION: Oligonucleotide

<400> SEQUENCE: 53
ctagatgctc aggctatcga catg                                           24
```

```
<210> SEQ ID NO 54
<211> LENGTH: 28
<212> TYPE: DNA
<213> ORGANISM: Artificial Sequence
<220> FEATURE:
<223> OTHER INFORMATION: Oligonucleotide

<400> SEQUENCE: 54
gtaccgatac gttagcgact tagccgta                                          28

<210> SEQ ID NO 55
<211> LENGTH: 32
<212> TYPE: DNA
<213> ORGANISM: Artificial Sequence
<220> FEATURE:
<223> OTHER INFORMATION: Oligonucleotide

<400> SEQUENCE: 55
cgtaatcgga tccgtaacgt gcatatgcca gt                                     32

<210> SEQ ID NO 56
<211> LENGTH: 36
<212> TYPE: DNA
<213> ORGANISM: Artificial Sequence
<220> FEATURE:
<223> OTHER INFORMATION: Oligonucleotide

<400> SEQUENCE: 56
gacttcgaga tctgcaacgt acgtcgtaag ctgcta                                 36

<210> SEQ ID NO 57
<211> LENGTH: 5
<212> TYPE: DNA
<213> ORGANISM: Artificial Sequence
<220> FEATURE:
<223> OTHER INFORMATION: Oligonucleotide

<400> SEQUENCE: 57 cgact                                                                    5

<210> SEQ ID NO 58
<211> LENGTH: 9
<212> TYPE: DNA
<213> ORGANISM: Artificial Sequence
<220> FEATURE:
<223> OTHER INFORMATION: Oligonucleotide

<400> SEQUENCE: 58 ccgattagc                                                                9

<210> SEQ ID NO 59
<211> LENGTH: 13
<212> TYPE: DNA
<213> ORGANISM: Artificial Sequence
<220> FEATURE:
<223> OTHER INFORMATION: Oligonucleotide

<400> SEQUENCE: 59
catcggatca gct                                                          13

<210> SEQ ID NO 60
<211> LENGTH: 17
<212> TYPE: DNA
<213> ORGANISM: Artificial Sequence
<220> FEATURE:
```

```
<223> OTHER INFORMATION: Oligonucleotide

<400> SEQUENCE: 60
catgctagca cgtactg                                                    17

<210> SEQ ID NO 61
<211> LENGTH: 21
<212> TYPE: DNA
<213> ORGANISM: Artificial Sequence
<220> FEATURE:
<223> OTHER INFORMATION: Oligonucleotide

<400> SEQUENCE: 61
cgtaccagtc atggatccga t                                               21

<210> SEQ ID NO 62
<211> LENGTH: 25
<212> TYPE: DNA
<213> ORGANISM: Artificial Sequence
<220> FEATURE:
<223> OTHER INFORMATION: Oligonucleotide

<400> SEQUENCE: 62
cgatcatcga ctggtactac ggact                                           25

<210> SEQ ID NO 63
<211> LENGTH: 29
<212> TYPE: DNA
<213> ORGANISM: Artificial Sequence
<220> FEATURE:
<223> OTHER INFORMATION: Oligonucleotide

<400> SEQUENCE: 63
cgtacgcatg ctaacgttac ggactatcg                                       29

<210> SEQ ID NO 64
<211> LENGTH: 33
<212> TYPE: DNA
<213> ORGANISM: Artificial Sequence
<220> FEATURE:
<223> OTHER INFORMATION: Oligonucleotide

<400> SEQUENCE: 64
ccgtagcatc gatatcggtc aactggatca gct                                  33

<210> SEQ ID NO 65
<211> LENGTH: 37
<212> TYPE: DNA
<213> ORGANISM: Artificial Sequence
<220> FEATURE:
<223> OTHER INFORMATION: Oligonucleotide

<400> SEQUENCE: 65
cgtaccatgt cgacgtagat ccgtatagca ctgagtc                              37

<210> SEQ ID NO 66
<211> LENGTH: 5
<212> TYPE: DNA
<213> ORGANISM: Artificial Sequence
<220> FEATURE:
<223> OTHER INFORMATION: Oligonucleotide

<400> SEQUENCE: 66 cgtac                                                                  5
```

```
<210> SEQ ID NO 67
<211> LENGTH: 9
<212> TYPE: DNA
<213> ORGANISM: Artificial Sequence
<220> FEATURE:
<223> OTHER INFORMATION: Oligonucleotide

<400> SEQUENCE: 67 cgcattcga                                                                   9

<210> SEQ ID NO 68
<211> LENGTH: 13
<212> TYPE: DNA
<213> ORGANISM: Artificial Sequence
<220> FEATURE:
<223> OTHER INFORMATION: Oligonucleotide

<400> SEQUENCE: 68
catcggcatg act                                                             13

<210> SEQ ID NO 69
<211> LENGTH: 17
<212> TYPE: DNA
<213> ORGANISM: Artificial Sequence
<220> FEATURE:
<223> OTHER INFORMATION: Oligonucleotide

<400> SEQUENCE: 69
cgtcaatgca cgttacg                                                         17

<210> SEQ ID NO 70
<211> LENGTH: 21
<212> TYPE: DNA
<213> ORGANISM: Artificial Sequence
<220> FEATURE:
<223> OTHER INFORMATION: Oligonucleotide

<400> SEQUENCE: 70
cgcatcgata gctctgaacg t                                                    21

<210> SEQ ID NO 71
<211> LENGTH: 25
<212> TYPE: DNA
<213> ORGANISM: Artificial Sequence
<220> FEATURE:
<223> OTHER INFORMATION: Oligonucleotide

<400> SEQUENCE: 71
cgcatatcgg atcgatcgca tacgt                                                25

<210> SEQ ID NO 72
<211> LENGTH: 29
<212> TYPE: DNA
<213> ORGANISM: Artificial Sequence
<220> FEATURE:
<223> OTHER INFORMATION: Oligonucleotide

<400> SEQUENCE: 72
catcggatcc atgcgtagca tatcgacgt                                            29

<210> SEQ ID NO 73
<211> LENGTH: 33
<212> TYPE: DNA
<213> ORGANISM: Artificial Sequence
<220> FEATURE:
<223> OTHER INFORMATION: Oligonucleotide
```

<400> SEQUENCE: 73
ctgcaagtcc gattacgatc gacgtgctat gca          33

<210> SEQ ID NO 74
<211> LENGTH: 37
<212> TYPE: DNA
<213> ORGANISM: Artificial Sequence
<220> FEATURE:
<223> OTHER INFORMATION: Oligonucleotide

<400> SEQUENCE: 74
cagctcagta tcgagtcgac tacgttgcat acggatc      37

<210> SEQ ID NO 75
<211> LENGTH: 669
<212> TYPE: DNA
<213> ORGANISM: Lycopersicon esculentum

<400> SEQUENCE: 75
cckcggagaa wtgaagaagt atgctgtgtc atccggtgtt ggctcacact caggtactgt    60
tagacccatc tcatgcttaa caatkkgatt ctttgagcgt tacctaktga actagtatat   120
tttkggtgtg ctcacttact gcctcaagtt atgtgatggt ttctaattkt gactttaatt   180
ataaatcatg cacatcttat ataaatcaga tttccaaagc tgctgtatat tggttcagta   240
gataatatgg ttttatctct taactggtta tatctgcagt catttttggg ttatacctct   300
ttcatagtcc tgattaaagg attttgagtt attttcaatg tctctttgta aacaaagatt   360
atactagaat caatctaatg ttttctttcc tttaaataaa ttacagataa ggaagatgaa   420
gggtttgaaa cagaagaaag cccatttgat ggagatccag gttaatggag gatcaattgc   480
tcagaaggtt gacttcgcat atggtttctt tgagaagcag gttccagttg atgctgtttt   540
ccagaaggat gagatgattg acatcattgg tgtcaccaag ggtaagggtt atgaaggtgt   600
ygtaactcgt tggggtgtga cacgtcttct cgcaaaaccc acggggtcta cgtaaggtgc   660
tgttggggc                                                           669

<210> SEQ ID NO 76
<211> LENGTH: 556
<212> TYPE: DNA
<213> ORGANISM: Lycopersicon esculentum

<400> SEQUENCE: 76
gcytggggac tagttctttt cagaatcata tcatctgtag agaaatcagc tgctttcctg    60
aatgttcctc gtccgaaatc taggttgtaa gagtctgtaa gaccttccac cagatcaaaa   120
tcaggtttcc atcctagctc agcctttgac ttctcgatgg atgtaaagaa atgctgtaga   180
aattcgatgt taaaccaac gagaagacat agatagacta gtgttggaca agaatccgat    240
attaaacaga caagctaaca acttcaacag aggaaataaa ccatatttct tgtagtattt   300
cgtttggact acgattgatt gtacaaaaat gtgtgttaat tttagtgagc atactgatgt   360
gtgttttagg aagggactag gataagaggc ggtgaacatg ttgtgaatct tcactgatga   420
ttcatttagt ttgatcatat catttgattc tttgataaag aatgtctcga atttcaatat   480
gaatggtaaa caactgaaat caacacacta atatttacct ggtcacggaa tgggaatgct   540
ttcttcttgc caaaat                                                   556

<210> SEQ ID NO 77
<211> LENGTH: 727

```
<212> TYPE: DNA
<213> ORGANISM: Lycopersicon esculentum
<220> FEATURE:
<221> NAME/KEY: misc_feature
<222> LOCATION: (1)..(727)
<223> OTHER INFORMATION: Oligonucleotide
<220> FEATURE:
<223> OTHER INFORMATION:
<220> FEATURE:
<221> NAME/KEY: misc_feature
<222> LOCATION: (1)..(727)
<223> OTHER INFORMATION: Oligonucleotide
<223> OTHER INFORMATION: W=A or T; M=A or C; R=A or G; Y=C or T;
      K=G or T; S=G or C; H=A, C or T; B=C, G or T; V=A, C or G; D=A,
      G or T; N=A, C, G or T

<400> SEQUENCE: 77
agnahkyycv aggctcacda scaggttgga aaaatcattt tgatacaraa rttgcatttt         60
ctggttattc aggtgatttc ccttctatat gtcaaactta ttgaaacgag tcttctgaaa        120
aataaatgga aagttatatg gaaaaasatt tccaggatat tgcttagttt ctcataagta        180
taaagcttta tatgtgaacc aattcaacag gtacatatat cagaggcccg ggtttctgct        240
gctttagata gctagctta catggaagaa ttggttaacg ataggcttct gcaagagaga         300
agcacagtag aatcagaatg cacgtcttcc tctgcaagca cgtcaacagg attattagac        360
actccaaaaa gcaagcaacc acgaagaacg ctgaatgtct caggtcctgt ccaagattac        420
agttcccgtt tgaagaactt ttggtaccct gttgcattct ccgcagatct taagaatgac        480
accatggtga gtcaattatc stcatatctg ccagtctctt taacctaaaa gaaagaaaac        540
atttgatcta aaacacagaa aaccatgtag atgcaaaatt atgatgccaa acaaattaa         600 caagctatat gatctacgct cctactttat ggtcttccat gtatattctt kgggatcttc        660
taattgatga ctgttaactg tatctttgta gttaccgatt gattgcttgc agacacaccg        720 ggggtra                                                                  727

<210> SEQ ID NO 78
<211> LENGTH: 350
<212> TYPE: DNA
<213> ORGANISM: Lycopersicon esculentum

<400> SEQUENCE: 78
agggagahta gamccagaag tgtcaccaag aacctatctt caagaactac agcttgcctc         60
ctaataaatg tggatacccc ggtggtattt tcaacccact caactttgca ccaactgaag        120
aggccaagga gaaggaactt gctaatggta agtggatgtt cactttctct aaatgaytt         180 atatacctga accaggctaa ttattttagg tggataattt gcaggagat tggctatgtt         240 ggcattttg ggatttatag tgcagcacaa tgtgactggg aagggacctt ttgacaacct        300
tctgcagcac ctctctgacc catggcacaa caccatcatc caaacactca                    350

<210> SEQ ID NO 79
<211> LENGTH: 240
<212> TYPE: DNA
<213> ORGANISM: Lycopersicon esculentum

<400> SEQUENCE: 79
gactmctggc tktaatgttg cattggtagc caagtgacac ccctgttgct cattgcttga         60
aggtttggct gatttggaag ttgcagcttg tctttgcact gccattaagg ctaatgtact        120
tgggattgtc aaattagata ttcctgttgc tcttagtgct tggttagtg cttgtgctaa         180 gaaagttccc acaggtttca gtgtggtta attagagtat taattagcca agggtgggga        240
```

<210> SEQ ID NO 80
<211> LENGTH: 389
<212> TYPE: DNA
<213> ORGANISM: Lycopersicon esculentum

<400> SEQUENCE: 80

| | | | | | |
|---|---|---|---|---|---|
| maaakctaaa | yyaaggcttk | atttkgacca | accctkgtaa | tccattaggt | accatttag | 60 |
| atagggacac | acttaaaaaa | atctccacyt | tcactaacga | acataatatc | catcttgttt | 120 |
| gcgacgaaat | atatgctgct | accgtrttca | atyctccaaa | attcgttagc | atcgctgaaa | 180 |
| ttatcaacga | agataattgt | atcaataaag | atttagtaca | cattgtgtct | agtctttcca | 240 |
| aggacttagg | ttttccagga | tttcgagtgg | gaattgtgta | ctcrttcaac | gatgatgttg | 300 |
| ttaactgtgc | tagaaaaatg | tcgagttttkg | ggtcttgttt | cgactcagac | acaacatttg | 360 |
| ctagctttca | tgttgtctga | cgatgaatt | | | | 389 |

<210> SEQ ID NO 81
<211> LENGTH: 389
<212> TYPE: DNA
<213> ORGANISM: Lycopersicon esculentum

<400> SEQUENCE: 81

| | | | | | |
|---|---|---|---|---|---|
| maaakctaaa | yyaaggcttk | atttkgacca | accctkgtaa | tccattaggt | accatttag | 60 |
| atagggacac | acttaaaaaa | atctccacyt | tcactaacga | acataatatc | catcttgttt | 120 |
| gcgacgaaat | atatgctgct | accgtrttca | atyctccaaa | attcgttagc | atcgctgaaa | 180 |
| ttatcaacga | agataattgt | atcaataaag | atttagtaca | cattgtgtct | agtctttcca | 240 |
| aggacttagg | ttttccagga | tttcgagtgg | gaattgtgta | ctcrttcaac | gatgatgttg | 300 |
| ttaactgtgc | tagaaaaatg | tcgagttttkg | ggtcttgttt | cgactcagac | acaacatttg | 360 |
| ctagctttca | tgttgtctga | cgatgaatt | | | | 389 |

<210> SEQ ID NO 82
<211> LENGTH: 489
<212> TYPE: DNA
<213> ORGANISM: Lycopersicon esculentum

<400> SEQUENCE: 82

| | | | | | |
|---|---|---|---|---|---|
| agacgacmcc | amgctaaagg | agaaacacaa | gaagcattta | aaaagaacat | tgaagcagca | 60 |
| actaagtttc | ttttgcaaaa | gatcaaggac | ttgcaattgt | atgtccattt | taaattgttt | 120 |
| tatgacattg | tctaagctat | ttcttactga | agttgaatgt | gttttgtttt | ccttctactt | 180 |
| catacctggc | acctttaata | gaaactgata | ctatttgtgt | gtgtgctggc | agctttgttg | 240 |
| gtgagagcat | gcatgatgat | ggcgccctgg | tgtttgcgta | ctacaaggag | ggttcagctg | 300 |
| atcctacctt | tttgtacatt | gcacctggtt | tgaaggagat | caagtgctag | atgtctggtg | 360 |
| gagtgcttct | gctagaagtt | ttgcattcga | gattatgttt | catgtagttt | ttaatatttg | 420 |
| gtcttttttg | cttatttatg | tctggtgttt | cttctaaacc | ttgggtactt | gctgtgacca | 480 |
| gtaccggaa | | | | | | 489 |

<210> SEQ ID NO 83
<211> LENGTH: 754
<212> TYPE: DNA
<213> ORGANISM: Lycopersicon esculentum
<220> FEATURE:
<221> NAME/KEY: misc_feature
<222> LOCATION: (749)..(749)

```
<223> OTHER INFORMATION: W=A or T; M=A or C; R=A or G; Y=C or T; K=G or
      T; S=G or C; H=A, C or T; B=C, G or T; V=A, C or G; D=A, G or T;
      N=A, C, G or T

<400> SEQUENCE: 83
tgggggyyca ttacacaaaa caagaacttc agccattgtg tgttgttcaa accaaacccc      60
gtggtttcta attaacaga ggaaagttct tcttcattaa aggcattctc tgcagcactt      120
gcgtttgtct tctattcttt tgtcagcacc agttcttcca gcttctgctg acatctctgg     180
cttacacctt gcaaggactc aaaacagttt gctaaaaggg agaagcaaca gatcaagaag     240
cttcaaaatt ctttgaaact ttatgcacct gatagcgccc ctgcacttgc tatcaatgcc     300
actattgaga aaactaaacg caggtttgcc ttcagtatct ttcttcacaa ttttcaaaaa     360
gttttacttc ttatttgcct attkkccct agttgatcat tttttattg tgtactagat      420 agagagtact tatagttaag atttgcggga ttctaatcaa ttttgttagg ggtttacaaa    480
ttaaaataca tagtacaaat atagggtcta tggaaaagct actgaattcg ttcgaacccca   540 tgttaggagt aggagtagaa gaagagctaa aagtattctt ktacgaatga aagcatactg    600
tacattamca tttgcttatc agagaaaagc agattgttca acttttcctk ggcatatgcc    660
gttgagatta gactaggaaa ctccacatwg aacatacata taccskttga tactcgagta    720
agtaaaagtt taatycmtca gacgtcccnc acta                                754

<210> SEQ ID NO 84
<211> LENGTH: 251
<212> TYPE: DNA
<213> ORGANISM: Lycopersicon esculentum

<400> SEQUENCE: 84
acaccgwgag argaagatag cttttacaat tcttcgccat gacaggaatc ttcttctgag    60
tatgagatcg ctgggcaaa agtaccgcat aaacgacctc gaggaggata acgccgcgct    120
caaggaagaa caagaagggc tcgttcaccg aatgaaccat atcaagcaaa gtctacttgc   180
tgaagctgct agtgagccca ctggtgcctt tgcttcccgt cttcgccgcc tctttggtga    240
tgaaagctga a                                                        251

<210> SEQ ID NO 85
<211> LENGTH: 539
<212> TYPE: DNA
<213> ORGANISM: Lycopersicon esculentum

<400> SEQUENCE: 85
aayggstgtg gayctggctg cagtgcggca gtggctgtgg agggtaagtt cttcctaaaa    60
tatttatatg ttacataaat ataacgac tttcatttaa aaaaaaatca tagaatcgag     120
atgatctagt ttacagttta atttattcct ttcactaaat ttaattatct aaattcttga    180
ttttgtataa ttaattgcag atgtgggatg taccccgact ggagagcac cactaccttt    240 accatcattg agggtgttgc acctatgaag aagttagtct aattttaaca taaaagactt    300
tttctacatt tgttatatat gatcggaatg attacgaagt aatttagaa ttcattaaca    360 aaattaagaa gtttcactct cgaaatttga attataacac ataaattgaa acaggtcacc    420
taaaagataa ctataatgtt agaattaata atattgaaac acataacacg ttctattaat    480
atgaattttg tttaccatat taaagtgtat atatatataa tttacatgaa ttaattgcg    539

<210> SEQ ID NO 86
<211> LENGTH: 521
```

<212> TYPE: DNA
<213> ORGANISM: Lycopersicon esculentum

<400> SEQUENCE: 86

```
tggtaagatg tgcttatgag gtctgtcgat attcccttct gaaaagatct tcaatcccac      60
ttgaaatcat acccattaaa caatcagagt taagagaaaa agggttatac tggcgtgraa     120
gagggaaatt agaaagcact gagttttcat ttactcgttt tttgacaccc catttggcta     180
attttgaagg atgggctatg tattgttgat tgtgatttct tgtatttagg ggatattaag     240
gaattgaggg atatggtgga tgataaatat gctttaatgt gtgtacaaca taattatgct     300
cctaaagaaa ctactaaaat ggatggggca gtacaaactg tgtatcctag aagaattgg      360
tcatccatgg ttcttctata attgtgcgca tccaaagaat aaggtcttga cacctgakak     420
ttgtcaatac tgaaactggg gcattttctc cataagcttt actatggttg gaakatgagg     480
agattgggga agttccgttc gttkggaact tccgtcgatc g                         521
```

<210> SEQ ID NO 87
<211> LENGTH: 654
<212> TYPE: DNA
<213> ORGANISM: Lycopersicon esculentum

<400> SEQUENCE: 87

```
aarggagyaa gtgkgatyct cgaatmcatt gacgagacat ttgaaggccc ttccatctta     60
cctaaagacc cttatgatcg agctttagct cgtttctggg ctaaattctt cgaagataag    120
gtatatcgac tccttaactt gtctctactc tgttaattga atattctaac ttawaaatga    180
tcaactatac atctccaaaa tttatgtggc atgtcatgag gtgtctacga gacatgttaa    240
agagttggag tgcttaattg ttaattgaga ccaaatattt agatatgcac attcaaagtt    300
agagtactta ttatcggata caaccaagtc agaatgtcat tttatatata ttatatgtct    360
tgtgtaaaat tggactaaag taataaaata tcacattgcc aacaataact tatttgtgac    420
tgactaatgt acttctattg ttgtagattt atatctttaa aattttgttg aattyaagtt    480
ccaattgtta tgtagtggcc atcaatgatg aaaagtctat ttttcaaagg agaggagcaa    540
gagaaaggta cmgaggaagt taatgagatg ttgaaaattc ttgataatga gctcagggac    600
gramagtttt tgttggtaa caactttgga ttgktgatgt tgtgcaatgc tgta            654
```

<210> SEQ ID NO 88
<211> LENGTH: 356
<212> TYPE: DNA
<213> ORGANISM: Lycopersicon esculentum

<400> SEQUENCE: 88

```
aaagkggcag aattagaacc aggaagtgtc accaagacct atcttcaaga actacagctt     60
gcctcctaat aaatgtggat accctggtgg tatttttcaac ccactcaact ttggcaccaa   120
mctgaagagg ccaaggagaa ggaacttgct aatggtaagt ggatgttcac tttctctaaa   180
tgaytttata tacctgaacc aggctaatta ttttaggtgg ataatttgca gggagattgg   240
ctatgttggc attttggga tttatagtgc agcacaatgt gactgggaag ggacctttg     300
acaaccttct gcagcacctc tctgacccat ggcacaacac catcatccaa acacaa       356
```

<210> SEQ ID NO 89
<211> LENGTH: 824
<212> TYPE: DNA
<213> ORGANISM: Lycopersicon esculentum

```
<400> SEQUENCE: 89
graaggagga tctgatgctt ctggcacaat gggtttagtt ttsgcaaatt tttgtatatc      60
aaaaatttac taaattttta tacrcactct tttcttttta atctgttata aaaataatta     120
cttatacaat tttatcayta atcatgacat gctcttaatg tcacgtgtca tatttaagac     180
catgattttt attagatata cttttgatat atcgtaaaac tctttatatt gtctaatttc     240
atgttcattc aaatattcta cgaaattaga atttgaaact tttgattttt ttgtagtttt     300 agtcttttg agtcatcaga ttctaaattg atggtatata ttaaataaat ttggttgagt     360
cgaatataaa rtattagtca aattagtgaa ttctgtcaaa ctcgcttctt atctttagc     420 tttatctatc ccttcgtaaa ataatagtga aacatatatg aatttttttt aatagtctaa     480
attttatttt cacgaaaatt tttatgctca atcaaatact gttttacgaa ataagataga     540
aggatagtta taatgacatg aattctgatt attaacaatg attgtctgga acagggcggt     600
gcttgtggct atgggaactt gtactcaaac aggttatggt acaaacactg ctgcattaag     660
tactgccttt gttcaatgat ggagcatcat gtggtcatgt tcccmtttgt gtgattmtca     720
tccgatcmaw kkgtsymtrg gractcytta catttmcgcc tatttgyccc cawkykhych     780
ckgcmccccb sbssbbmhhm ahhwmhaaca acaacaaaac aata                      824

<210> SEQ ID NO 90
<211> LENGTH: 395
<212> TYPE: DNA
<213> ORGANISM: Lycopersicon esculentum

<400> SEQUENCE: 90
aaagcacaga aacagagatt atgaacaaca tacaacccaa ttagccaaaa gttcttagtt      60
ctggttgaca tgtcaaataa gatcctaggg acataataaa ttccagaaca ctggtcaaat     120
cacatcagaa tcaaaccccca actacaaata atggataata agaagggaa acacaattaa     180 tgatgtaaat tgagttagac ctaacaagtt acaccaatgc aatgctgctc tcaccacctg     240
gaggcttgcg aacccgcca tagaagtctc gagattctac tttcccatct gcaaatatat     300
tgcttccact catttctcgc aactttgctg aactcaggtg cttctcagct gatgttggag     360
gattatcgcc cttgaatatg tcatttcctg tggaa                                 395

<210> SEQ ID NO 91
<211> LENGTH: 318
<212> TYPE: DNA
<213> ORGANISM: Lycopersicon esculentum
<220> FEATURE:
<221> NAME/KEY: misc_feature
<222> LOCATION: (315)..(315)
<223> OTHER INFORMATION: W=A or T; M=A or C; R=A or G; Y=C or T; K=G or
      T; S=G or C; H=A, C or T; B=C, G or T; V=A, C or G; D=A, G or T;
      N=A, C, G or T
<220> FEATURE:
<221> NAME/KEY: misc_feature
<222> LOCATION: (316)..(316)
<223> OTHER INFORMATION: W=A or T; M=A or C; R=A or G; Y=C or T; K=G or
      T; S=G or C; H=A, C or T; B=C, G or T; V=A, C or G; D=A, G or T;
      N=A, C, G or T
<220> FEATURE:
<221> NAME/KEY: misc_feature
<222> LOCATION: (318)..(318)
<223> OTHER INFORMATION: W=A or T; M=A or C; R=A or G; Y=C or T; K=G or
      T; S=G or C; H=A, C or T; B=C, G or T; V=A, C or G; D=A, G or T;
      N=A, C, G or T

<400> SEQUENCE: 91
tttgaaccgt ttgtrccacy gacttacwtt tkkgamaaga smcmaccaag agttgaggct      60
```

```
ttcttgcrgc cattgccagt aaggtyctca aagactactt cagcatcaaa accaccaaag      120
tttcaagtga aggcttcgct taagsagaaa gctttgacag gactgacagc agctgcactc      180
actgcttcca tggtcatgcc tgatgtagcc gaagcagcag agagtgtttc accatcccta      240
aagaactttt tgctcagcat ttctgcaggt ggagttgtgc ttgctgcaat tcttggcgct      300
ataattggtg tttannan                                                   318

<210> SEQ ID NO 92
<211> LENGTH: 595
<212> TYPE: DNA
<213> ORGANISM: Lycopersicon esculentum
<220> FEATURE:
<221> NAME/KEY: misc_feature
<222> LOCATION: (418)..(418)
<223> OTHER INFORMATION: W=A or T; M=A or C; R=A or G; Y=C or T; K=G or
      T; S=G or C; H=A, C or T; B=C, G or T; V=A, C or G; D=A, G or T;
      N=A, C, G or T
<220> FEATURE:
<221> NAME/KEY: misc_feature
<222> LOCATION: (433)..(433)
<223> OTHER INFORMATION: W=A or T; M=A or C; R=A or G; Y=C or T; K=G or
      T; S=G or C; H=A, C or T; B=C, G or T; V=A, C or G; D=A, G or T;
      N=A, C, G or T
<220> FEATURE:
<221> NAME/KEY: misc_feature
<222> LOCATION: (484)..(484)
<223> OTHER INFORMATION: W=A or T; M=A or C; R=A or G; Y=C or T; K=G or
      T; S=G or C; H=A, C or T; B=C, G or T; V=A, C or G; D=A, G or T;
      N=A, C, G or T
<220> FEATURE:
<221> NAME/KEY: misc_feature
<222> LOCATION: (549)..(549)
<223> OTHER INFORMATION: W=A or T; M=A or C; R=A or G; Y=C or T; K=G or
      T; S=G or C; H=A, C or T; B=C, G or T; V=A, C or G; D=A, G or T;
      N=A, C, G or T

<400> SEQUENCE: 92
cacgasagag ggttgacagt acggatgatt tttttcaaaa acaggatatt tttttcgatt       60
cactaaagaa aataaaagtg cttttaacca agtggttcct gattttggag ccgtaacgag      120
aatgatatca ttatcttgag cttgatattg tcgttgacat gcaatcaccc cttggataag      180
tcttggtaat gcccaaaagc cttgataatt atacacataa gatccaaccc atcctctttc      240
ttttggtagg gtagaaagca atttcttaca atcttcactt acatcatctt cttgtaaata      300
tttrtgagga gttggtgaag aggtttgaga aagggctcgc aacagaaacc agccgcgatg      360
cggcgtcgga ccaggggcaa gagcacccca gcgaacgcat cacaacggcc ccctcgcnca      420
caataacaac agnacaacac tcacacgcgg cgwagatccc gccatcccaa caacgcccac      480
caanaataca accccccccca gaccaccttc actaccccac tccacscttc acggccaacc      540
acacacaanc aatcgaaacc acccggtcca caaacgcaca aacacaacga cacca           595

<210> SEQ ID NO 93
<211> LENGTH: 342
<212> TYPE: DNA
<213> ORGANISM: Lycopersicon esculentum

<400> SEQUENCE: 93
cagagaagay tttgcacatt cagctccckg gtgaggkgca cagtagaaag tgtaagttcc       60
tttctcactc aaagtgacac tgtatgtctc tcctgctgca ttcagaagat cctcttcaga      120
acatggaaat cttactagca tccacaccag ctgggatttc atcttcatca aatacgacgt      180
tgtgtgggaa ccctgcattg ttcttgaatg taattttctc accagcacta acgctgaagt      240
```

| | |
|---|---|
| tcccaggaat aaaagctaga ctcccatcat caccaccaag caacacttca agtgccatgg | 300 |
| cattgctagc aagcatcgcg ctaacagcgg tggcasmaaa aa | 342 |

<210> SEQ ID NO 94
<211> LENGTH: 434
<212> TYPE: DNA
<213> ORGANISM: Lycopersicon esculentum

<400> SEQUENCE: 94

| | |
|---|---|
| gagaatgwwc taatcatccc attccaatgg tttataacaa ctggccataa aataaaaaac | 60 |
| taaaatatac gaaggagcat attcccagag agtatgacat gctctgatcc aagaacaaga | 120 |
| taaagacatt ctaaaactta caaccatcat cactcagaac gattggcata cctctccacc | 180 |
| ttttcatcaa gattgattcc aaccatagcc tcaccaagcc cacagctaat ttcagccagc | 240 |
| aattgtgggt cactgtaatg agtcactgct tgcacgatgg cacgtcccct ctttgcaggg | 300 |
| tcaccactct tgaagatacc agaacccacg aacacgccgt cacatcccaa ctgcatcata | 360 |
| agcgctgcat ctgctggtgt cgccacccca cctgctgcaa agtgaaccac agggagccta | 420 |
| ccaagttgct ttgt | 434 |

<210> SEQ ID NO 95
<211> LENGTH: 472
<212> TYPE: DNA
<213> ORGANISM: Lycopersicon esculentum

<400> SEQUENCE: 95

| | |
|---|---|
| tatccactca ggtctccgca agccagaaat gggatataca ccttgttacg accytcaagc | 60 |
| catccactac tgcaatctgt catgtcacag atgttcggaa gataatgtat aagtacaact | 120 |
| atatagtcgg awttgcatct agtctagcat tcggaaaatg gaagccatgc tacttctagc | 180 |
| ataaaaaaca gcagctagaa atcgtaactc caatgatacg aggaagtatt cagagtttag | 240 |
| agtgawgtac aatgcaattt agagaacaag catctgcaca tcraagttac ctaggtcctc | 300 |
| agcgcctgat ggacttccaa cttgttcaag aaggcgataa aggtctttct cattgaatcc | 360 |
| ttcaggtgga gagtagtttt cacaaactgc aaatgcctct gcacagcgga aagattgaat | 420 |
| tagatttatg ttatatagcc attctagtct tgctttaatg gatctttctc ga | 472 |

<210> SEQ ID NO 96
<211> LENGTH: 222
<212> TYPE: DNA
<213> ORGANISM: Lycopersicon esculentum

<400> SEQUENCE: 96

| | |
|---|---|
| ccacagtttc atgctgcacc tacatgtgta agcaactatc atagcaagtc tcggaacaat | 60 |
| tggtaggaaa aaatcmykta aggatatgaa acatactgty ctttcttcat ctgagtctgy | 120 |
| agagttaatt tttaactctt gggataaatg caaagawtta gacatggakg agtycttaac | 180 |
| acgtccagac aagaggcgta acacaggtac acctttttctc ga | 222 |

<210> SEQ ID NO 97
<211> LENGTH: 133
<212> TYPE: DNA
<213> ORGANISM: Lycopersicon esculentum

<400> SEQUENCE: 97

| | |
|---|---|
| ttgtgcttga tgaattgtag gtccagtgca ggtttgcttc taaaacaggg agcactttgc | 60 |
| aagtggtgaa agttctatta gctgggaaag tgtagtttga gcagttttga gctgarttaa | 120 |

<210> SEQ ID NO 98
<211> LENGTH: 249
<212> TYPE: DNA
<213> ORGANISM: Lycopersicon esculentum

<400> SEQUENCE: 98

```
ccgccactgg gtaattgagt ttcatattga tggttttgtt tttgttracg cttcttcctt      60
gttgagaggg ttcaatggag agattctatc tcgtcctcca ttagttgaag ctattgcctt     120
tgatcctatc ctttcaaagg ycaagatgat tgcagataat tggaatccat taaccaatga     180
ttctacggaa aatttattcc ctcactggag gagatgggca gagataaata tgagattttg     240
tgatgacat                                                             249
```

<210> SEQ ID NO 99
<211> LENGTH: 284
<212> TYPE: DNA
<213> ORGANISM: Lycopersicon esculentum

<400> SEQUENCE: 99

```
tcgagtaagg cggatggata tggaacaagc catttcaagg agcaatttcc caggattttc      60
agctttgcaa cagcagaagt gtayctctgc agagatagat cataaccttt ggaaaggtgt     120
agtaattgtc aaagggagga atgagccagg aaactgatag actatgttgc gaaaataagc     180
tatacttcac taaaaaaagg ctagacgttt gagaaatgaa gcaagaacta acacctctca     240
ccaattgcat cattttctta gttcagttga tgtgatgagc ttgt                      284
```

<210> SEQ ID NO 100
<211> LENGTH: 320
<212> TYPE: DNA
<213> ORGANISM: Lycopersicon esculentum

<400> SEQUENCE: 100

```
tcgatatccw ctcttgtttg ttgcaggagc wgaactataa attgcttgca ggaaccttga      60
catatgcttt ctgttgagac ttgaatcacc agcatggatt tgaatgcctt gccacagcca     120
gaggatgacg aygagatttt tggacaacaa ttagaagatg aaccacaaga acctatttta     180
cgtagtgatg agcstgcaga ttatgtcacg agtgctgtag agatttcacg tcgcgtatgt     240
ttctgcttat actgctcgct gtatcaacta ttgaacygta ctactacttg arcttgctcg     300
tttattggat atttcttttt                                                 320
```

<210> SEQ ID NO 101
<211> LENGTH: 191
<212> TYPE: DNA
<213> ORGANISM: Lycopersicon esculentum

<400> SEQUENCE: 101

```
gaattcacac tasgttcgat gaaattgaaa cgttctcttt ctgaagaaka tacacaagaa      60
aaaatcttat agtcctcaac aatattcttc ttcgtaacag aaaacacgga agaaaatctc     120
ttctgaaaat ccctataatc actggctgga acttctccsa actctcaatt tttcaacctt     180
ctctatgtta a                                                          191
```

<210> SEQ ID NO 102
<211> LENGTH: 279
<212> TYPE: DNA

<213> ORGANISM: Lycopersicon esculentum

<400> SEQUENCE: 102

| | |
|---|---|
| ctgcagaadt actgtttgtt caggacttac taaatatcct aaacaaaatt gatgatagag | 60 |
| ccaataatgt atgcatgatt ggcggtccrt tcttttgtta tagcaagagc ttgaagctaa | 120 |
| ttttgtttgt cataatggcc gcactaattg tttattatct cagaatgaac aaaaagaagc | 180 |
| aagtcagaag ctttstactc tatactgaac aactttggaa ttggaactat gtacttatct | 240 |
| agccacgcct catagatctt tgtggtttag gagtgttaa | 279 |

<210> SEQ ID NO 103
<211> LENGTH: 336
<212> TYPE: DNA
<213> ORGANISM: Lycopersicon esculentum

<400> SEQUENCE: 103

| | |
|---|---|
| gaattcacaa tgaaaaakgk dgtaaaaaca cgaaatcaat caagcatgca agagataatg | 60 |
| ttgtccatcc agttgttgtt gatgtttcgg tattgtatgt gtgttgggag gagttatctg | 120 |
| grcagcaagt cgaggtttga acgtcaaaaa ggtatgggtt gtcttctctc tttgtcccct | 180 |
| ttcgaagaga cccctaaggt tcagacgaat ctattccaaa aactagggtt gttccttgtt | 240 |
| gcatctcctt ktcacaagct cccatcgcat cataagtagg gtatgtttga tggtagaatt | 300 |
| tacggatgta atttactttt gaaatgatta tgttaa | 336 |

<210> SEQ ID NO 104
<211> LENGTH: 373
<212> TYPE: DNA
<213> ORGANISM: Lycopersicon esculentum

<400> SEQUENCE: 104

| | |
|---|---|
| agagagacga gagctcgact agtgatagtg ttatgtgcaa cagttgaata gaaagatgya | 60 |
| cacgagcctc ggatcaatgg cagggaaaga ggcgtggtgc tacgaaccat aaaggcaagg | 120 |
| ttgagctttc ctttacagag tacatcgcct attccatact ccgctgatac tctttgataa | 180 |
| atcaaaatct gtggtgatct cgtagttctt ggggatccca gccaaaacca ccttcgaggt | 240 |
| tcaacacaac atagacagta tggcagaata tcaagacaat gactgctcga aactgctgat | 300 |
| ggcattatgt gcaaccgttg aatagagaga tgtacacgag tctcggatca atggcaggaa | 360 |
| aagagagtgc ttg | 373 |

<210> SEQ ID NO 105
<211> LENGTH: 336
<212> TYPE: DNA
<213> ORGANISM: Lycopersicon esculentum

<400> SEQUENCE: 105

| | |
|---|---|
| gaattcacaa tgaaaaakgk dgtaaaaaca cgaaatcaat caagcatgca agagataatg | 60 |
| ttgtccatcc agttgttgtt gatgtttcgg tattgtatgt gtgttgggag gagttatctg | 120 |
| grcagcaagt cgaggtttga acgtcaaaaa ggtatgggtt gtcttctctc tttgtcccct | 180 |
| ttcgaagaga cccctaaggt tcagacgaat ctattccaaa aactagggtt gttccttgtt | 240 |
| gcatctcctt ktcacaagct cccatcgcat cataagtagg gtatgtttga tggtagaatt | 300 |
| tacggatgta atttactttt gaaatgatta tgttaa | 336 |

<210> SEQ ID NO 106
<211> LENGTH: 261

```
<212> TYPE: DNA
<213> ORGANISM: Lycopersicon esculentum

<400> SEQUENCE: 106
ctgcagaatt tgacttacat tttcctaatg aatctgatga taaggtgcta gatgatcyta      60
stktgtatca gaagctagta ggaaggttgc tttatctgac aataacaaga ccagacatag     120
ytttygyagt gyagctcttg agtcagttca tgcatagtcc taaagcatct tacatgsaag     180
ctgmaatgrr ggtggtaaga tatgtcaagc aggcaccagg actgggtata cttatggcag     240
ccaatacaac tgatcagtta a                                               261

<210> SEQ ID NO 107
<211> LENGTH: 450
<212> TYPE: DNA
<213> ORGANISM: Lycopersicon esculentum

<400> SEQUENCE: 107
ctgcagatgg tggtgacatt acaggaggtg gtgcaaccag cccaaaaggc gggatcgtaa      60
tgttatgatc acaaggtgga ggcacaggaa gactggtatt attatgttca gatggcaaag     120
tggcaccttc caggacttga tcaatgccat ggcatctgat ggaagcactt ttagtgcaga     180
tatttggact aacgactcga gcathgttga gaaacaaatg catgtatcca gaattgttga     240
ctctgaggaa aaggtcaggt tttgaagttg gtatcatgga tcctgttggg aagtgttgga     300
ggtggtcaaa aagcaacggt gatggtaagg aatgtcgttg caagaaatct accacgttgt     360
tttcttgtat tagtgtttgg gacagtgtct trtctcttgg catcaagaaa gtgatgtttc     420
cttttacaag gtcatcaggg gccatgttaa                                      450

<210> SEQ ID NO 108
<211> LENGTH: 124
<212> TYPE: DNA
<213> ORGANISM: Lycopersicon esculentum

<400> SEQUENCE: 108
ctgcagaasc agtacatagg ttgtattgam acctgtatt acaataagga gactctartg      60
ataccgacct atccctataa tgagtctaag acatcaayga tagagaygrt accattagag     120
ttaa                                                                  124

<210> SEQ ID NO 109
<211> LENGTH: 149
<212> TYPE: DNA
<213> ORGANISM: Lycopersicon esculentum

<400> SEQUENCE: 109
gacaagtaat ggttctaagt tgagggtgtt gatgtgctay gaaatattgr gacatttgat      60
gtttgataag tataagtatg aactaatact aaattaagtg aagttttat gatttgrtat     120 ttttgttgaa tgtgtaagca aaatctcga                                       149

<210> SEQ ID NO 110
<211> LENGTH: 267
<212> TYPE: DNA
<213> ORGANISM: Lycopersicon esculentum

<400> SEQUENCE: 110
ctgcagaaag tgattcggtt ggagatgcag ttacacgaag cactcttaca tcggcttctg      60 ctgggggtaga caaatatgct tcgactaact gtccacattc tgcttcttca tttgattatg     120
```

```
ttgtcagtac atttgatgag ggacatcatc agacaaaagt cttcagctct ttggattgtc      180
acaaggagtc aaaaatatct aatactaaca agaaaaggag acggtctggt gatagtcata      240
agcccagacc acgagatagg cagttaa                                          267

<210> SEQ ID NO 111
<211> LENGTH: 210
<212> TYPE: DNA
<213> ORGANISM: Lycopersicon esculentum

<400> SEQUENCE: 111
ctgcagaagt cacactgaas tcataccaaa gaccatttca actgctaaca ttagactaga       60
agagaacctt ccatgactgc cacagctttc cctctcagam atacccctctg cttctcatcg     120 tctagatgca gtttcacgac gccacctcta ggtgaggcct ggaccayaat acaataaaat      180
caatagggca aagagaact atgaggttaa                                        210

<210> SEQ ID NO 112
<211> LENGTH: 165
<212> TYPE: DNA
<213> ORGANISM: Lycopersicon esculentum

<400> SEQUENCE: 112
ctgcagaaag atatagccag aggaaggtgg agcaatttca tgtggatagg wtgcataatg       60
catgttcttw ctttatttcg tatcttggtg aagcatagat atagacagat camagaagca     120
catygggatc taccacctac caagatgctc tcattttaca gttaa                      165

<210> SEQ ID NO 113
<211> LENGTH: 373
<212> TYPE: DNA
<213> ORGANISM: Lycopersicon esculentum

<400> SEQUENCE: 113
agagagacga gagctcgact agtgatagtg ttatgtgcaa cagttgaata gaaagatgya       60
cacgagcctc ggatcaatgg cagggaaaga ggcgtggtgc tacgaaccat aaaggcaagg     120
ttgagctttc ctttacagag tacatcgcct attccatact ccgctgatac tctttgataa     180
atcaaaatct gtggtgatct cgtagttctt ggggatccca gccaaaacca ccttcgaggt     240
tcaacacaac atagacagta tggcagaata tcaagacaat gactgctcga aactgctgat     300
ggcattatgt gcaaccgttg aatagagaga tgtacacgag tctcggatca atggcaggaa     360
aagagagtgc ttg                                                         373

<210> SEQ ID NO 114
<211> LENGTH: 312
<212> TYPE: DNA
<213> ORGANISM: Lycopersicon esculentum

<400> SEQUENCE: 114
ctgcagaatg gatatttcaa tctttgccat caaatactgg ctagatcgtt gcaatcgctc       60
cttgaattga acaaactcaa taacctaaaa aagttcacag atgaagattt tgttaccatt     120
gggctagctc attgtatgat tactaatttta tcttttcgtt cacaaakgga accattagta     180
tttgaaatga tcctaagaga gaatcgtcat gataagcaay gtaagtttct acaccagaaa     240
ataaataatt gctccaacaa atacccactc aagactcact tcgcaagaac taagttgtcc     300
agaaacagtt aa                                                          312
```

<210> SEQ ID NO 115
<211> LENGTH: 124
<212> TYPE: DNA
<213> ORGANISM: Artificial Sequence
<220> FEATURE:
<223> OTHER INFORMATION: Oligonucleotide probe

<400> SEQUENCE: 115

```
cacatacttg aggcagtaag tgagtgaatt ggtacgcagt cgatgagtcc tgagtaaagt    60
caggcattcg actagcgtat acgcagatcc gatcgattta taattaaagt caaattagaa   120
acca                                                                124
```

<210> SEQ ID NO 116
<211> LENGTH: 122
<212> TYPE: DNA
<213> ORGANISM: Artificial Sequence
<220> FEATURE:
<223> OTHER INFORMATION: Oligonucleotide probe

<400> SEQUENCE: 116

```
cacatacttg aggcagtaag tgagtgaatt ggtacgcagt cgatgagtcc tgagtaaagt    60
caggcattcg actagcgtat acggatccga tcgatttata attaaagtca aattagaaac   120
ct                                                                  122
```

<210> SEQ ID NO 117
<211> LENGTH: 119
<212> TYPE: DNA
<213> ORGANISM: Artificial Sequence
<220> FEATURE:
<223> OTHER INFORMATION: Oligonucleotide probe

<400> SEQUENCE: 117

```
aaattcgaga cattctttat caaaggtgaa ttggtacgca gtcgatgagt cctgagtaaa    60
gcatcgactg gtactacgga ctcagatccg atgatttcag ttgtttacca ttcatattg    119
```

<210> SEQ ID NO 118
<211> LENGTH: 117
<212> TYPE: DNA
<213> ORGANISM: Artificial Sequence
<220> FEATURE:
<223> OTHER INFORMATION: Oligonucleotide probe

<400> SEQUENCE: 118

```
aatatgaatg gtaaacaact gaaatcgtga attggtacgc agtcgatgag tcctgagtaa    60
agcatcgact ggtactacgg actgatccga tctttgataa agaatgtctc gaatttt      117
```

<210> SEQ ID NO 119
<211> LENGTH: 114
<212> TYPE: DNA
<213> ORGANISM: Artificial Sequence
<220> FEATURE:
<223> OTHER INFORMATION: Oligonucleotide probe

<400> SEQUENCE: 119

```
atttccagga tattgcttag tttctgtgaa ttggtacgca gtcgatgagt cctgagtaaa    60
gtcagtcatg gatccgatca gatccgaaat aaatggaaag ttatatggaa aaac         114
```

<210> SEQ ID NO 120
<211> LENGTH: 112
<212> TYPE: DNA
<213> ORGANISM: Artificial Sequence
<220> FEATURE:
```

<223> OTHER INFORMATION: Oligonucleotide probe

<400> SEQUENCE: 120
atttccagga tattgcttag tttctgtgaa ttggtacgca gtcgatgagt cctgagtaaa    60
gtcagtcatg gatccgatga tccgaaataa atggaaagtt atatggaaaa ag    112

<210> SEQ ID NO 121
<211> LENGTH: 109
<212> TYPE: DNA
<213> ORGANISM: Artificial Sequence
<220> FEATURE:
<223> OTHER INFORMATION: Oligonucleotide probe

<400> SEQUENCE: 121
tttatatacc tgaaccaggc taattagtga attggtacgc agtcgatgag tcctgagtaa    60
agtctaacgt tacggcatga tccgtggatg ttcactttct ctaaatgac    109

<210> SEQ ID NO 122
<211> LENGTH: 107
<212> TYPE: DNA
<213> ORGANISM: Artificial Sequence
<220> FEATURE:
<223> OTHER INFORMATION: Oligonucleotide probe

<400> SEQUENCE: 122
tttatatacc tgaaccaggc taattagtga attggtacgc agtcgatgag tcctgagtaa    60
agtctaacgt tacggcatga tctggatgtt cactttctct aaatgat    107

<210> SEQ ID NO 123
<211> LENGTH: 104
<212> TYPE: DNA
<213> ORGANISM: Artificial Sequence
<220> FEATURE:
<223> OTHER INFORMATION: Oligonucleotide probe

<400> SEQUENCE: 123
cttgggattg tcaaattaga tattccgtga attggtacgc agtcgatgag tcctgagtaa    60
agtgatcagc tgatccgatc tgcactgcca ttaaggctaa tgta    104

<210> SEQ ID NO 124
<211> LENGTH: 102
<212> TYPE: DNA
<213> ORGANISM: Artificial Sequence
<220> FEATURE:
<223> OTHER INFORMATION: Oligonucleotide probe

<400> SEQUENCE: 124
cttgggattg tcaaattaga tattccgtga attggtacgc agtcgatgag tcctgagtaa    60
agtgatcagc tgatccgatg cactgccatt aaggctaatg tg    102

<210> SEQ ID NO 125
<211> LENGTH: 99
<212> TYPE: DNA
<213> ORGANISM: Artificial Sequence
<220> FEATURE:
<223> OTHER INFORMATION: Oligonucleotide probe

<400> SEQUENCE: 125
ttcactaacg aacataatat ccatctgtga attggtacgc agtcgatgag tcctgagtaa    60
agtcatacgt tacgggacac acttaaaaaa atctccacc    99

<210> SEQ ID NO 126
<211> LENGTH: 97
<212> TYPE: DNA
<213> ORGANISM: Artificial Sequence
<220> FEATURE:
<223> OTHER INFORMATION: Oligonucleotide probe

<400> SEQUENCE: 126
ttcactaacg aacataatat ccatctgtga attggtacgc agtcgatgag tcctgagtaa      60
agtcatacgt taggacacac ttaaaaaaat ctccact                              97

<210> SEQ ID NO 127
<211> LENGTH: 94
<212> TYPE: DNA
<213> ORGANISM: Artificial Sequence
<220> FEATURE:
<223> OTHER INFORMATION: Oligonucleotide probe

<400> SEQUENCE: 127
ttcaacgatg atgttgttaa ctgtggtgaa ttggtacgca gtcgatgagt cctgagtaaa      60
gtagtcagat tttcgagtgg gaattgtgta ctcg                                 94

<210> SEQ ID NO 128
<211> LENGTH: 92
<212> TYPE: DNA
<213> ORGANISM: Artificial Sequence
<220> FEATURE:
<223> OTHER INFORMATION: Oligonucleotide probe

<400> SEQUENCE: 128
ttcaacgatg atgttgttaa ctgtggtgaa ttggtacgca gtcgatgagt cctgagtaaa      60
gtagtgattt tcgagtggga attgtgtact ca                                   92

<210> SEQ ID NO 129
<211> LENGTH: 89
<212> TYPE: DNA
<213> ORGANISM: Artificial Sequence
<220> FEATURE:
<223> OTHER INFORMATION: Oligonucleotide probe

<400> SEQUENCE: 129
gccctggtgt ttgcgtacta cagtgaattg gtacgcagtc gatgagtcct gagtaaagtt      60
cagcatgtga gagcatgcat gatgatggc                                       89

<210> SEQ ID NO 130
<211> LENGTH: 87
<212> TYPE: DNA
<213> ORGANISM: Artificial Sequence
<220> FEATURE:
<223> OTHER INFORMATION: Oligonucleotide probe

<400> SEQUENCE: 130
ccatcatcat gcatgctctc acgtgaattg gtacgcagtc gatgagtcct gagtaaagtt      60
cagctgtagt acgcaaacac cagggca                                         87

<210> SEQ ID NO 131
<211> LENGTH: 84
<212> TYPE: DNA
<213> ORGANISM: Artificial Sequence
<220> FEATURE:
<223> OTHER INFORMATION: Oligonucleotide probe

<400> SEQUENCE: 131

```
aagctggaag aactggtgct ggtgaattgg tacgcagtcg atgagtcctg agtaaagtag        60
gtgtaagccc agagatgtca gcag                                              84

<210> SEQ ID NO 132
<211> LENGTH: 82
<212> TYPE: DNA
<213> ORGANISM: Artificial Sequence
<220> FEATURE:
<223> OTHER INFORMATION: Oligonucleotide probe

<400> SEQUENCE: 132
tgctgacatc tctgggctta cacgtgaatt ggtacgcagt cgatgagtcc tgagtaaagg        60
cagcaccagt tcttccagct tg                                                82

<210> SEQ ID NO 133
<211> LENGTH: 79
<212> TYPE: DNA
<213> ORGANISM: Artificial Sequence
<220> FEATURE:
<223> OTHER INFORMATION: Oligonucleotide probe

<400> SEQUENCE: 133
ctacttgctg aagctgctag tgaattggta cgcagtcgat gagtcctgag taaagcgaat        60
gaaccatatc aagcaaagt                                                    79

<210> SEQ ID NO 134
<211> LENGTH: 77
<212> TYPE: DNA
<213> ORGANISM: Artificial Sequence
<220> FEATURE:
<223> OTHER INFORMATION: Oligonucleotide probe

<400> SEQUENCE: 134
ctacttgctg aagctgctag tgaattggta cgcagtcgat gagtcctgag taaagaatga        60
accatatcaa gcaaagc                                                      77

<210> SEQ ID NO 135
<211> LENGTH: 124
<212> TYPE: DNA
<213> ORGANISM: Artificial Sequence
<220> FEATURE:
<223> OTHER INFORMATION: Oligonucleotide probe

<400> SEQUENCE: 135
agtaatttta gaattcatta acaaaattac cgaattggta cgcagtcgat gagtcctgag        60
taatgcgatt agcgatacgt tagcgactta gccgtactgt tatatatgat cggaatgatt       120
acga                                                                   124

<210> SEQ ID NO 136
<211> LENGTH: 124
<212> TYPE: DNA
<213> ORGANISM: Artificial Sequence
<220> FEATURE:
<223> OTHER INFORMATION: Oligonucleotide probe

<400> SEQUENCE: 136
agtaatttta gaattcatta acaaaattac cgaattggta cgcagtcgat gagtcctgag        60
taatgcgatt agcgatacgt tagcgactta gccgtactgt tatatatgat cggaatgatt       120
acga                                                                   124
```

```
<210> SEQ ID NO 137
<211> LENGTH: 119
<212> TYPE: DNA
<213> ORGANISM: Artificial Sequence
<220> FEATURE:
<223> OTHER INFORMATION: Oligonucleotide probe

<400> SEQUENCE: 137
aagagggaaa ttagaaagca ctgaccgaat tggtacgcag tcgatgagtc ctgagtaatg      60
cattcgaaat cggactctga gactcatgcg atgactgaaa aagggttata ctggcgtga     119

<210> SEQ ID NO 138
<211> LENGTH: 117
<212> TYPE: DNA
<213> ORGANISM: Artificial Sequence
<220> FEATURE:
<223> OTHER INFORMATION: Oligonucleotide probe

<400> SEQUENCE: 138
aagagggaaa ttagaaagca ctgaccgaat tggtacgcag tcgatgagtc ctgagtaatg      60
ttcgaaatcg gactctgaga ctcatgcgat gactgaaaaa gggttatact ggcgtgg       117

<210> SEQ ID NO 139
<211> LENGTH: 114
<212> TYPE: DNA
<213> ORGANISM: Artificial Sequence
<220> FEATURE:
<223> OTHER INFORMATION: Oligonucleotide probe

<400> SEQUENCE: 139
aaatgatcaa ctatacatct ccaaaaccga attggtacgc agtcgatgag tcctgagtaa      60
tgatcagtcc agtcatggat ccgatcactc tgttaattga atattctaac ttat          114

<210> SEQ ID NO 140
<211> LENGTH: 112
<212> TYPE: DNA
<213> ORGANISM: Artificial Sequence
<220> FEATURE:
<223> OTHER INFORMATION: Oligonucleotide probe

<400> SEQUENCE: 140
aaatgatcaa ctatacatct ccaaaaccga attggtacgc agtcgatgag tcctgagtaa      60
tgcagtccag tcatggatcc gatcactctg ttaattgaat attctaactt aa            112

<210> SEQ ID NO 141
<211> LENGTH: 109
<212> TYPE: DNA
<213> ORGANISM: Artificial Sequence
<220> FEATURE:
<223> OTHER INFORMATION: Oligonucleotide probe

<400> SEQUENCE: 141
tttatatacc tgaaccaggc taattaccga attggtacgc agtcgatgag tcctgagtaa      60
tgcgacttcg ctaacgttac ggcatggatg ttcactttct ctaaatgac               109

<210> SEQ ID NO 142
<211> LENGTH: 107
<212> TYPE: DNA
<213> ORGANISM: Artificial Sequence
<220> FEATURE:
<223> OTHER INFORMATION: Oligonucleotide probe

<400> SEQUENCE: 142
```

```
tttatatacc tgaaccaggc taattaccga attggtacgc agtcgatgag tcctgagtaa    60
tgacttcgct aacgttacgg catggatgtt cactttctct aaatgat                107
```

<210> SEQ ID NO 143
<211> LENGTH: 104
<212> TYPE: DNA
<213> ORGANISM: Artificial Sequence
<220> FEATURE:
<223> OTHER INFORMATION: Oligonucleotide probe

<400> SEQUENCE: 143

```
tattagtcaa attagtgaat tccgtcccga attggtacgc agtcgatgag tcctgagtaa    60
tgactgcgga tcagctaaat aaatttgttg agtcgaatat aaag                   104
```

<210> SEQ ID NO 144
<211> LENGTH: 102
<212> TYPE: DNA
<213> ORGANISM: Artificial Sequence
<220> FEATURE:
<223> OTHER INFORMATION: Oligonucleotide probe

<400> SEQUENCE: 144

```
tattagtcaa attagtgaat tccgtcccga attggtacgc agtcgatgag tcctgagtaa    60
tgtgcggatc agctaaataa attggttgag tcgaatataa aa                     102
```

<210> SEQ ID NO 145
<211> LENGTH: 99
<212> TYPE: DNA
<213> ORGANISM: Artificial Sequence
<220> FEATURE:
<223> OTHER INFORMATION: Oligonucleotide probe

<400> SEQUENCE: 145

```
tggaggatta tcgcccttga atatccgaat tggtacgcag tcgatgagtc ctgagtaatg    60
tactggcata cgttacgtca ggtgcttctc agctgatgc                          99
```

<210> SEQ ID NO 146
<211> LENGTH: 97
<212> TYPE: DNA
<213> ORGANISM: Artificial Sequence
<220> FEATURE:
<223> OTHER INFORMATION: Oligonucleotide probe

<400> SEQUENCE: 146

```
tggaggatta tcgcccttga atatccgaat tggtacgcag tcgatgagtc ctgagtaatg    60
ctggcatacg ttacgtcagg tgcttctcag ctgatgt                            97
```

<210> SEQ ID NO 147
<211> LENGTH: 94
<212> TYPE: DNA
<213> ORGANISM: Artificial Sequence
<220> FEATURE:
<223> OTHER INFORMATION: Oligonucleotide probe

<400> SEQUENCE: 147

```
agaaagcttt gacaggactg acagccgaat tggtacgcag tcgatgagtc ctgagtaatg    60
gtggatcagc ttcaagtgaa ggcttcgctt aagc                               94
```

<210> SEQ ID NO 148
<211> LENGTH: 92
<212> TYPE: DNA
<213> ORGANISM: Artificial Sequence

```
<220> FEATURE:
<223> OTHER INFORMATION: Oligonucleotide probe

<400> SEQUENCE: 148
agaaagcttt gacaggactg acagccgaat tggtacgcag tcgatgagtc ctgagtaatg      60
ggatcagctt caagtgaagg cttcgcttaa gg                                   92

<210> SEQ ID NO 149
<211> LENGTH: 89
<212> TYPE: DNA
<213> ORGANISM: Artificial Sequence
<220> FEATURE:
<223> OTHER INFORMATION: Oligonucleotide probe

<400> SEQUENCE: 149
attgtcgttg acatgcaatc accccgaatt ggtacgcagt cgatgagtcc tgagtaatgc      60
tcaaatgata tcattatctt gagcttgaa                                       89

<210> SEQ ID NO 150
<211> LENGTH: 87
<212> TYPE: DNA
<213> ORGANISM: Artificial Sequence
<220> FEATURE:
<223> OTHER INFORMATION: Oligonucleotide probe

<400> SEQUENCE: 150
attgtcgttg acatgcaatc accccgaatt ggtacgcagt cgatgagtcc tgagtaatgc      60
caatgatatc attatcttga gcttgat                                         87

<210> SEQ ID NO 151
<211> LENGTH: 84
<212> TYPE: DNA
<213> ORGANISM: Artificial Sequence
<220> FEATURE:
<223> OTHER INFORMATION: Oligonucleotide probe

<400> SEQUENCE: 151
ccaggaataa aagctagact ccccCgaatt ggtacgcagt cgatgagtcc tgagtaatgc      60
acaccagcac taacgctgaa gttc                                            84

<210> SEQ ID NO 152
<211> LENGTH: 82
<212> TYPE: DNA
<213> ORGANISM: Artificial Sequence
<220> FEATURE:
<223> OTHER INFORMATION: Oligonucleotide probe

<400> SEQUENCE: 152
ccaggaataa aagctagact ccccCgaatt ggtacgcagt cgatgagtcc tgagtaatgc      60
accagcacta acgctgaagt tt                                              82

<210> SEQ ID NO 153
<211> LENGTH: 79
<212> TYPE: DNA
<213> ORGANISM: Artificial Sequence
<220> FEATURE:
<223> OTHER INFORMATION: Oligonucleotide probe

<400> SEQUENCE: 153
cgctgcatct gctggtgtcc cgaattggta cgcagtcgat gagtcctgag taatggtcac      60
atcccaactg catcataag                                                  79
```

<210> SEQ ID NO 154
<211> LENGTH: 77
<212> TYPE: DNA
<213> ORGANISM: Artificial Sequence
<220> FEATURE:
<223> OTHER INFORMATION: Oligonucleotide probe

<400> SEQUENCE: 154
cgctgcatct gctggtgtcc gaattggtac gcagtcgatg agtcctgagt aatgtcacat      60
cccaactgca tcataaa                                                    77

<210> SEQ ID NO 155
<211> LENGTH: 124
<212> TYPE: DNA
<213> ORGANISM: Artificial Sequence
<220> FEATURE:
<223> OTHER INFORMATION: Oligonucleotide probe

<400> SEQUENCE: 155
gtacaatgca atttagagaa caagcgggaa ttggtacgca gtcgatgagt cctgagtaac      60
gctgatccga tcgatatcga cgtagctgca tcgtaatcgg gaagtattca gagtttagag     120
tgaa                                                                 124

<210> SEQ ID NO 156
<211> LENGTH: 122
<212> TYPE: DNA
<213> ORGANISM: Artificial Sequence
<220> FEATURE:
<223> OTHER INFORMATION: Oligonucleotide probe

<400> SEQUENCE: 156
gtacaatgca atttagagaa caagcgggaa ttggtacgca gtcgatgagt cctgagtaac      60
gcatccgatc gatatcgacg tagctgcatc gtaatcggga agtattcaga gtttagagtg     120
at                                                                   122

<210> SEQ ID NO 157
<211> LENGTH: 119
<212> TYPE: DNA
<213> ORGANISM: Artificial Sequence
<220> FEATURE:
<223> OTHER INFORMATION: Oligonucleotide probe

<400> SEQUENCE: 157
cttaacacgt ccagacaaga ggcgggaatt ggtacgcagt cgatgagtcc tgagtaacgc      60
accatgtcga cgtagatccg tatagcactg agtcgcaaag aattagacat ggatgagtt     119

<210> SEQ ID NO 158
<211> LENGTH: 117
<212> TYPE: DNA
<213> ORGANISM: Artificial Sequence
<220> FEATURE:
<223> OTHER INFORMATION: Oligonucleotide probe

<400> SEQUENCE: 158
cttaacacgt ccagacaaga ggcgggaatt ggtacgcagt cgatgagtcc tgagtaacgc      60
ccatgtcgac gtagatccgt atagcactga gtccaaagat ttagacatgg aggagtc       117

<210> SEQ ID NO 159
<211> LENGTH: 114
<212> TYPE: DNA
<213> ORGANISM: Artificial Sequence

```
<220> FEATURE:
<223> OTHER INFORMATION: Oligonucleotide probe

<400> SEQUENCE: 159
ttaacaagaa aaatcggtca ggactgggaa ttggtacgca gtcgatgagt cctgagtaac      60
gccgtacgca tgctaacgtt acggactatc tagtttgagc agttttgagc tgaa           114

<210> SEQ ID NO 160
<211> LENGTH: 112
<212> TYPE: DNA
<213> ORGANISM: Artificial Sequence
<220> FEATURE:
<223> OTHER INFORMATION: Oligonucleotide probe

<400> SEQUENCE: 160
ttaacaagaa aaatcggtca ggactgggaa ttggtacgca gtcgatgagt cctgagtaac      60
gctacgcatg ctaacgttac ggactatcta gtttgagcag ttttgagctg ag             112

<210> SEQ ID NO 161
<211> LENGTH: 109
<212> TYPE: DNA
<213> ORGANISM: Artificial Sequence
<220> FEATURE:
<223> OTHER INFORMATION: Oligonucleotide probe

<400> SEQUENCE: 161
acgcttcttc cttgttgaga gggggaatt ggtacgcagt cgatgagtcc tgagtaacgc       60
cgatgctcag gctatcgaca tgttcatatt gatggttttg tttttgtta                 109

<210> SEQ ID NO 162
<211> LENGTH: 107
<212> TYPE: DNA
<213> ORGANISM: Artificial Sequence
<220> FEATURE:
<223> OTHER INFORMATION: Oligonucleotide probe

<400> SEQUENCE: 162
acgcttcttc cttgttgaga gggggaatt ggtacgcagt cgatgagtcc tgagtaacgc       60
atgctcaggc tatcgacatg ttcatattga tggttttgtt tttgttg                   107

<210> SEQ ID NO 163
<211> LENGTH: 104
<212> TYPE: DNA
<213> ORGANISM: Artificial Sequence
<220> FEATURE:
<223> OTHER INFORMATION: Oligonucleotide probe

<400> SEQUENCE: 163
ctctgcagag atagatcata acctgggaat tggtacgcag tcgatgagtc ctgagtaacg     60
catcacgtca tgctgagcat agctttgcaa cagcagaagt gtat                      104

<210> SEQ ID NO 164
<211> LENGTH: 102
<212> TYPE: DNA
<213> ORGANISM: Artificial Sequence
<220> FEATURE:
<223> OTHER INFORMATION: Oligonucleotide probe

<400> SEQUENCE: 164
ctctgcagag atagatcata acctgggaat tggtacgcag tcgatgagtc ctgagtaacg     60
ccacgtcatg ctgagcatag ctttgcaaca gcagaagtgt ac                        102
```

<210> SEQ ID NO 165
<211> LENGTH: 99
<212> TYPE: DNA
<213> ORGANISM: Artificial Sequence
<220> FEATURE:
<223> OTHER INFORMATION: Oligonucleotide probe

<400> SEQUENCE: 165
gaactataaa ttgcttgcag gaaccgggaa ttggtacgca gtcgatgagt cctgagtaac     60
gctcgctaac gttacgctct cttgtttgtt gcaggagca                            99

<210> SEQ ID NO 166
<211> LENGTH: 97
<212> TYPE: DNA
<213> ORGANISM: Artificial Sequence
<220> FEATURE:
<223> OTHER INFORMATION: Oligonucleotide probe

<400> SEQUENCE: 166
gaactataaa ttgcttgcag gaaccgggaa ttggtacgca gtcgatgagt cctgagtaac     60
gcgctaacgt tacgcactct tgtttgttgc aggagct                              97

<210> SEQ ID NO 167
<211> LENGTH: 94
<212> TYPE: DNA
<213> ORGANISM: Artificial Sequence
<220> FEATURE:
<223> OTHER INFORMATION: Oligonucleotide probe

<400> SEQUENCE: 167
aactctcaat ttttcaacct tctctaggga attggtacgc agtcgatgag tcctgagtaa     60
cgcgtcattc gaatcactgg ctggaacttc tccc                                 94

<210> SEQ ID NO 168
<211> LENGTH: 92
<212> TYPE: DNA
<213> ORGANISM: Artificial Sequence
<220> FEATURE:
<223> OTHER INFORMATION: Oligonucleotide probe

<400> SEQUENCE: 168
aactctcaat ttttcaacct tctctaggga attggtacgc agtcgatgag tcctgagtaa     60
cgccattcga atcactggct ggaacttctc cg                                   92

<210> SEQ ID NO 169
<211> LENGTH: 89
<212> TYPE: DNA
<213> ORGANISM: Artificial Sequence
<220> FEATURE:
<223> OTHER INFORMATION: Oligonucleotide probe

<400> SEQUENCE: 169
ttcttttgtt atagcaagag cttgaaggga attggtacgc agtcgatgag tcctgagtaa     60
cgcccgatgt atgcatgatt ggcggtcca                                       89

<210> SEQ ID NO 170
<211> LENGTH: 87
<212> TYPE: DNA
<213> ORGANISM: Artificial Sequence
<220> FEATURE:
<223> OTHER INFORMATION: Oligonucleotide probe

<400> SEQUENCE: 170

```
ttcttttgtt atagcaagag cttgaaggga attggtacgc agtcgatgag tcctgagtaa    60
cgccatgtat gcatgattgg cggtccg                                       87

<210> SEQ ID NO 171
<211> LENGTH: 84
<212> TYPE: DNA
<213> ORGANISM: Artificial Sequence
<220> FEATURE:
<223> OTHER INFORMATION: Oligonucleotide probe

<400> SEQUENCE: 171
tcacaagctc ccatcgcatc atgggaattg gtacgcagtc gatgagtcct gagtaacgct    60
gttgttcctt gttgcatctc cttt                                          84

<210> SEQ ID NO 172
<211> LENGTH: 82
<212> TYPE: DNA
<213> ORGANISM: Artificial Sequence
<220> FEATURE:
<223> OTHER INFORMATION: Oligonucleotide probe

<400> SEQUENCE: 172
tcacaagctc ccatcgcatc atgggaattg gtacgcagtc gatgagtcct gagtaacggt    60
tgttccttgt tgcatctcct tg                                            82

<210> SEQ ID NO 173
<211> LENGTH: 79
<212> TYPE: DNA
<213> ORGANISM: Artificial Sequence
<220> FEATURE:
<223> OTHER INFORMATION: Oligonucleotide probe

<400> SEQUENCE: 173
acacgagcct cggatcaatg ggaattggta cgcagtcgat gagtcctgag taacgtgcaa    60
cagttgaata gaaagatgt                                                79

<210> SEQ ID NO 174
<211> LENGTH: 77
<212> TYPE: DNA
<213> ORGANISM: Artificial Sequence
<220> FEATURE:
<223> OTHER INFORMATION: Oligonucleotide probe

<400> SEQUENCE: 174
acacgagcct cggatcaatg ggaattggta cgcagtcgat gagtcctgag taacgcaaca    60
gttgaataga aagatgc                                                  77

<210> SEQ ID NO 175
<211> LENGTH: 124
<212> TYPE: DNA
<213> ORGANISM: Artificial Sequence
<220> FEATURE:
<223> OTHER INFORMATION: Oligonucleotide probe

<400> SEQUENCE: 175
tcacaagctc ccatcgcatc atagagaatt ggtacgcagt cgatgagtcc tgagtaagcg    60
actcgtacca tgtcgacgta gatccgtata gcactgagtc gttgttcctt gttgcatctc   120
cttg                                                               124

<210> SEQ ID NO 176
```

<211> LENGTH: 122
<212> TYPE: DNA
<213> ORGANISM: Artificial Sequence
<220> FEATURE:
<223> OTHER INFORMATION: Oligonucleotide probe

<400> SEQUENCE: 176
tcacaagctc ccatcgcatc atagagaatt ggtacgcagt cgatgagtcc tgagtaagcc    60
tcgtaccatg tcgacgtaga tccgtatagc actgagtcgt tgttccttgt tgcatctcct   120
tt                                                                  122

<210> SEQ ID NO 177
<211> LENGTH: 119
<212> TYPE: DNA
<213> ORGANISM: Artificial Sequence
<220> FEATURE:
<223> OTHER INFORMATION: Oligonucleotide probe

<400> SEQUENCE: 177
gcaccaggac tgggtatact tatgagaatt ggtacgcagt cgatgagtcc tgagtaagcg    60
atccgatcga tatcgacgta gctgcatcgt aatcggaggt ggtaagatat gtcaagcag   119

<210> SEQ ID NO 178
<211> LENGTH: 117
<212> TYPE: DNA
<213> ORGANISM: Artificial Sequence
<220> FEATURE:
<223> OTHER INFORMATION: Oligonucleotide probe

<400> SEQUENCE: 178
gcaccaggac tgggtatact tatgagaatt ggtacgcagt cgatgagtcc tgagtaagct    60
ccgatcgata tcgacgtagc tgcatcgtaa tcgagggtgg taagatatgt caagcaa     117

<210> SEQ ID NO 179
<211> LENGTH: 114
<212> TYPE: DNA
<213> ORGANISM: Artificial Sequence
<220> FEATURE:
<223> OTHER INFORMATION: Oligonucleotide probe

<400> SEQUENCE: 179
tctcttggca tcaagaaagt gatggagaat tggtacgcag tcgatgagtc ctgagtaagc    60
tatcgagtcg actacgttgc atacggatct attagtgttt gggacagtgt ctta        114

<210> SEQ ID NO 180
<211> LENGTH: 112
<212> TYPE: DNA
<213> ORGANISM: Artificial Sequence
<220> FEATURE:
<223> OTHER INFORMATION: Oligonucleotide probe

<400> SEQUENCE: 180
tctcttggca tcaagaaagt gatggagaat tggtacgcag tcgatgagtc ctgagtaagc    60
tcgagtcgac tacgttgcat acggatctat tagtgtttgg gacagtgtct tg          112

<210> SEQ ID NO 181
<211> LENGTH: 109
<212> TYPE: DNA
<213> ORGANISM: Artificial Sequence
<220> FEATURE:
<223> OTHER INFORMATION: Oligonucleotide probe

<400> SEQUENCE: 181

```
gatagagatg gtaccattag agttagagaa ttggtacgca gtcgatgagt cctgagtaag      60
cgtagatccg tatagcactg agtccctata atgagtctaa gacatcaac                 109

<210> SEQ ID NO 182
<211> LENGTH: 107
<212> TYPE: DNA
<213> ORGANISM: Artificial Sequence
<220> FEATURE:
<223> OTHER INFORMATION: Oligonucleotide probe

<400> SEQUENCE: 182
gatagagacg ataccattag agttagagaa ttggtacgca gtcgatgagt cctgagtaag      60
cgtagatccg tatagcactg agcctataat gagtctaaga catcaat                   107

<210> SEQ ID NO 183
<211> LENGTH: 104
<212> TYPE: DNA
<213> ORGANISM: Artificial Sequence
<220> FEATURE:
<223> OTHER INFORMATION: Oligonucleotide probe

<400> SEQUENCE: 183
gacatttgat gtttgaagta taagtatgag aattggtacg cagtcgatga gtcctgagta      60
agctcgacgt gctatgcagg tgttgatgtg ctatgaaata ttga                      104

<210> SEQ ID NO 184
<211> LENGTH: 102
<212> TYPE: DNA
<213> ORGANISM: Artificial Sequence
<220> FEATURE:
<223> OTHER INFORMATION: Oligonucleotide probe

<400> SEQUENCE: 184
gacatttgat gtttgaagta taagtatgag aattggtacg cagtcgatga gtcctgagta      60
agccgacgtg ctatgcagtg ttgatgtgct acgaaatatt gg                        102

<210> SEQ ID NO 185
<211> LENGTH: 99
<212> TYPE: DNA
<213> ORGANISM: Artificial Sequence
<220> FEATURE:
<223> OTHER INFORMATION: Oligonucleotide probe

<400> SEQUENCE: 185
gtccacattc tgcttcttca tttggagaat tggtacgcag tcgatgagtc ctgagtaagc      60
gtgcatatgc cagtgtagac aaatatgctt cgactaact                            99

<210> SEQ ID NO 186
<211> LENGTH: 97
<212> TYPE: DNA
<213> ORGANISM: Artificial Sequence
<220> FEATURE:
<223> OTHER INFORMATION: Oligonucleotide probe

<400> SEQUENCE: 186
gtccacattc tgcttcttca tttggagaat tggtacgcag tcgatgagtc ctgagtaagc      60
gcatatgcca gtgtagacaa atatgcttcg actaacc                              97

<210> SEQ ID NO 187
<211> LENGTH: 94
<212> TYPE: DNA
```

```
<213> ORGANISM: Artificial Sequence
<220> FEATURE:
<223> OTHER INFORMATION: Oligonucleotide probe

<400> SEQUENCE: 187
aatacaataa aatcaatagg gcaaaaggag aattggtacg cagtcgatga gtcctgagta      60
agcctacgga ctctctaggt gaggcctgga ccat                                 94

<210> SEQ ID NO 188
<211> LENGTH: 94
<212> TYPE: DNA
<213> ORGANISM: Artificial Sequence
<220> FEATURE:
<223> OTHER INFORMATION: Oligonucleotide probe

<400> SEQUENCE: 188
aatacaataa aatcaatagg gcaaaaggag aattggtacg cagtcgatga gtcctgagta      60
agcctacgga ctctctaggt gaggcctgga ccat                                 94

<210> SEQ ID NO 189
<211> LENGTH: 89
<212> TYPE: DNA
<213> ORGANISM: Artificial Sequence
<220> FEATURE:
<223> OTHER INFORMATION: Oligonucleotide probe

<400> SEQUENCE: 189
agaagcacat cgggatctac cacgagaatt ggtacgcagt cgatgagtcc tgagtaagcc      60
cgattgaagc atagatatag acagatcac                                       89

<210> SEQ ID NO 190
<211> LENGTH: 87
<212> TYPE: DNA
<213> ORGANISM: Artificial Sequence
<220> FEATURE:
<223> OTHER INFORMATION: Oligonucleotide probe

<400> SEQUENCE: 190
agaagcacat tgggatctac cacgagaatt ggtacgcagt cgatgagtcc tgagtaagcg      60
attgaagcat agatatagac agatcaa                                         87

<210> SEQ ID NO 191
<211> LENGTH: 84
<212> TYPE: DNA
<213> ORGANISM: Artificial Sequence
<220> FEATURE:
<223> OTHER INFORMATION: Oligonucleotide probe

<400> SEQUENCE: 191
acacgagcct cggatcaatg gcgagaattg gtacgcagtc gatgagtcct gagtaagcgg      60
tgcaacagtt gaatagaaag atgt                                            84

<210> SEQ ID NO 192
<211> LENGTH: 82
<212> TYPE: DNA
<213> ORGANISM: Artificial Sequence
<220> FEATURE:
<223> OTHER INFORMATION: Oligonucleotide probe

<400> SEQUENCE: 192
acacgagcct cggatcaatg gcgagaattg gtacgcagtc gatgagtcct gagtaagctg      60
caacagttga atagaaagat gc                                              82
```

<210> SEQ ID NO 193
<211> LENGTH: 79
<212> TYPE: DNA
<213> ORGANISM: Artificial Sequence
<220> FEATURE:
<223> OTHER INFORMATION: Oligonucleotide probe

<400> SEQUENCE: 193
gttgcaatcg ctccttgaat tgagaattgg tacgcagtcg atgagtcctg agtaagcgcc     60
atcaaatact ggctagatc                                                  79

<210> SEQ ID NO 194
<211> LENGTH: 77
<212> TYPE: DNA
<213> ORGANISM: Artificial Sequence
<220> FEATURE:
<223> OTHER INFORMATION: Oligonucleotide probe

<400> SEQUENCE: 194
gttgcaatcg ctccttgaat tgagaattgg tacgcagtcg atgagtcctg agtaagccat     60
caaatactgg ctagatt                                                    77

<210> SEQ ID NO 195
<211> LENGTH: 120
<212> TYPE: DNA
<213> ORGANISM: Artificial Sequence
<220> FEATURE:
<223> OTHER INFORMATION: Oligonucleotide probe

<400> SEQUENCE: 195
gtacaatgca atttagagaa caagcggaat tggtacgcag tcgatgagtc ctgagtaagg     60
atccgatcga tatcgacgta gctgcatcgt aatcgggaag tattcagagt ttagagtgaa    120

<210> SEQ ID NO 196
<211> LENGTH: 118
<212> TYPE: DNA
<213> ORGANISM: Artificial Sequence
<220> FEATURE:
<223> OTHER INFORMATION: Oligonucleotide probe

<400> SEQUENCE: 196
gtacaatgca atttagagaa caagcggaat tggtacgcag tcgatgagtc ctgagtaagt     60
ccgatcgata tcgacgtagc tgcatcgtaa tcgggaagta ttcagagttt agagtgat      118

<210> SEQ ID NO 197
<211> LENGTH: 116
<212> TYPE: DNA
<213> ORGANISM: Artificial Sequence
<220> FEATURE:
<223> OTHER INFORMATION: Oligonucleotide probe

<400> SEQUENCE: 197
cttaacacgt ccagacaaga ggcggaattg gtacgcagtc gatgagtcct gagtaagacc     60
atgtcgacgt agatccgtat agcactgagt cgcaaagaat tagacatgga tgagtt       116

<210> SEQ ID NO 198
<211> LENGTH: 114
<212> TYPE: DNA
<213> ORGANISM: Artificial Sequence
<220> FEATURE:
<223> OTHER INFORMATION: Oligonucleotide probe

```
<400> SEQUENCE: 198
cttaacacgt ccagacaaga ggcggaattg gtacgcagtc gatgagtcct gagtaagcca    60
tgtcgacgta gatccgtata gcactgagtc caaagattta gacatggagg agtc          114

<210> SEQ ID NO 199
<211> LENGTH: 112
<212> TYPE: DNA
<213> ORGANISM: Artificial Sequence
<220> FEATURE:
<223> OTHER INFORMATION: Oligonucleotide probe

<400> SEQUENCE: 199
ttaacaagaa aaatcggtca ggactggaat tggtacgcag tcgatgagtc ctgagtaagc    60
gtacgcatgc taacgttacg gactatcgta gtttgagcag ttttgagctg aa            112

<210> SEQ ID NO 200
<211> LENGTH: 110
<212> TYPE: DNA
<213> ORGANISM: Artificial Sequence
<220> FEATURE:
<223> OTHER INFORMATION: Oligonucleotide probe

<400> SEQUENCE: 200
ttaacaagaa aaatcggtca ggactggaat tggtacgcag tcgatgagtc ctgagtaagt    60
acgcatgcta acgttacgga ctatcgtagt ttgagcagtt ttgagctgag              110

<210> SEQ ID NO 201
<211> LENGTH: 108
<212> TYPE: DNA
<213> ORGANISM: Artificial Sequence
<220> FEATURE:
<223> OTHER INFORMATION: Oligonucleotide probe

<400> SEQUENCE: 201
acgcttcttc cttgttgaga gggggaattg gtacgcagtc gatgagtcct gagtaagcta    60
gatgctcagg ctatcgacat gttcatattg atggttttgt ttttgtta               108

<210> SEQ ID NO 202
<211> LENGTH: 106
<212> TYPE: DNA
<213> ORGANISM: Artificial Sequence
<220> FEATURE:
<223> OTHER INFORMATION: Oligonucleotide probe

<400> SEQUENCE: 202
acgcttcttc cttgttgaga gggggaattg gtacgcagtc gatgagtcct gagtaagaga    60
tgctcaggct atcgacatgt tcatattgat ggttttgttt ttgttg                 106

<210> SEQ ID NO 203
<211> LENGTH: 104
<212> TYPE: DNA
<213> ORGANISM: Artificial Sequence
<220> FEATURE:
<223> OTHER INFORMATION: Oligonucleotide probe

<400> SEQUENCE: 203
ctctgcagag atagatcata acctggaatt ggtacgcagt cgatgagtcc tgagtaagga    60
gatcacgtca tgctgagcat agctttgcaa cagcagaagt gtat                    104

<210> SEQ ID NO 204
<211> LENGTH: 102
```

```
<212> TYPE: DNA
<213> ORGANISM: Artificial Sequence
<220> FEATURE:
<223> OTHER INFORMATION: Oligonucleotide probe

<400> SEQUENCE: 204
ctctgcagag atagatcata acctggaatt ggtacgcagt cgatgagtcc tgagtaagga    60
tcacgtcatg ctgagcatag ctttgcaaca gcagaagtgt ac                     102

<210> SEQ ID NO 205
<211> LENGTH: 100
<212> TYPE: DNA
<213> ORGANISM: Artificial Sequence
<220> FEATURE:
<223> OTHER INFORMATION: Oligonucleotide probe

<400> SEQUENCE: 205
gaactataaa ttgcttgcag gaaccggaat tggtacgcag tcgatgagtc ctgagtaagt    60
cgctaacgtt acggcatctc tcttgtttgt tgcaggagca                        100

<210> SEQ ID NO 206
<211> LENGTH: 98
<212> TYPE: DNA
<213> ORGANISM: Artificial Sequence
<220> FEATURE:
<223> OTHER INFORMATION: Oligonucleotide probe

<400> SEQUENCE: 206
gaactataaa ttgcttgcag gaaccggaat tggtacgcag tcgatgagtc ctgagtaagg    60
ctaacgttac ggcatcactc ttgtttgttg caggagct                           98

<210> SEQ ID NO 207
<211> LENGTH: 96
<212> TYPE: DNA
<213> ORGANISM: Artificial Sequence
<220> FEATURE:
<223> OTHER INFORMATION: Oligonucleotide probe

<400> SEQUENCE: 207
acacgagcct cggatcaatg gcggaattgg tacgcagtcg atgagtcctg agtaagtgct    60
agcacgtact ggtgcaacag ttgaatagaa agatgt                             96

<210> SEQ ID NO 208
<211> LENGTH: 94
<212> TYPE: DNA
<213> ORGANISM: Artificial Sequence
<220> FEATURE:
<223> OTHER INFORMATION: Oligonucleotide probe

<400> SEQUENCE: 208
acacgagcct cggatcaatg gcggaattgg tacgcagtcg atgagtcctg agtaagctag    60
cacgtactgg tgcaacagtt gaatagaaag atgc                               94

<210> SEQ ID NO 209
<211> LENGTH: 92
<212> TYPE: DNA
<213> ORGANISM: Artificial Sequence
<220> FEATURE:
<223> OTHER INFORMATION: Oligonucleotide probe

<400> SEQUENCE: 209
ttcttttgtt atagcaagag cttgaaggaa ttggtacgca gtcgatgagt cctgagtaag    60
```

-continued

```
ccgattagca tgtatgcatg attggcggtc ca                                    92

<210> SEQ ID NO 210
<211> LENGTH: 90
<212> TYPE: DNA
<213> ORGANISM: Artificial Sequence
<220> FEATURE:
<223> OTHER INFORMATION: Oligonucleotide probe

<400> SEQUENCE: 210
ttcttttgtt atagcaagag cttgaaggaa ttggtacgca gtcgatgagt cctgagtaag      60
ccgtagcatg tatgcatgat tggcggtccg                                       90

<210> SEQ ID NO 211
<211> LENGTH: 88
<212> TYPE: DNA
<213> ORGANISM: Artificial Sequence
<220> FEATURE:
<223> OTHER INFORMATION: Oligonucleotide probe

<400> SEQUENCE: 211
tcacaagctc ccatcgcatc ataggaattg gtacgcagtc gatgagtcct gagtaagcgt      60
tacggttgtt ccttgttgca tctccttt                                         88

<210> SEQ ID NO 212
<211> LENGTH: 86
<212> TYPE: DNA
<213> ORGANISM: Artificial Sequence
<220> FEATURE:
<223> OTHER INFORMATION: Oligonucleotide probe

<400> SEQUENCE: 212
tcacaagctc ccatcgcatc ataggaattg gtacgcagtc gatgagtcct gagtaagcta      60
cggttgttcc ttgttgcatc tccttg                                           86

<210> SEQ ID NO 213
<211> LENGTH: 84
<212> TYPE: DNA
<213> ORGANISM: Artificial Sequence
<220> FEATURE:
<223> OTHER INFORMATION: Oligonucleotide

<400> SEQUENCE: 213
aactctcaat ttttcaacct tctctaggaa ttggtacgca gtcgatgagt cctgagtaag      60
gtatcactgg ctggaacttc tccc                                             84

<210> SEQ ID NO 214
<211> LENGTH: 82
<212> TYPE: DNA
<213> ORGANISM: Artificial Sequence
<220> FEATURE:
<223> OTHER INFORMATION: Oligonucleotide probe

<400> SEQUENCE: 214
aactctcaat ttttcaacct tctctaggaa ttggtacgca gtcgatgagt cctgagtaag      60
atcactggct ggaacttctc cg                                               82

<210> SEQ ID NO 215
<211> LENGTH: 16
<212> TYPE: DNA
<213> ORGANISM: Artificial Sequence
<220> FEATURE:
<223> OTHER INFORMATION: Primer
```

```
<400> SEQUENCE: 215
gatgagtcct gagtaa                                                            16

<210> SEQ ID NO 216
<211> LENGTH: 16
<212> TYPE: DNA
<213> ORGANISM: Artificial Sequence
<220> FEATURE:
<223> OTHER INFORMATION: Primer

<400> SEQUENCE: 216
gactgcgtac caattc                                                            16

<210> SEQ ID NO 217
<211> LENGTH: 17
<212> TYPE: DNA
<213> ORGANISM: Artificial Sequence
<220> FEATURE:
<223> OTHER INFORMATION: Primer

<400> SEQUENCE: 217
gactgcgtac caattca                                                           17

<210> SEQ ID NO 218
<211> LENGTH: 17
<212> TYPE: DNA
<213> ORGANISM: Artificial Sequence
<220> FEATURE:
<223> OTHER INFORMATION: Primer

<400> SEQUENCE: 218
gactgcgtac caattcg                                                           17

<210> SEQ ID NO 219
<211> LENGTH: 17
<212> TYPE: DNA
<213> ORGANISM: Artificial Sequence
<220> FEATURE:
<223> OTHER INFORMATION: Primer

<400> SEQUENCE: 219
gactgcgtac caattct                                                           17

*
```

The invention claimed is:

1. A method for determining the presence or absence of at least two target sequences in a nucleic acid sample, wherein the method comprises the steps of:

(a) providing to a nucleic acid sample at least one circularizable probe for each target sequence to be detected in the sample, wherein (i) the probe has a first target-specific section at its 5'-end that is complementary to a first part of a target sequence and a second target-specific section at its 3'-end that is complementary to a second part of the target sequence, the first and the second parts of the target sequence being adjacent to each other, and (ii) the probe further comprises a tag sequence that is noncomplementary to the target sequence, said tag sequence comprising at least one primer-binding sequence and, optionally, a stuffer sequence;

(b) allowing the first and the second target specific sections of the circularizable probe to anneal to the first and second parts of target sequences so that the 5' end of the first and the 3' end of the second target specific sections of the circularizable probe are annealed adjacently on the target sequence;

(c) providing a means for connecting the first and second target specific sections that are adjacently annealed to the target sequence and permitting the first and the second target specific sections to be connected, resulting in a connected circular probe that corresponds to a target sequence in the sample;

(d) adding to said annealed circular probe a primer pair comprising (i) a first primer that is complementary to a first primer-binding sequence, (ii) a polymerase enzyme, and (iii) optionally, a second primer that is complementary to a second primer-binding sequence,
  thereby forming a mixture;
(e) amplifying the mixture, thereby producing a population of corresponding amplified connected probes or amplicons each of which is a linear monomeric representation of the connected circularizable probes;
(f) determining the presence or absence of a target sequence in the sample by detecting the presence or absence of the corresponding amplified linked probe or amplicon,
  wherein the at least one circularizable probe includes a blocking region that blocks elongation or amplification of the primer annealed to the connected circularizable probe,
with the proviso that, if the blocking region comprises a recognition site for a restriction endonuclease, the connected circularizable probe is subjected to restriction enzyme cleavage prior to the amplification step, and
the presence of said amplicon is indicative of the presence of, and the absence of said amplicon is indicative of the absence of, said target sequence in the sample.

2. A method according to claim 1, wherein an amplicon corresponding to one target sequence in the sample differs in length from an amplicon corresponding to a different target sequence.

3. A method according to claim 2, wherein the amplicon's length corresponds to the length of the connected circularizable probe.

4. A method according to claim 2, wherein a gap created by the difference in length between the amplicons is filled by the stuffer sequence.

5. A method according to claim 1, wherein the amplicons corresponding to different target sequences in the sample differ in length by at least two nucleotides.

6. A method according to claim 1, wherein two different circularizable probes include the same primer binding sequence capable of hybridizing to a single primer sequence.

7. A method according to claim 1 wherein at least one of the primers is detectably labeled.

8. A method according to claim 1, wherein at least one of the primers is a selective primer that includes at least one selective nucleotide at its 3'-end.

9. A method according to claim 1, wherein:
(i) step (a) comprises addition of at least two groups of circularizable oligonucleotide probes, each of which has a tag sequence complementary to at least one primer-binding sequence that is complementary to the sequence of one of said at least two groups;
(ii) the connected circularizable probes of each group are amplified from a primer pair wherein
  (A) at least one of the two primers is complementary to the primer binding sequence of one of said at least two groups, and
  (B) at least one of the primers of a group comprises a label that is specific for the primer binding sequence of said group and thereby permits identification of the probe with the complementary primer binding sequence; and,
(iii) within each group, an amplified, connected probe corresponding to a target sequence in the sample, differs in length from an amplified connected probe corresponding to a different target sequence in the sample.

10. A method according to claim 9, wherein amplified connected probes produced in a first set of said groups have an even number of nucleotides and amplified connected probes produced in a second set of said groups, have an odd number of nucleotides.

11. A method according to claim 10, wherein the groups of connected amplified probes having an even number of nucleotides are labeled with a first fluorescent label, and the groups of connected amplified probes having an odd number of nucleotides are labeled with a second fluorescent label, wherein the two fluorescent labels are selected to minimize overlap in their emission spectra.

12. A method according to claim 11, wherein
(i) a first and a second group of connected amplified probes having an even number of nucleotides are produced, and
(ii) a third and a fourth group of connected amplified probes having an odd number of nucleotides are produced, and wherein
  (A) the first and second group of probes are labeled with fluorescent label FAM and fluorescent label NED, respectively, and the third and fourth group of probes are labeled with fluorescent label (ET)-ROX and either fluorescent label JOE or HEX, respectively; or
  (B) the first and second group of probes are labeled with fluorescent label (ET)-ROX and either fluorescent label JOE or fluorescent label HEX, respectively, and the third and fourth group of probes are labeled with fluorescent label FAM and fluorescent label NED, respectively.

13. A method according to claim 1 wherein the blocking region that blocks primer elongation comprises a blocking group located between the two primer binding sequences, such that the blocking group is excluded from primer elongation or amplification.

14. A method according to claim 13, wherein the blocking group is located adjacent to the 3' end of a forward primer binding sequence and adjacent to the 5'-end of a reverse primer binding sequence.

15. A method according to claim 1, wherein the blocking region includes a DNA or RNA restriction site or an RNA nucleotide that is susceptible to cleavage or restriction by an RNAse or a restriction endonuclease.

16. A method according to claim 15, wherein the connected probe is restricted prior to the primer elongation or amplification step using a restriction endonuclease, optionally in the presence of an oligonucleotide complementary to an endonuclease recognition site, which oligonucleotide is capable of hybridizing to said recognition site and creating a double stranded segment susceptible to restriction by the restriction endonuclease.

17. A method according to claim 1, wherein the polymerase does not express strand displacing activity.

18. A method according to claim 1, wherein the target sequence comprises a polymorphism.

19. A method according to claim 18 wherein the polymorphism is a single nucleotide polymorphism.

20. A method according to claim 1, wherein the target sequence is in a DNA molecule selected from the group consisting of: cDNA, genomic DNA, a restriction fragment, an adapter-ligated restriction fragment, an amplified adapter-ligated restriction fragment and an AFLP fragment.

* * * * *